United States Patent
Eguchi et al.

(10) Patent No.: US 6,949,585 B2
(45) Date of Patent: Sep. 27, 2005

(54) CYCLOOCTANONE DERIVATIVES AND CYCLODECANONE DERIVATIVE, AND USE THEREOF

(75) Inventors: Yoshihito Eguchi, Kashiwa (JP); Ken-ichi Chiba, Tsuchiura (JP); Masaki Goto, Tsuchiura (JP); Hiroshi Obaishi, Tsukuba (JP); Yoshikazu Kuboi, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/473,568

(22) PCT Filed: Apr. 1, 2002

(86) PCT No.: PCT/JP02/03258

§ 371 (c)(1),
(2), (4) Date: Oct. 1, 2004

(87) PCT Pub. No.: WO02/081420

PCT Pub. Date: Oct. 17, 2002

(65) Prior Publication Data

US 2004/0082805 A1 Apr. 29, 2004

(30) Foreign Application Priority Data

Apr. 3, 2001 (JP) ........................................ 2001-104075

(51) Int. Cl.$^7$ ...................... A61K 31/24; A61K 31/235; A61K 31/12; C07C 205/00; C07C 69/76
(52) U.S. Cl. ........................ 514/535; 514/544; 514/683; 560/20; 560/73; 560/106; 568/329
(58) Field of Search ................................ 514/535, 544, 514/683; 560/20, 73, 106; 568/329

(56) References Cited

U.S. PATENT DOCUMENTS 6,140,338 A * 10/2000 Naya et al. ................. 514/299

FOREIGN PATENT DOCUMENTS

| EP | 0 934 940 A1 | 8/1999 |
| EP | 1 008 346 A1 | 6/2000 |
| EP | 1 018 514 A1 | 7/2000 |
| JP | 62-81343 | 4/1987 |
| WO | WO 00/55139 | 9/2000 |

OTHER PUBLICATIONS

Cope et al, Journal of Organic Chemistry, Cis– and Trans–1, 5–Diphenylcyclooctane, 1964, pp. 3467–3469.*

Peter Jones et al., *Zeitschrift fur Kristallographie*, 1983, 163:75–84.

Bruce Beutler et al., *Nature*, 1986, 320(17):584–588.

Tadamitsu Kishimoto, *J. of Amer. Soc. of Hermatology*, 1989, 74(1):1–10.

* cited by examiner

Primary Examiner—Paul A. Zucker
(74) Attorney, Agent, or Firm—Morgan & Finnegan, LLP.

(57) ABSTRACT

The present invention provides a compound which has cytokine production inhibitory activity and is useful for the treatment of diseases which is associated with cytokine. The compound is represented by the following general formula (I) [wherein A represents a cyclic group which may be substituted; the partial structure -D===E- represents a group represented by —$CH_2CH_2$— or —CH=CH—; W represents a group represented by —$CH_2$—, —$CH_2CH_2$—, —CH=CH— or —CH=; the partial structure >X===Y— represents a group represented by >CH—$(CH_2)_n$—, >C=CH—, >CH—$CH_2$—CH(OH)—, >CH—$CH_2$—C(=O)—, >CH—O— or >CH—O—CO—, provided that when W is —CH=, then X===Y— represents C—$(CH_2)_p$—; Z represents a divalent aliphatic hydrocarbon group; $R^1$ and $R^2$, which may be the same or different, each represents a hydrogen atom, or a hydroxyl, alkoxy or alkoxyalkoxy group; m is an integer of 0 or 1].

14 Claims, No Drawings

CYCLOOCTANONE DERIVATIVES AND CYCLODECANONE DERIVATIVE, AND USE THEREOF

TECHNICAL FIELD

The present invention relates to cyclooctane derivatives and cyclodecanone derivatives which have cytokine production inhibitory activity, and to use thereof. As used herein, cytokine refers to a proteineous factor that is released by cells and mediates intercellular communication such as the regulation of immunoresponse and inflammatory response, anti-viral and tumoral activity, the regulation of cellular proliferation and differentiation, and the like.

BACKGROUND ART

TNF-α (tumor necrosis factor), a member of cytokine family, was discovered to be a substance which has cell death inducing activity and cell proliferation inhibiting activity against tumor cells. Thereafter it has been reported that TNF-α can be produced by monocyte or macrophage stimulated by lipopolysaccharide and the like, which plays a key role in the inflammation or immunoreaction. Moreover, it has been revealed that TNF-α has a wide variety of biological activities on greatly different types of cell in addition to tumor cell, including the activation of macrophage and neutrophile, the expression of adhesive molecules in the endothelial cell, the increased proliferation of fibroblast cells, the activation of human immune deficiency virus (HIV-1) gene in CD4 positive cell and macrophage, and the like (Nature, vol. 320, 1986, pp 584–588).

IL-6, a member of cytokine family, was discovered to be a substance which promotes the differentiation of B cell into antibody producing cell without showing any effect on B cell proliferation and which is secreted in the culture supernatant of T cell stimulated with mitogen. Then, it was reported that IL-6 was produced when T cell as well as monocytes, macrophage and the like were stimuleted with cytokines such as lipopolysaccharide, TNF, IL-1 and the like. Moreover, it has been revealed that IL-6 has a wide variety of biological activities on greatly different types of cell in addition to B cell including the production of acute phase reactive protein in hepatic cell, the promotion of osteoclast bone resorption, the increase in platelet number and the like (Blood, vol. 7, 1989, pp 1–10).

IL-2, a member of cytokine family, is known as a T cell proliferation factor. IL-2 was mainly produced by T cell and to some extent by NK cell. Induced production of interferon γ in T or NK cell by IL-2 has an important rule in the formation of cytokine network.

TNF-α has been shown to be involved in the exacerbation and progression of diseased conditions including chronic rheumatoid arthritis, osteoarthritis, sepsis, Crohn's disease, diabetes mellitus, fulminant hepatitis, cachexia due to end-stage cancer and the like. IL-6 was been shown to be involved in the exacerbation and progression of diseased conditions including chronic rheumatoid arthritis, atrial myxoma, Castleman's syndrome, multiple myeloma, hyper gamma-globulinemia in present individuals with AIDS and the like. Steroids have been previously known to a substance which can inhibit TNF-α, IL-6 and IL-2. Their effects have been definitely appreciated, but there has been a problem of serious side effects following their prolonged use. Additionally, clinical applications of anti-TNF-α antibody, anti-IL-6 antibody and anti-IL-2 antibody have been investigated mainly for the treatment of chronic rheumatoid arthritis. Their effects have been appreciated, but there have been problems of the limitation that they can be used only for injection, the appearance of antibodies against anti-TNF-α antibody, anti-IL-6 antibody and anti-IL-2 antibody following continuous use leading to decreased effectiveness, expensiveness to formulate them into therapeutic drugs and the like. Therefore, it is expected that exploration of lower molecular weight compounds to inhibit the production of TNF-α, IL-6 and IL-2 results in the development of useful drugs which can be replaced for steroids and antibody formulations for the treatment of these diseases.

DISCLOSURE OF THE INVENTION

The present invention is provided in order to solve the problems described above. An object of the present invention is to provide a compound which inhibit the production of cytokine such as TNF-α, IL-6 and IL-2, and which are useful for the treatment of diseases wherein cytokine participates in including osteoarthritis, chronic rheumatoid, sepsis, cancer, ulcerative tissue and others, or salts thereof or hydrates thereof.

The present inventors studied earnestly to explore lower molecular weight compounds to inhibit cytokine production and found that substituted cyclooctanone derivatives and substituted cyclodecanone derivatives, which are represented by the following general formula (I), can inhibit cytokine production. Thus, the inventors accomplished the present invention represented by (1) to (34).

(1) A compound represented by the following general formula (I) [wherein A represents a five- to fourteen membered aromatic group, which may be substituted, or a cycloaliphatic hydrocarbon group, which may be substituted, having three to ten carbon atoms;

the partial structure -D---E- represents a group represented by —$CH_2CH_2$— or —CH=CH—;

W represents a group represented by —$CH_2$—, —$CH_2CH_2$—, —CH=CH— or —CH=;

the partial structure >X--Y— represents a group represented by the formula >CH—$(CH_2)_n$— wherein n is an integer of 0 or 1), >C=CH—, >CH—$CH_2$—CH(OH)—, >CH—$CH_2$—C(=O)—, >CH—O— or >CH—O—CO—, provided that when W is —CH=, then X--Y— represents a group represented by the formula C—$(CH_2)_p$— (wherein p is an integer of 0 or 1);

Z represents a divalent aliphatic hydrocarbon group having zero to eight carbon atoms;

$R^1$ and $R^2$, which may be the same or different, each represents a hydrogen atom, a hydroxyl group, a $C_{1-6}$ alkoxy group, or a $C_{1-6}$ alkoxy-$C_{1-6}$ alkoxy group, provided that when $R^2$ represents a hydrogen atom, then $R^1$ also represents a hydrogen atom;

m is an integer of 0 or 1, and when W represents —$CH_2$— or —CH=, then m is 0, and when W represents —$(CH_2)_2$— or —CH=CH—, then m is 1;

with exception of the compound represented by the following formula X]; or salts thereof or hydrates thereof:

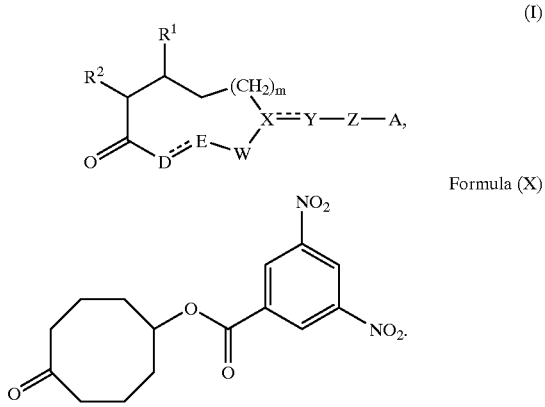

Formula (X)

(2) The compound described in the above item (1), wherein A is an aromatic hydrocarbon group having six to fourteen carbon atoms, which may be substituted; or salts thereof or hydrates thereof.

(3) The compound described in the above item (1), wherein A is a five- to fourteen-membered aromatic heterocyclic group, which may be substituted; or salts thereof or hydrates thereof.

(4) The compound described in the above item (1), wherein A is a phenyl, naphthyl, pyridyl, pyridazinyl, pyrimidinyl, pyrazinyl, thienyl, furyl, oxazolyl or thiazolyl group, each of which may be substituted; or salts thereof or hydrates thereof.

(5) The compound described in the above item (1), wherein A is a phenyl or pyridyl group, each of which may be substituted; or salts thereof or hydrates thereof.

(6) The compound described in any one of the above items (1) to (5), wherein R1 and R2 are a hydrogen atom; or salts thereof or hydrates thereof.

(7) The compound described in any one of the above items (1) to (5), wherein R2 is a hydroxyl group; or salts thereof or hydrates thereof.

(8) The compound described in any one of the above items (1) to (5), wherein R1 and/or R2 are a hydroxyl group; or salts thereof or hydrates thereof.

(9) The compound described in any one of the above items (1) to (5), wherein R1 and/or R2 are a C1–6alkoxy-C1–6alkoxy group; or salts thereof or hydrates thereof.

(10) The compound described in any one of the above items (1) to (9), wherein the partial structure -D---E- represents a group represented by —CH2CH2-; or salts thereof or hydrates thereof.

(11) The compound described in any one of the above items (1) to (9), wherein the partial structure -D---E- represents a group represented by —CH═CH—; or salts thereof or hydrates thereof.

(12) The compound described in any one of the above items (1) to (11), wherein W represents a group represented by —CH2- or —CH═, and m is 0; or salts thereof or hydrates thereof.

(13) The compound described in any one of the above items (1) to (11), wherein W represents a group represented by —CH2- and m is 0; or salts thereof or hydrates thereof.

(14) The compound described in any one of the above items (1) to (11), wherein W represents a group represented by —CH═, m is 0, and X--Y— is the formula C—(CH2)p- (wherein p is an integer of 0 or 1); or salts thereof or hydrates thereof.

(15) The compound described in any one of the above items (1) to (11), wherein W represents a group represented by —(CH2)2- or —CH═CH—, m is 1; or salts thereof or hydrates thereof.

(16) The compound described in any one of the above items (1) to (15), wherein the partial structure >X--Y— represents the formula >CH—(CH2)n- (wherein n is an integer of 0 or 1), the formula >C═CH—, the formula >CH—CH2-CH(OH)—, the formula >CH—CH2-C(═O)—, or the formula >CH—O—; or salts thereof or hydrates thereof.

(17) The compound described in any one of the above items (1) to (15), wherein the partial structure >X--Y— represents the formula >CH—(CH$_2$)$_n$— (wherein n is an integer of 0 or 1); or salts thereof or hydrates thereof.

(18) The compound described in any one of the above items (1) to (15), wherein the partial structure >X--Y— represents the formula >C═CH—; or salts thereof or hydrates thereof.

(19) The compound described in any one of the above items (1) to (15), wherein the partial structure >X--Y— represents the formula >CH—CH2-CH(OH)— or the formula >CH—CH2-C(═O)—; or salts thereof or hydrates thereof.

(20) The compound described in any one of the above items (1) to (15), wherein the partial structure >X--Y— represents the formula >CH—O— or the formula >CH—O—CO—; or salts thereof or hydrates thereof.

(21) The compound described in any one of the above items (1) to (20), wherein a substituent of the aromatic group or cycloaliphatic hydrocarbon group represented by A is a nitro group; or salts thereof or hydrates thereof.

(22) The compound described in any one of the above items (1) to (20), wherein a substituent of the aromatic group or cycloaliphatic hydrocarbon group represented by A is an alkoxy group which may be substituted; or salts thereof or hydrates thereof.

(23) The compound described in any one of the above items (1) to (20), wherein A is the aromatic group or cycloaliphatic hydrocarbon group, which may have one to three groups selected from the group consisting of a hydroxy group and an alkoxy group which may be substituted; or salts thereof or hydrates thereof.

(24) The compound described in the above items (1), wherein the compound is selected from 5-benzyl-1-cyclooctanone, 5-phenetyl-1-cyclooctanone, 5-(2-pyridylmethyl)-1-cyclooctanone, 5-[2-(2-hydroxyphenyl)ethyl]-1-cyclooctanone, 5-[2-(2-hydroxy-4-methoxyphenyl)ethyl]-1-cyclooctanone, 5-benzyl-2-cycloocten-1-one, 5-phenethyl-2-cycloocten-1-one, 5-(2-pyridylmethyl)-2-cycloocten-1-one, 5-[2-(2-hydroxy-4-methoxyphenyl)ethyl]-2-cycloocten-1-one, 5-benzyl-8-hydroxy-2-cycloocten-1-one, 5-benzyl-7,8-dihydroxy-2-cycloocten-1-one, 2,3-dihydroxy-5-[2-(2-hydroxyphenyl)ethyl]-1-cyclooctanone, 5-oxocyclooctyl benzoate, 5-oxo-3-cyclooctenyl benzoate, 5-oxocyclooctyl 2-hydroxybenzoate, 5-oxo-3-cyclooctenyl 2-hydroxybenzoate, 5-oxo-3-cyclooctenyl (2-methoxymethoxy)benzoate, 5-oxocyclooctyl (2-hydroxy-4-methoxy)benzoate, 5-oxo-3-cyclooctenyl (2-hydroxy-4-methoxy)benzoate, 5-oxo-3-cyclooctenyl 2-nitrobenzoate, 3,4-dihydroxy-5-oxocyclooctyl benzoate, 6,7-dihydroxy-5-oxo-3-cyclooctenyl benzoate, 6,7-dihydroxy-5-oxo-3-cyclooctenyl 2-hydroxybenzoate, 3,4-dihydroxy-5-oxocyclooctyl (2-methoxymethoxy)benzoate, 3,4-dihydroxy-5-oxocyclooctyl (2-hydroxy-4-methoxy)benzoate, 6,7- dihydroxy-5-oxo-3-cyclooctenyl (2-hydroxy-4-methoxy)-benzoate, 6,7-dihydroxy-5-oxo-3-cyclooctenyl 2-nitrobenzoate, 6-benzyl-1-cyclodecanone, 6-phenethyl-1-cyclodecanone, 6-(2-pyridylmethyl)-1-cyclodecanone, 6-[2-(2-hydroxyphenyl)ethyl]-1-cyclodecanone, 6-[2-(2-hydroxy-4-methoxyphenyl)ethyl]1-cyclodecanone, 6-benzyl-2-cyclodecen-1-one, 6-phenethyl-2-cyclodecen-1-one, 6-(2-pyridylmethyl)-2-cyclodecen-1-one, 6-[2-(2-hydroxy-4-methoxyphenyl)ethyl]-2-cyclodecen-1-one, 6-benzyl-10-hydroxy-2-cyclodecen-1-one, 6-benzyl-9,10-dihydroxy-2-cyclodecen-1-one, 9,10-dihydroxy-6-phenethyl-cyclodecen-1-one, 9,10-dihydroxy-6-[2-(2-hydroxyphenyl)ethyl]cyclodecen-1-one, 6-oxocyclodecyl benzoate, 6-oxo-4-cyclodecenyl benzoate, 6-oxocyclodecyl 2-hydroxybenzoate, 6-oxo-4-cyclodecenyl 2-hydroxybenzoate, 6-oxo-4-cyclodecenyl 4-methoxybenzoate, 6-oxocyclodecyl (2-hydroxy-4-methoxy)benzoate, 6-oxo-4-cyclodecenyl (2-hydroxy-4-methoxy)benzoate, 6-oxocyclodecyl 2-nitorobenzoate, 6-oxo-4-cyclodecenyl 2-nitrobenzoate, 4,5-dihydroxy-6-oxocyclodecyl benzoate, 7,8-dihydroxy-6-oxo-4-cyclodecenyl benzoate, 7,8-dihydroxy-6-oxo-4-cyclodecenyl (2-methoxymethoxy)-benzoate, 7,8-dihydroxy-6-oxo-4-cyclodecenyl 4-methoxybenzoate, 7,8-dihydroxy-6-oxo-4-cyclodecenyl (2-hydroxy-4-methoxy)-benzoate, 4,5-dihydroxy-6-oxocyclodecyl 2-nitrobenzoate, 7,8-dihydroxy-6-oxo-4-cyclodecenyl 2-nitrobenzoate; or salts thereof or hydrates thereof.

(25) A pharmaceutical composition comprising the compound described in any one of the above items (1) to (24), or salts thereof or hydrates thereof.

(26) An agent for inhibiting cytokine production, comprising the compound described in any one of the above items (1) to (24).

(27) An agent for inhibiting TNF-α production, IL-6 production or IL-2 production, comprising the compound described in any one of the above items (1) to (24).

(28) An agent for treating or preventing diseases which is associated with cytokine, comprising the compound described in any one of the above items (1) to (24).

(29) An agent for treating or preventing chronic rheumatoid arthritis, ulcerative colitis, glomerulonephritis, osteoarthritis, atopic dermatitis, endotoxin shock, sepsis, diabetes, viral hepatitis, mesangial proliferative glomerulonephritis, adenoviral ophthalmia or AIDS, which is associated with cytokine, wherein the agent comprises the compound described in any one of the above items (1) to (24).

(30) A pharmaceutical composition comprising a compound represented by the following general formula (I) [wherein A represents a six- to fourteen membered aromatic group, which may be substituted, or a cycloaliphatic hydrocarbon group, which may be substituted, having three to ten carbon atoms;

the partial structure -D---E- represents a group represented by —CH2CH2- or —CH=CH—;

W represents a group represented by —CH2-, —CH2CH2-, —CH=CH— or —CH=;

the partial structure >X--Y— represents a group represented by the formula >CH—(CH2)n- (wherein n is an integer of 0 or 1), >C=CH—, >CH—CH2-CH(OH)—, >CH—CH2-C(=O)—, >CH—O— or >CH—O—CO—, provided that when W is —CH=, then X--Y— represents a group represented by the formula C—(CH2)p- (wherein p is an integer of 0 or 1);

Z represents a divalent aliphatic hydrocarbon group having zero to eight carbon atoms;

R1 and R2, which may be the same or different, each represents a hydrogen atom, a hydroxyl group, a C1–6 alkoxy group, or a C1–6 alkoxy-C1–6 alkoxy group, provided that when R2 represents a hydrogen atom, then R1 also represents a hydrogen atom;

m is an integer of 0 or 1, and when W represents —CH2- or —CH=, then m is 0, and when W represents —(CH2)2- or —CH=CH—, then m is 1;

with exception of the compound represented by the following formula X]; or salts thereof or hydrates thereof:

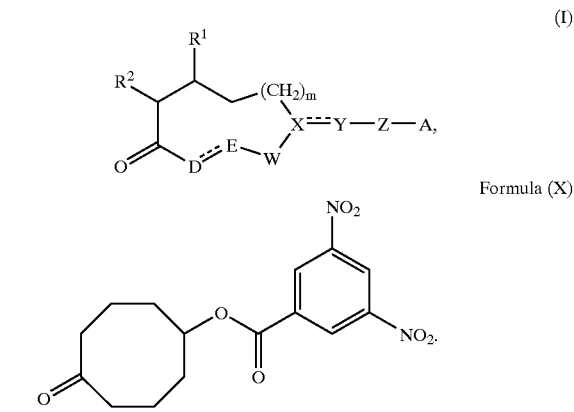

(31) The pharmaceutical composition described in the above item (30), wherein the pharmaceutical composition is an agent for inhibiting cytokine production.

(32) The pharmaceutical composition described in the above item (30), wherein the pharmaceutical composition is an agent for inhibiting TNF-α production, IL-6 production or IL-2 production.

(33) The pharmaceutical composition described in the above item (30), wherein the pharmaceutical composition is an agent for treating or preventing diseases which is associated with cytokine.

(34) The pharmaceutical composition described in the above item (30), wherein the pharmaceutical composition is an agent for treating or preventing chronic rheumatoid arthritis, ulcerative colitis, glomerulonephritis, osteoarthritis, atopic dermatitis, endotoxin shock, sepsis, diabetes, viral hepatitis, mesangial proliferative glomerulonephritis, adenoviral ophthalmia or AIDS, which are deseases associated with cytokine.

PREFERRED EMBODIMENTS FOR CARRYING OUT THE INVENTION

The present invention is described in detail hereinafter. The signs, terms and the like as used herein means as follows:

Herein the structural formula of a compound represents conveniently a certain form of isomer, but a compound of the present invention may include any form of isomers and mixture of isomers such as geometrical isomers, optical isomers based on asymmetric carbon(s), stereoisomers, interchangeable isomers and the like. The present compound is not limited to the compound defined by the structure described conveniently and may be either of anyone of isomers or mixture of isomers. Thus, the present compound can be optically active compound having asymmetric carbon (s) or racemate thereof. The present invention may include, but is not limited to, any form of the present compound. The present compound may have polymorphism and may include, but is not limited to, any crystal form. The present compound may be single crystal form or mixture of crystal forms, or anhydrous or hydrated. In addition, so-called metabolites, which are produced by the breakdown of the compounds according to the present invention in the body, are included within the scope of the present invention.

The term "and/or" as used herein is used to mean both "and" and "or". Thus, for example, the term "A and/or B" can include both or either "A and B" or "A or B".

Diseases, which are associated with cytokine, may include, for example, autoimmune diseases including chronic rheumatoid arthritis, systemic lupus erythematosus, scleroderma, Bechet's disease, periarteritis nodosa, ulcerative colitis, active chronic hepatitis, glomerulonephritis and the like; a large variety of intractable diseases whose pathology is based on inflammatory symptoms including osteoarthritis, gout, atherosclerosis, psoriasis, atopic dermatitis, pulmonary disease accompanied by granuloma, a variety of encephalitis and the like; endotoxin shock, sepsis, inflammatory colitis, diabetes mellitus, acute myeloblastic leukemia, pneumonia, a heart transplantation, encephalomyelitis, anorexia, acute hepatitis, chronic hepatitis, drug-induced hepatopathy, alcoholic hepatitis, viral hepatitis, jaundice, cirrhosis, hepatic insufficiency, atrial myxoma, Castleman's syndrome, multiple myeloma, Lennert's T lymphoma, mesangial proliferative nephritis, renal cell carcinoma, cytomegaloviral pneumonia, cytomegaloviral retinopathy, adenoviral cold, adenoviral pharyngoconjunctival fever, adenoviral ophthalmia, AIDS and the like.

Description of Aromatic Group

The term "aromatic" of the aromatic group, which may be substituted, represented by A refers to a carbocyclic compound or derivatives thereof having aromatic property. The term aromatic property herein refers to the properties which arise physically because the molecule is stabilized due to the delocalization of the π electrons over the ring and chemically because the ring is susceptible to substitution by addition. Typical examples of the aromatic groups may include, for example, (A) aromatic hydrocarbon group and (B) aromatic heterocyclic group. Preferably, the aromatic group, which may be substituted, represented by A may be one having three to fourteen carbon atoms.

(A) Aromatic hydrocarbon group means the general term for the residual groups wherein a hydrogen atom is removed from the nucleus of aromatic hydrocarbon. A monocyclic or aromatic condensed multicyclic group having six to fourteen carbon atoms is preferable. Examples of aromatic hydrocarbon groups described above may include phenyl, naphthyl (α-naphthyl, β-naphthyl), 1-indanyl, 2-indanyl, 4-indanyl, 5-indanyl, 1-indenyl, 2-indenyl, 4-indenyl, 5-indenyl, 1,2,3,4-tetrahydro-1-naphthyl, 5,6,7,8-tetrahydro-1-naphthyl, 1,2,3,4-tetrahydro-2-naphthyl, 5,6,7,8-tetrahydro-2-naphthyl, 1,2-dihydro-1-naphthyl, 1,4-dihydro-1-naphthyl, 3,4-dihydro-1-naphthyl, 5,6-dihydro-1-naphthyl, 1,2-dihydro-2-naphthyl, 1,4-dihydro-2-naphthyl, 3,4-dihydro-2-naphthyl, 5,6-dihydro-2-naphthyl, 5,6-dihydro-3-naphthyl, 5,6-dihydro-4-naphthyl. A phenyl or naphthyl group is particularly preferable.

(B) The term "aromatic heterocyclic" in the aromatic heterocyclic group refers to a cyclic compound having aromatic properties, which contains, in addition to carbon atom, heteroatom(s) selected from oxygen, sulfur and nitrogen atoms as atom(s) forming the ring. Particularly a monocyclic ((1)) or bicyclic ((2)) aromatic compound is preferable having, in addition to carbon atom, one to five heteroatoms selected from oxygen, sulfur and nitrogen atoms as a atom forming the ring.

(1) A monocyclic aromatic heterocyclic group may be a five- to seven-membered monocyclic heteroaromatic group having, in addition to carbon atom, one to four heteroatoms selected from oxygen, sulfur and nitrogen atoms as atom forming the ring, preferably. Examples of these monocyclic heteroaromatic group may include, for example, furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidyl, pyrazinyl, triazynyl groups and the like. A particularly preferable monocyclic heteroaromatic group may be a five- to six-membered ring group having one to three heteroatoms selected from oxygen, sulfur and nitrogen atoms, including pyridyl, pyridazinyl, pyrimidyl, pyrazinyl, thienyl, furyl, oxazolyl, thiazolyl groups and the like.

(2) A bicyclic aromatic heterocyclic group means a group wherein two adjacent rings are condensed together via two atoms shared by them to constitute a condensed ring moiety, in particular a condensed bicyclic aromatic heterocyclic group. Examples of condensed bicyclic aromatic heterocyclic group may include a group wherein one ring moiety is carbocyclic and another ring moiety is heterocyclic, or a group wherein both ring moieties are heterocyclic. Preferably, the former, carbocycle, may be a group having six to ten carbon atoms and the latter may be a five- to seven-membered monocyclic aromatic heterocyclic group having, in addition to carbon atom, one to three heteroatoms selected from oxygen, sulfur and nitrogen atoms. Examples of these condensed bicyclic aromatic heterocyclic group may include, for example, benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzothiazolyl, 1H-benzotriazolyl, quinolyl, isoquinolyl, cinnolinyl, quinazolinyl, quinoxalinyl, phthalazinyl, naphthylizinyl, purinyl, pteridinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl groups and the like.

Description of Alicyclic Hydrocarbon Group

The term "alicyclic hydrocarbon" in the phrase "alicyclic hydrocarbon group, which may be substituted, represented by A" refers to a compound having no aromatic properties wherein all the atoms forming the ring are carbon atom. Preferably, the alicyclic hydrocarbonn group may be a saturated or unsaturated alicyclic hydrocarbon group having three to ten carbon atoms. Particularly, (1) a cycloalkyl group having three to seven carbon atoms, (2) a cycloalkenyl group having three to seven carbon atoms, and (3) a cycloalkadienyl group having four to seven carbon atoms are preferable.

(1) Examples of cycloalkyl groups may include, for example, cyclopropyl, cyclobutyl, cyclopentyl, cyclohexyl, cycloheptyl groups and the like. (2).Examples of cycloalkenyl groups may include, for example, cyclobutenyl, 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl groups and the like. (3) Examples of cycloalkadienyl groups may include, for example, 2,4-cyclopentadienyl, 2,4- cyclohexadienyl, 2,5-cyclohexadienyl, 2,4-cycloheptadienyl groups and the like.

Description of Substituents in Aromatic and Alicyclic Hydrocarbon Groups

In the general formula (I), aromatic and alicyclic hydrocarbon groups represented by A may have one to five substituents, preferably one to three substituents at the substitutable positions. Examples of substituents described above may include, for example, (a) an aliphatic hydrocarbon group, (b) an alicyclic hydrocarbon group, (c) an aryl group, (d) an aralkyl group, (e) a heteroaromatic group, (f) a non-aromatic heterocyclic group, (g) halogen atoms, (h) a nitro group (—$NO_2$), (i) a nitroso group (—NO), (j) an amino group which may be substituted, (k) an amidino group (—(HN═)C.$NH_2$), (l) an acyl group, (m) a carbamoyl group which may be substituted, (n) a sulfamoyl group which may be substituted, (o) a carboxy group (—COOH), (p) a carboxy group which may be esterificated, (q) a hydroxyl group (—OH), (r) a hydroxyl group which may be substituted, (s) an alkoxy group which may be substituted, (t) a mercapto group (—SH), (u) a thiol group which may be substituted, (v) a sulfinyl group which may be substituted, (w) a sulfonyl group which may be substituted, (x) a sulfo group (—$SO_2$)(OH), (y) a cyano group (C≡N), (z) an azido group(—$N_3$).

(a) Aliphatic Hydrocarbon Group

Aliphatic hydrocarbon described in the term "aliphatic hydrocarbon group" refers to a compound consisting of carbon and hydrogen atoms in linear strand. An aliphatic hydrocarbon group is preferably an aliphatic linear or branched hydrocarbon group having one to ten carbon atoms. Particularly, (1) an alkyl group having one to six carbon atoms, (2) an alkenyl group having two to six carbon atoms, (3) an alkynyl group group having two to six carbon atoms. Examples of (1) alkyl groups may include, for example, methyl, ethyl, propyl, isopropyl, butyl, isobutyl, sec-butyl, t-butyl, pentyl, isopentyl, neopentyl, t-pentyl, 1-ethylpropyl, hexyl, ixohexyl, 1,1-dimethylbutyl, 2,2-dimethylbutyl, 3,3-dimethylbutyl, 2-ethylbutyl groups and the like. Examples of (2) alkenyl groups may include, for example, vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl groups and the like. Examples of (3) alkynyl groups may include, for example, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl groups and the like.

(b) Cycloaliphatic Hydrocarbon Group

Cycloaliphatic hydrocarbon described in the term "cycloaliphatic hydrocarbon group" is as forementioned. An cycloaliphatic hydrocarbon group is preferably a saturated or unsaturated cycloaliphatic hydrocarbon group having three to ten carbon atoms. Particularly, (1) an cycloalkyl group having three to seven carbon atoms, (2) an cycloalkenyl group having three to seven carbon atoms, (3) an cycloalkadienyl group having five to seven carbon atoms and the like are preferable. Examples of (1) cycloalkyl groups may include cyclopropyl, cyclobutyl, cyclopentyl, cyclohexyl, cycloheptyl and the like. Examples of cycloalkenyl group may include 2-cyclopentenyl, 3-cyclopentenyl, 2-cyclohexenyl, 3-cyclohexenyl and the like. Examples of (3) cycloalkadienyl group may include 2,4-cyclopentadienyl, 2,4-cyclohexadienyl, 2,5-cyclohexadienyl and the like.

(c) Aryl Group

An aryl group refers to the general term for the group generated by removing a hydrogen atom attached to aromatic hydrocarbon ring. Preferably, the aryl group may be an aryl group having six to ten carbon atoms. Examples of the aryl group may include phenyl, naphthyl, indanyl, indenyl, 5,6,7,8-tetrahydro-1-naphthyl, 5,6,7,8-tetrahydro-2-naphthyl, 5,6-dihydro-1-naphthyl, 5,6-dihydro-2-naphthyl, 5,6-dihydro-3-naphthyl, 5,6-dihydro-4-naphthyl. Phenyl, α-naphthyl, or β-naphthyl is preferable among others.

(d) Aralkyl Group

An aralkyl group refers to the group wherein a hydrogen atom in alkyl group is replaced for an aryl group. Aralkyl group wherein a hydrogen atom in a linear or branched alkyl group having one to four carbon atoms is replaced for an aryl group having six to ten carbon atoms is preferable. Examples of the aralkyl group may include benzyl, phenethyl, 1-phenylethyl, 2-phenylethyl, α-naphthylmethyl, β-naphthylmethyl, α-naphthylethyl, β-naphthylethyl, 1-phenylpropyl, 2-phenylpropyl, 3-phenylpropyl, 4-phenylbutyl and the like. 2-Phenylethyl is preferable among others.

(e) A Heteroaromatic group is as forementioned. For its substituents, furyl, thienyl pyrrolyl and oxazolyl are preferable (f) Non-Aromatic Heterocyclic Group Non-aromatic heterocyclic described in the term "non-aromatic heterocyclic group" refers to a cyclic compound having no aromatic properties wherein the compound contains, in addition to carbon atom, heteroatom(s) selected from oxygen, sulfur and nitrogen atoms as an atom forming the ring. Preferably, the non-aromatic heterocyclic group may be a four- to seven-membered non-aromatic heterocyclic group containing one to three heteroatoms selected from oxygen, sulfur and nitrogen atoms. Examples of the non-aromatic heterocyclic group may include azetidinyl, oxetanyl, thietanyl, pyrrolidinyl, tetrahydrofuryl, thiolanyl, piperidyl, tetrahydropyranyl, morpholinyl, thiomorpholinyl, piperazinyl and the like.

(g) Examples of halogen atoms may include fluorine, chlorine, bromine and iodine, fluorine and chlorine being particularly preferable (i) Amino Group An amino group which may be substituted refers to an amino group (—$NH_2$) or an amino group whose substitutable position is substituted. Preferably, the substituted amino group may be an amino group whose substitutable position is mono- or di-substituted with an alkyl group having one to six carbon atoms, a cycloalkyl group having three to seven carbon atoms, an alkenyl group having two to six carbon atoms, a cycloalkenyl group having three to seven carbon atoms, or an aryl group having six to ten carbon atoms. Examples of the substituted amino group may include methylamino, dimethylamino, ethylamino, diethylamino, allylamino, diallylamino, dibutylamino, cyclohexylamino, propionylamino, benzoylamino, phenylamino, N-methyl-N-phenylamino and the like. Dimethylamino is particularly preferable.

(l) Acyl Group

An acyl group refers to the general term for RCO— group. Preferably, the acyl group may be a group wherein a carbonyl group is linked with either of an alkyl group having one to eight carbon atoms, a cycloalkyl group having three to seven carbon atoms, an alkenyl group having two to eight carbon atoms, a cycloalkenyl group having three to seven carbon atoms, an aryl group having six to ten carbon atoms, or an aromatic heterocyclic group (e.g., thienyl, furyl, pyridyl and the like). Examples of the acyl group may include acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptancarbonyl, crotonyl, 2-cyclohexenecarbonyl, benzoyl, nicotinoyl and the like. Acetyl is particularly preferable.

(m) Carbamoyl Group

The term "carbamoyl group which may be substituted" refers to a carbamoyl group (—CONH$_2$) and a carbamoyl group whose substitutable position is substituted. Preferably, the substituted carbamoyl group may be carbamoyl group whose substitutable position is mono- or di-substituted with an alkyl group having one to six carbon atoms, a cycloalkyl group having three to seven carbon atoms, an alkenyl group having two to six carbon atoms, a cycloalkenyl group having three to seven carbon atoms or an aryl group having six to ten carbon atoms. Examples of the carbamoyl group may include methylcarbamoyl, ethylcarbamoyl, dimethylcarbamoyl, diethylcarbamoyl, diallylcarbamoyl, dibutylcarbamoyl, propionylcarbamoyl, benzoylcarbamoyl, N-methyl-N-phenylcarbamoyl, cyclohexylcarbamoyl, phenylcarbamoyl and the like.

(n) Sulfamoyl Group

The term "sulfamoyl group which may be substituted" refers to a sulfamoyl group (—SO$_2$NH$_2$) and a sulfamoyl group whose substitutable position is substituted. Preferably, the substituted sulfamoyl group may be a sulfamoyl group whose substitutable position is mono- or di-substituted with an alkyl group having one to six carbon atoms, a cycloalkyl group having three to seven carbon atoms, an alkenyl group having two to six carbon atoms, a cycloalkenyl group having three to seven carbon atoms or an aryl group having six to ten carbon atoms. Examples of the substituted sulfamoyl group may include methylsulfamoyl, ethylsulfamoyl, dimethylsulfamoyl, diethylsulfamoyl, cyclohexylsulfamoyl, phenylsulfamoyl, diallylsulfamoyl, dibutylsulfamoyl, propionylsulfamoyl, benzoylsulfamoyl, N-methyl-N-phenylsulfamoyl and the like.

(p) Carboxy Group

The term "carboxy group which may be esterificated" refers to a carboxy group (—COOH) and a carboxy group whose hydrogen atom is esterificated. Preferably, the esterificated carboxy group may be an alkoxy-carbonyl group having one to six carbon atoms. Examples of the alkoxy-carbonyl group may include methoxycarbonyl, ethoxycarbonyl, propoxycarbonyl, butoxycarbonyl, isobutoxycarbonyl, sec.-butoxycarbonyl, t.-butoxycarbonyl, pentyloxycarbonyl, isopentyloxycarbonyl, neopentyloxycarbonyl, hexyloxycarbonyl and the like.

(r) Hydroxyl Group

The term "hydroxy group which may be substituted" refers to a hydroxy group (—OH) and a hydroxy group whose substitutable position is substituted. Preferably, the substituted hydroxy group may be (1) an alkoxy group having one to six carbon atoms, (2) an alkenyloxy group having two to six carbon atoms, (3) a cycloalkyloxy group having three to seven carbon atoms, (4) a cycloalkenyloxy group having three to seven carbon atoms, (5) an aralkyloxy group having seven to fourteen carbon atoms, (6) an acyloxy group having two to four carbon atoms, (7) an aryloxy group having six to ten carbon atoms and the like. Examples of (1) alkoxy groups may include methoxy, ethoxy, propoxy, isopropoxy, butoxy, isobutoxy, sec.-butoxy, t.-butoxy, pentyloxy, isopentyloxy, neopentyloxy, hexyloxy. Examples of (2) alkenyloxy groups may include allyloxy, 2-butenyloxy, 2-pentenyloxy, 3-hexenyloxy and the like. Examples of (3) cycloalkyloxy groups may include cyclopropionyloxy, cyclobutyloxy, cyclopentyloxy, cyclohexyloxy, cycloheptyloxy and the like. Examples of (4) cycloalkenyloxy groups may include cyclopropenyloxy, cyclobutenyloxy, cyclopentenyloxy, cyclohexenyloxy, cycloheptenyloxy and the like. Examples of (5) aralkyloxy groups may include benzyloxy, phenetyloxy and the like. Examples of (6) acyloxy groups may include acetyloxy, propionyloxy, butyryloxy, isobutyryloxy and the like. Examples of (7) aryloxy groups may include phenoxy, naphthyloxy and the like. Preferably, the substituted hydroxy group may be methoxy or ethoxy.

(s) Alkoxy Group

An alkoxy group described in the term "alkoxy group which may be substitued" refers to the general term for RO— group wherein R is hydrocarbon. A substituted alkoxy group refers to an alkoxy group which has sustituent(s) at the substitutable position. Preferably, the substituents may be an alkyl group having one to ten carbon atoms, a cycloalkyl group having three to ten carbon atoms, an alkenyl group having two to ten carbon atoms, a cycloalkenyl group having three to ten carbon atoms, an alkoxy group having one to six carbon atoms, an acyl group having two to ten carbon atoms (e.g., alkanoyl group having two to eight carbon atoms, arylcarbonyl group having six to ten carbon atoms) or an aryl group having six to ten carbon atoms and the like. More preferably, the substituted alkoxy group may be $C_{1-4}$alkoxy$C_{1-4}$alkoxy group. Examples of the $C_{1-4}$alkoxy$C_{1-4}$alkoxy group may be linear or branched and include, for example, methoxymethoxy, methoxyethoxy (1-methoxyethoxy, 2-methoxyethoxy), methoxypropoxy, methoxybutoxy, ethoxymethoxy, ethoxyethoxy, ethoxypropoxy, ethoxybutoxy, propoxymethoxy, propoxyethoxy, propoxypropoxy, propoxybutoxy, butoxymethoxy, butoxyethoxy, butoxypropoxy, butoxybutoxy. Methoxymethoxy is particularly preferable among others.

(u) Thiol Group

A thiol group which may be substituted refers to a thiol group and a thiol group whose substitutable position is substituted. Preferably, the substituted thiol group may be (1) an alkylthio group having one to six carbon atoms, (2) an alkenylthio group having two to six carbon atoms, (3) a cykloalkylthio group having three to ten carbon atoms, (4) a cycloalkenylthio group having three to seven carbon atoms, (5) an aralkylthio group having seven to fourteen carbon atoms, (6) an acylthio group having two to four carbon atoms, (7) an arylthio group having six to ten carbon atoms. Examples of (1) alkylthio groups may include methylthio, ethylthio, propylthio, isopropylthio, butylthio, isobutylthio, sec.-butylthio, t-butylthio, pentylthio, isopentylthio, neopentylthio, hexylthio and the like. Examples of (2) alkenylthio groups may include allylthio, 2-butenylthio, 2-pentenylthio, 3-hexenylthio and the like. Example of (3) cycloalkylthio groups may include cyclobutylthio, cyclopentylthio, cyclohexlthio and the like. Examples of (4) cycloalkenylthio groups may include cyclopropenylthio, cyclobutenylthio, cyclopentenylthio, cyclohexenylthio, cycloheptenylthio and the like. Examples of (5) aralkylthio groups may include benzylthio, phenetylthio and the like. Examples of (6) acylthio group may include acetylthio, propionylthio, butyrylthio, isobutyrylthio and the like. Examples of (7) arylthio groups may include phenylthio, naphthylthio and the like. Particular preferably, the substituted thiol group may be methylthio.

(v) Sulfinyl Group

A sufinyl group which may be substituted refers to a sulfinyl group (—SO—) and a sufinyl group which contains substituent(s) at the substitutable position. Preferably, the substituents may be (1) an alkyl group having one to six carbon atoms, (2) a cycloalkyl group having three to seven carbon atoms, (3) a cycloalkenyl group having three to seven carbon atoms, (4) an aryl group having six to ten carbon atoms, or (5) an aralkyl group having seven to fourteen carbon atoms. Examples of (1) alkylsulfinyl groups may include methylsulfinyl, ethylsulfinyl, dimethylsulfinyl, diethylsulfinyl and the like. Examples of (2) cycloalkylsulfinyl groups may include cyclobutylsulfinyl, cyclopentylsulfinyl, cyclohexylsulfinyl and the like. Examples of (3) cycloalkenylsulfinyl groups may include cyclobutenylsulfinyl, cyclopentenylsulfinyl, cyclohexenylsulfinyl, cycloheptenylsulfinyl and the like. Examples of (4) arylsulfinyl groups may include phenylsulfinyl, 1-naphthylsulfinyl, 2-naphthylsulfinyl and the like. Examples of (5) aralkylsulfinyl groups may include benzylsulfinyl, phenetylsulfinyl and the like. Particular preferably, the substituted sulfinyl group may be methysulfinyl group or benzylsulfinyl group.

(w) Sulfonyl Group

A sulfonyl group which may be substituted refers to a sulfonyl group (—SO$_2$—) and a sulfonyl group which contains substituent(s) at the substitutable position. Preferably, the substituents may be (1) an alkyl group having one to six carbon atoms, (2) a cycloalkyl group having three to seven carbon atoms, (3) a cycloalkenyl group having three to seven carbon atoms, (4) an aralkyl group having seven to fourteen carbon atoms, or (5) an aryl group having six to ten carbon atoms. Examples of (1) alkylsulfonyl groups may include methylsulfonyl, ethylsulfonyl, dimethylsulfonyl, diethylsulfonyl, propylsulfonyl, isopropylsulfonyl, butylsulfonyl, isobutylsulfonyl, sec.-butylsulfonyl, t.-butylsulfonyl, pentylsulfonyl, isopentylsulfonyl, neopentylsulfonyl, hexylsulfonyl and the like. Examples of (2) cycloalkylsulfonyl groups may include cyclobutylsulfonyl, cyclopentylsulfonyl, cyclohexylsulfonyl and the like. Examples of (3) cycloalkenylsulfonyl groups may include cyclobutenylsulfonyl, cyclopentenylsulfonyl, cyclohexenylsulfonyl, cycloheputenylsulfonyl and the like. Examples of (4) aralkylsulfonyl groups may include benzylsulfonyl, phenetylsulfonyl and the like. Examples of (5) arylsulfonyl groups may include phenylsulfonyl, 1-naphthylsulfonyl, 2-naphthylsulfonyl and the like. Particular preferably, the substituted sulfonyl group may be methylsulfonyl or benzylsulfonyl.

Examples of most suitable aromatic and alicyclic hydrocarbon group may include a $C_{1-6}$ alkoxy group, a $C_{1-4}$ alkoxy-$C_{1-4}$ alkoxy group, a hydroxyl group, and a nitro group, provided that nitro group is preferably used, if in the formula (I), W represents —(CH$_2$)$_2$— or —CH═CH— and m is 1 and the number of substituent is 1.

When in the general formula (I), the substituent(s) in aromatic and alicyclic hydrocarbon group represented by A is (a) the aliphatic hydrocarbon group, (b)the alicyclic hydrocarbon group, (c) the aryl group, (d) the aralkyl group, (e) the aryl heterocyclic group, (f) the non-aromatic heterocyclic group, it may contain one to three substituents-[1] described below at the substitutable position.

In the substituent in the aromatic or alicyclic hydrocarbon group reperesented by A, the following aryl group or the following aromatic heterocyclic group may further have one to three substituents-[2] described below at the substitutable position:

(1) an aryl group in amino group substituted with an aryl group, in a carbamoyl group substituted with an aryl group, in a sulfamoyl group substituted with an aryl group, in a hydroxy group substituted with an aryl group, in an alkoxy group substituted with an aryl group, in a thiol group substituted with an aryl group, in a sulfinyl group substituted with an aryl group, or in a sulfonyl group substituted with an aryl group;

(2) an aryl group in a hydroxy group substituted with an aralkyl group, in a thio group substituted with an aralkyl group, or in a sulfinyl group substituted with an aralkyl group; (3) an aryl group in an arkoxy group substituted with an arylcarbonyl group; (4) an aryl group in an acyl group combined with an aryl group and a carbonyl group, or an aromatic heterocyclic group in an acyl group combiend with an aromatic heterocycle and a carbonyl group.

Examples of the substituents [1] and [2] may include an alkyl group having one to six carbon atoms (e.g., methyl, ethyl, propyl), an amino group which may be substituted with an alkyl group having one to six carbon atoms (e.g., methylamino, dimethylamino, ethylamino, diethylamino), an amidino group, a carbamoyl group which may be substituted with an alkyl group having one to six carbon atoms (e.g., methylcarbamoyl, ethylcarbamoyl, dimethylcarbamoyl, diethylcarbamoyl), a sulfamoyl group which may be substituted with an alkyl group having one to six carbon atoms (e.g., methylsulfamoyl, ethylsulfamoyl, dimethylsulfamoyl, diethylsulfamoyl), a carboxy group, an alkoxycarbonyl group having two to seven carbon atoms (e.g., ethoxycarbonyl, propoxycarbonyl), a hydroxy group, an alkoxy group having one to six carbon atoms (e.g., methoxy, ethoxy, propoxy), a mercapto group, an alkylthio group having one to six carbon atoms (e.g., methylthio, ethylthio, propylthio), a sulfo group, a cyano group, an azide group, a halogen group, a nitro group, a nitroso group and the like.

Description of $R^1$ and $R^2$

In the general formula (I), $R^1$ and $R^2$ which may be the same or different, each represents (a) a hydrogen atom, (b) a hydroxyl group, (c) a $C_{1-6}$ alkoxy group, or (d) a $C_{1-6}$ alkoxy-$C_{1-6}$ alkoxy group, and when $R^2$ represents a hydrogen atom, then $R^1$ also represents a hydrogen atom.

Examples of (c) $C_{1-6}$ alkoxy group may include methoxy, ethoxy, propoxy, isopropoxy, butoxy, isobutoxy, sec.-butoxy, t.-butoxy, pentyloxy, isopentyloxy, neopentyloxy, hexyloxy and the like. Particularly preferable examples may include methoxy and ethoxy.

(d) The $C_{1-6}$ alkoxy-$C_{1-6}$ alkoxy group may be linear or branched, and example thereof may include, for example, methoxymethoxy, methoxyethoxy (1-methoxyethoxy, 2-methoxyethoxy), methoxypropoxy, methoxybutoxy, methoxypentyloxy, methoxyhexyloxy, ethoxymethoxy, ethoxyethoxy, ethoxypropoxy, ethoxybutoxy, ethoxypentyloxy, ethoxyhexyloxy, propoxymethoxy, propoxyethoxy, propoxypropoxy, propoxybutoxy, propoxypentyloxy, propoxyhexyloxy, butoxymethoxy, butoxyethoxy, butoxypropoxy, butoxybutoxy, butoxypentyloxy, butoxyhexyloxy, pentyloxymethoxy, pentyloxyethoxy, pentyloxypropoxy, pentyloxypbutoxy, pentyloxypentyloxy, pentyloxyhexyloxy, hexyloxymethoxy, hexyloxyethoxy, hexyloxyprpoxy, hexyloxybutoxy, hexyloxypentyloxy, hexyloxyhexyloxy and the like. Suitable examples may include methoxymethoxy and methoxyethoxy.

Description of Z

In the general formula (I), Z represents divalent aliphatic hydrocarbon group having zero to eight carbon atoms, In the case that "the number of carbon atom is zero" means that Z is a single bond. The aliphatic hydrocarbon may be linear or branched, and may be saturated or unsaturated. Examples thereof may include saturated hydrocarbon groups such as —CH$_2$—, —CH(CH$_3$)—, —(CH$_2$)$_2$—, —CH(C$_2$H$_5$)—, —(CH$_2$)$_3$—, —(CH$_2$)$_4$—, —(CH$_2$)$_5$— and —(CH$_2$)$_6$—; and unsaturated hydrocarbon groups such as —CH=CH—, —C(CH$_3$)=CH—, —CH=CH—CH$_2$—, —C(C$_2$H$_5$)=CH—, —CH$_2$—CH=CH—CH$_2$—, —CH$_2$—CH$_2$—CH=CH—CH$_2$— and —CH=CH—CH=CH—CH$_2$—. Z is preferably aliphatic hydrocarbon groups having one to three carbon atoms, and the aliphatic hydrogen group is preferably saturated.

The present compound represented by the general formula (I) may have stereoisomer or opticalisomer depending on the type of the substituent(s). Each of isomers and mixture thereof are encompassed within the scope of the present invention.

Description of Pharmaceutically Acceptable Salt

Salts of the compounds represented by the general formula (I) may be preferably pharmaceutically acceptable salts. Examples thereof may include (1) salts with inorganic bases, (2) salts with organic bases, (3) salts with inorganic acids, (4) salts with organic acids, (5) salts with basic amino acids or (6) salts with acidic amino acids and the like.

Suitable examples of (1) salts with inorganic bases may include alkali metal salt such as sodium salt and potassium salt; alkaline earth metal salt such as calcium salt and magnesium salt; and aluminum salt, ammonium salt and the like. Suitable examples of (2) salts with organic bases may include salts with trimethylamine, triethylamine, pyridine, ethanolamine, diethanolamine, triethanolamine, dicyclohexylamine and the like. Suitable examples of (3) salts with inorganic acids may include salts with hydrochloric acid, hydrobromic acid, nitric acid, sulfuric acid, phosphoric acid and the like. Suitable examples of (4) salts with organic acids may include salts with acetic acid, trifluoroacetic acid, flumaric acid, oxalic acid, tartaric acid, maleic acid, citric acid, succinic acid, malic acid, methanesulfonic acid, p-toluenesulfonic acid and the like. Suitable examples of (5) salts with basic amino acids may include salts with arginine, lysin, omithine and the like. Suitable examples of (6) salts with acidic amino acids may include salts with aspartic acid, glutamic acid and the like. Salts of the compounds represented by the general formula (I) encompasses hydrates of the compounds represented by the general formula (I).

Description of Dosage Form

The present compound represented by the general formula (I) or salts thereof can be administered alone or in combination with pharmaceutically acceptable carrier orally or parenterally as solid preparation such as tablet, capsule, granule or powder; liquid preparation such as syrup, infusion or injection; suppository, or external preparation. The present compound represented by the general formula (I) or salts thereof can be formulated according to the well-known method, such that the preparation usually contains 0.5 to 100% (w/w) of the present compound or salts thereof based on the total weight of the preparation. The tablet and granule can be optionally coated with sugar coating, gelatin coating and others if desired.

For pharmaceutically acceptable carrier, a variety of organic or inorganic carrier substances can be used and blended as (a) an excipient, (b) a lubricant, (c) a binder, and (d) a disintegrating agent in solid preparation; and (e) solvent, (f) co-solvent, (g) a suspending agent, (h) an isotonizing agent, (i) a buffering agent, (j) a soothing agent, and (k) a stabilizing agent in liquid preparation. Optionally additives can be used including (l) preservative, (m) antioxidantal agent, (n) flavoring agent, coloring agent, sweetening agent and the like.

Suitable examples of (a) the excipient may include, for example, lactose, sucrose, D-mannitol, starch, crystalline cellulose, light anhydrous silicic acid, cornstarch, glucose, sorbitol, silicon dioxide and the like. Suitable examples of (b) the lubricant may include, for example, magnesium stearate, calcium stearate, talc, colloidal silica, polyethylene glycol, hydrogenated vegetable oil and the like. Suitable examples of (c) the binder may include, for example, crystalline cellulose, sucrose, D-mannitol, dextrin, hydroxypropylcellulose, hydroxypropylmethylcellulose, polyvinylpyrrolidone, polyvinylalcohol, polyvinylether, arabic gum, tragacanth, gelatin, shellac, calcium citrate, pectin and the like. Suitable examples of (d) the disintegrating agent may include, for example, starch, carboxymethylcellulose, calcium carboxymethylcellulose, gulose-carmellose sodium, sodium carboxymethylstarch and the like.

Suitable examples of (e) the solvent may include, for example, water for injection, ethanol, propyleneglycol, macrogol, sesame oil, corn oil and the like. Examples of (f) the co-solvent may include, for example, polyethyleneglycol, propyleneglycol, D-mannitol, benzyl benzoate, ehtanol, tris(hydroxymethyl)aminomethane, cholesterol, triethanolamine, sodium carbonate, sodium citrate and the like. Suitable examples of (g) the suspending agent may include, for example, surfactants such as stearyltriethanolamine, sodium lauryl sulfate, laurylaminopropionic acid, lecithin, benzalkonium chloride, benzethonium chloride and glycerol monostearate; and hydrophilic macromolecules such as polyvinyl alcohol, polyvinylpyrrolidone, sodium carboxymethylcellulose, methyl cellulose, hydroxymethylcellulose, hydroxyethylcellulose and hydroxypropylcellulose. Suitable examples of (h) the isotonizing agent may include, for example, sodium chloride, glycerin and D-mannnitol. Suitable examples of (i) the buffering agent may include, for example, buffer solutions such as phosphate, acetate, carbonate and citrate. Suitable examples of (j) the soothing agent may include, for example, benzylalcohol. Suitable examples of (l) the preservative may include, for example, para-oxybenzoate, chlorobutanol, benzylalcohol, phenethylalcohol, dehydroacetic acid, sorbic acid and the like. Suitable examples of (m) the antioxidantal agent may include, for example, sulfite, ascorbic acid and the like. Suitable examples of (n) the flavoring agent may include, for example, cacao powder, menthol, aromatic acid, Borneol, cinnamon powder and the like. Dosage of the present compound will vary depending on the type of disease, the severity of disease, the age of patient to be administered, the route of administration or the symptoms. For example dosage administered orally for human ranges from 0.001 to 20 mg/kg, preferably from 0.01 to 15 mg/kg, more preferably from 0.1 to 10 mg/kg once or several times a day.

Description of Preparation Method

Main method for preparing cyclooctanone derivatives and cyclodecanone derivatives represented by general formula (I) according to the present invention is described below.

In each reaction below, when starting materials contain (a) an amino group, (b) a carboxy group or (c) a hydroxyl group as substituent(s), these groups may be introduced with protective groups as commonly used in the peptidechemistry field, which can be removed optionally after the completion of reaction, to afford the compound of interest.

(a) As protective groups for amino group, for example, an alkanoyl group, which may be substituted, having one to six carbon atoms (e.g., formyl, acetyl, propionyl, butyryl and the like), benzoyl, an alkoxycarbonyl group having two to six carbon atoms (e.g., methoxycarbonyl, ethoxycarbonyl and the like), phenoxycarbonyl, an aralkyloxycarbonyl having seven to fourteen carbon atoms (e.g., phenyl-$C_{2-4}$ alkoxycarbonyl such as benzyloxycarbonyl and the like), trityl, phthaloyl and the like may be used. Examples of substituents of these protective groups may include, for example, halogen atoms (e.g., fluorine, chlorine, bromine, iodine and the like), an alkanoyl group having one to six carbon atoms (e.g., formyl, acetyl, propionyl, butyryl and the like), a nitro group and the like. The number of the substituent ranges approximately from one to three.

(b) As protective groups for carboxy group, a $C_{1-6}$ alkyl group, which may be substituted (e.g., methyl, ethyl, propyl, isopropyl, butyl, tert-butyl and the like), phenyl, trityl, silyl and the like may be used. Examples of the substituents of these protective groups may include halogen atoms (e.g., fluorine, chlorine, bromine, iodine and the like), an alkanoyl group having one to six carbon atoms (e.g., formyl, acetyl, propionyl, butyryl and the like), a nitro group and the like. The number of the substituent ranges approximately from one to three.

(c) As protective groups for hydroxyl group, a $C_{1-6}$ alkyl group, which may be substituted (e.g., methyl, ethyl, propyl, isopropyl, butyl, tert-butyl and the like), phenyl, aralkyl having seven to fourteen carbon atoms (e.g., phenyl-$C_{1-4}$alkyl such as benzyl), an alkanoyl group having one to six carbon atoms (e.g., formyl, acetyl, propionyl, butyryl and the like) phenoxycarbonyl, an aralkyloxycarbonyl group having seven to fourteen carbon atoms (e.g., phenyl-$C_{1-4}$alkoxycarbonyl such as benzyloxycarbonyl), pyranyl, furanyl, silyl and the like may be used. Examples of the substituents of these protective groups may include halogen atoms (e.g., fluorine, chlorine, bromine, iodine and the like), an alkyl group having one to six carbon atoms, phenyl, an aralkyl group having seven to fourteen carbon atoms (e.g., benzyl and the like), a nitro group and the like. The number of the substituent ranges approximately from one to four.

As methods for introducing and removing the protective group, the method well known in the art or the method based on the method well known in the art [e.g., the method described in "Protective Groups in Organic Chemistry", J. F. W. McOmie et al., Plemum Press] may be used.

Method A

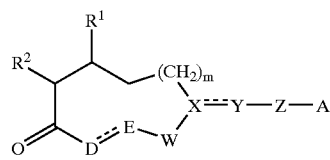

(I)

In the compound represented by general formula (I), when the partial structure >X===Y— represents the formula >CH—(CH$_2$)$_n$—, wherein n is an integer 0 or 1; or >C=CH—; or W represents —CH= and X===Y— represents C—(CH$_2$)$_p$—, wherein p is an integer 0 or 1, the compound can be prepared by the present method.

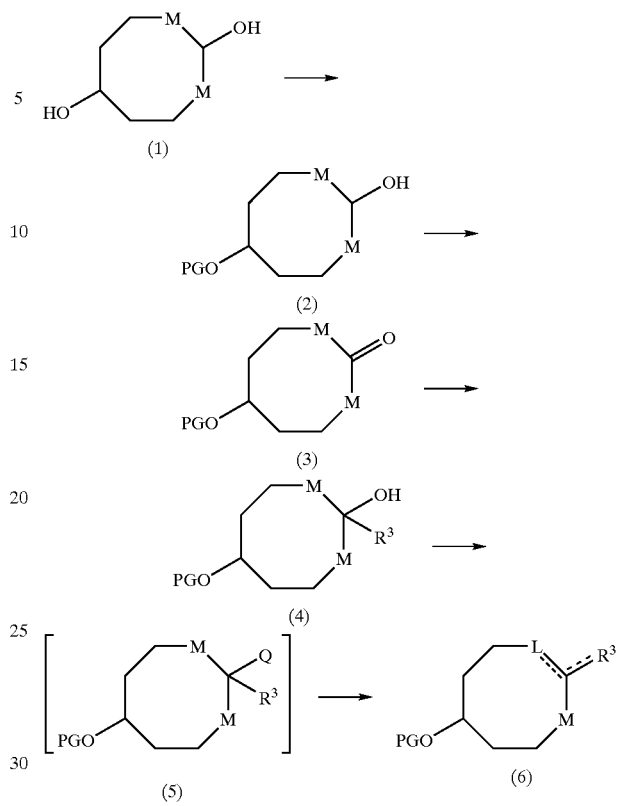

In the above formulae, M represents —CH$_2$— or —CH$_2$CH$_2$—, L represents —CH$_2$— or —CH$_2$CH$_2$— as with M, or L represents carbon chain having the same number of carbon atoms as that of M and having a double bond at one end, i.e., —CH= or —CH$_2$CH=; Q represents leaving group such as a halogen atom (e.g., chlorine, bromine, iodine and the like) or a methansulfonyloxy group, a p-toluenesulfonyloxy group, or an acetyl group; PG represents a protective group selected as necessary; $R^3$ represents an organic compound group.

In the present method A, the compound represented by (I) can be introduced a protective group into only one hydroxyl group to form the compound (2) by the method well known in the art, and then to produce the compound (3) by the oxidation method well known in the art. An oxidizing agent used in the oxidation method will vary depending on the starting material, reagent, solvent and others. Suitable examples of the oxidizing agent may include, but are not limited to, chromate compounds, dimethylsulfide-acid halides, reagent of Dess-Martin et al., tetrapropylammonium perruthenate (TPAP) and the like. Solvent which can be used will vary depending on the starting material used, reagent and others and may be solvents which do not prevent the reaction and can solve the starting material to some extent. Examples of suitable solvent may include, but are not limited to, preferably halogenated hydrocarbons such as dichlorometane, chloroform, carbon tetrachloride, 1,2-dichloroethane, 1,1,2,2-tetrachlororthane or mixtures thereof. The amount used of the oxidizing agent preferably ranges from about one to about ten mole equivalent. This reaction can be usually performed at about −78° C. to about +80° C., preferably at about −78° C. to about +40° C. over the time period from about thirty minutes to about fifty hours. The compound (3) thus obtained can be isolated and purified by a well-known isolating and purifying means such as concentration, vacuum concentration, solvent extraction, crystallization, recrystallization, transfer, chromatography and the like.

Then, the compound (3) can be reacted with well-known organometallic compound, which is prepared in suitable solvent, having organic compound group [$R^3$ represented in general formula], to produce compound (4). The organometallic compound will vary depending on the starting material, reagents, solvent and the like. Examples of the organometallic compound may preferably include, but are not limited to, organic lithium compound, organic magnesium compound, organic zinc compound, organic titanium compound, organic cerium compound including methyllithium, n-butyllithium, phenyllithium, lithium acetylide, methyl magnesium halide, phenyl magnesium halide, benzyl magnesium halide and the like. Solvents used will vary depending on the starting material used, reagent and others and may be solvents which do not prevent the reaction and can solve the starting material to some extent. Examples of suitable solvent may preferably include, but are not limited to, aliphatic hydrocarbons such as pentane, hexane or cyclohexan; ethers such as diethylethr, tetrahydrofuran, dioxane or dimethoxyethane; or mixtures thereof.

Then, the compound (4) can be treated with halogenating agent or acid halide, followed by base, to produce compound (6). In this reaction, the compound (6) can be obtained directly or via intermediate (5) depending on base used or reaction temperature. The double bond in the compound (6) can be formed in the ring or between the ring and exocyclic substituent depending on the different type of the organometallic compound used during the preparation of compound (4). Halogenating agent used in this reaction will vary depending on the starting material, reagent, solvent and others. Examples of suitable halogenating agent may preferably include, but are not limited to, phosphorus tribromide, phosphorus oxychloride, thionyl chloride and the like. Examples of preferabel halogenating agents may include acetyl chloride, methane sulfonyl chloride, p-toluenesulfonyl chloride and the like. Both base used to treat the compound (4) will vary depending on starting material, reagent, solvent and others. Examples thereof may preferably include, but are not limited to, alkali metals such as sodium hydroxide and potassium hydroxide; alkaline earth metal such as magnesium hydroxide and calcium hydroxide; alkali metal alkoxides such as sodium methoxide, sodium ethoxide and potassium tert-butoxide; alkali metal salts such as sodium carbonate, potassium carbonate, sodium bicarbonate, potassium bicarbonate, sodium acetate and potassium acetate; alkali metal hydrides such as sodium hydride and potassium hydride; and amines such as triethylamine, pyridine, picoline, N-methylmorpholine and diazabicycloundecene. The amount used of the bases preferably ranges from about 0 to about five mole equivalent relative to the amount of the compound (4). The reaction can be performed usually from about −78° C. to about +100° C, preferably from about −50° C. to about +80° C. over the time period from about thirty minutes to about ten hours. The solvent used will vary depending on starting material used, reagent and others and may be solvent which does not prevent the reaction and can dissolve the starting material to some extent. Examples of suitable solvent may include, but are not limited to, aromatic hydrocarbons such as benzene and toluene; ethers such as diethylether and tetrahydrofuran; halogenated hydrocarbons such as dichloromethane, chloroform, carbon tetrachloride, 1,2-dichloroethane and 1,1,2,2-tetrachloroethane; or mixtures thereof.

When the compound (6) is produced via the intermediate (5), the intermediate (5) can be subject to a well-known isolating and purifying means (e.g., concentration, vacuum concentration, solvent extraction) and can be further isolated and purified by crystallization, recrystallization, transfer, chromatography and the like. However, the intermediate can be used to treat with base just after concentration or vacuum concentration. For the base, similar base as described above can be used, and the amount used of the base preferably ranges from about one to about five mole equivalent relative to the amount of the intermediate (5). The reaction may be performed in the presence of solvent or performed in the absence of solvent to react the compound (5) with amines exemplified for the treatment of the compound (4), to produce the compound (6). Solvent used in this reaction will vary depending on starting material used, reagent and others, and may be solvents which do not prevent the reaction and can dissolve the starting material to some extent. Examples of suitable solvent may preferably include, but are not limited to, for example, aromatic hydrocarbons such as benzene and toluene; ethers such as diethylether and tetrahydrofuran; halogenated hydrocarbons such as dichloromethane, chloroform, carbon tetrachloride, 1,2-dichloroethane and 1,1,2,2-tetrachloroethane; or mixtures thereof.

Alternatively, the compound (4) can be heated and treated in the presence of inorganic acids such as hydrochloric acid, sulfuric acid and polyphosphoric acid, or organic acids such as p-toluenesulfonic acid in an appropriate solvent, to afford the compound (6). The reaction is performed usually at a temperature in the range from −20° C. to about +150° C., preferably in the range from about 0° C. to about +100° C. over the time period from about thirty minutes to about ten hours. Solvent used will vary depending on starting material used, reagent and others, and may be solvents which do not prevent the reaction and can dissolve the starting material to some extent. Examples of suitable solvent may preferably include, but are not limited to, for example, aromatic hydrocarbons such as benzene and toluene; ethers such as dioxane and tetrahydrofuran; alcohols such as methanol and ethanol; N,N-dimethylformamide; ethyl acetate; and water; or mixture thereof.

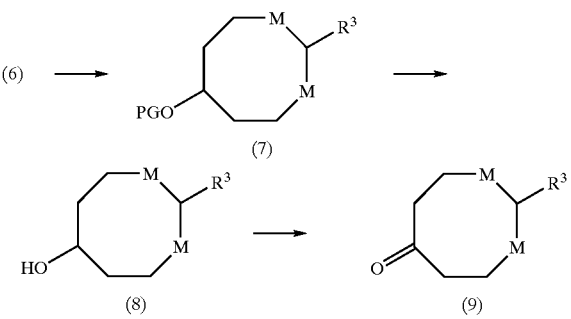

Then, the compound (6) is subject to a reductive reaction to produce the compound (7). For the reductive reaction, catalytic reduction wherein transition metal catalyst (e.g., palladium, platinum, rhodium and the like) and hydrogen are used is preferable. Solvent used will vary depending on starting material used, reagent and others, and may be solvents which do not prevent the reaction and can dissolve the starting material to some extent. Examples of suitable solvent may preferably include, but are not limited to, for example, aromatic hydrocarbons such as benzene, toluene and xylene; ethers such as diethylether, tetrahydrofuran, dioxane and dimethoxyethane; alcohols such as methanol and ethanol; N,N-dimethylformamide; ethyl acetate; and water; or mixture thereof. The reaction temperature usually ranges from about −20° C. to about +100° C., particularly preferably from about 0° C. to about +60° C. The reaction time ranges from about one hour to about forty eight hours.

The compound (7) may be deprotected by well-known method to produce the compound (8) having hydroxyl group. On the other hand, when a benzyl, benzyloxy, triphenylmethy group or the like is used as a protective group, the reductive reaction described above can act as deprotection reaction, to obtain the compound (8) from the compound (6), directly. Then, the compound (8) is subject to a well-known oxidative reaction to produce the compound (9). The oxidative reaction can be performed using the similar procedure as that used in the preparation of the compound (3).

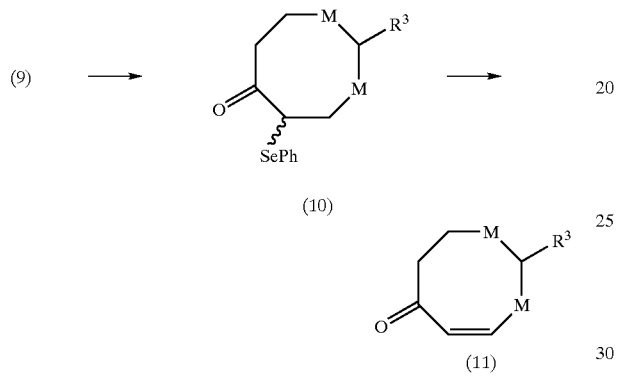

Compounds represented by the compound (9) is subject to the reaction with halogenated organoselenium compound such as phenylselenenyl chloride or phenylselenenyl bromide in the absence or presence of base in an appropriate solvent, to produce the intermediate (10). Solvent used will vary depending on starting material used, reagent and others, and may be solvents which do not prevent the reaction and can dissolve the starting material to some extent. Examples of suitable solvent may include, but are not limited to, preferably, in the presence of base, aromatic hydrocarbons such as benzene; ethers such as diethylether, tetrahydrofuran, dioxane and dimethoxyethane; or mixture thereof. In the absence of base, examples of solvent may include, in addition to the solvents described above, alcohols such as methanol and ethanol; N,N-dimethyformamide; and ethyl acetate; or mixture thereof. The base vary depending on starting material used, reagent, solvent, and the like. Examples of the base may include, but are not limited to, alkali metal hydrides such as sodium hydride and potassium hydride; lithium diethylamide; and lithium diisopropylamide; and the like. The amount used of the bases preferably ranges from about one to about two mole equivalent relative to the amount of the compound (9). The reaction temperature usually ranges from about −78° C. to about +100° C., particularly preferably from about −78° C. to about +40° C. The reaction time ranges from about one hour to about twenty four hours. The intermediate (10) thus obtained can be isolated and purified by a well-known isolating and purifying means such as concentration, vacuum concentration, solvent extraction, crystallization, recrystallization, transfer, chromatography and the like. However, the intermediate can be subject to next reaction just after concentration, vacuum concentration after solvent extraction.

The intermediate (10) can be treated with an oxidizing agent in the presence of appropriate base to produce the compound (11). The oxidizing agent used will vary depending on starting material, reagent, solvent and others. Examples of suitable oxidizing agent may include, but are not limited to, m-chloroperbenzoic acid, peracetic acid, aqueous hydrogen peroxide and the like. Suitable base will vary depending on starting material, reagent, solvent and others. Examples of suitable base may include, but are not limited to, alkali metal salts such as sodium carbonate, potassium carbonate, sodium bicarbonate, potassium bicarbonate, sodium acetate, and potassium acetate; alkali metal hydrogenphosphate salts such as disodium hydrogenphosphate and dipotassium hydrogenphosphate; organic bases such as pyridine, triethylamine and diazabicycloundecene; and the like. The amount used of the bases preferably ranges from about one to about three mole equivalent relative to the amount of the intermediate (10). Solvent used in the reaction described above will vary depending on starting material used, reagent and others, and may be solvents which do not prevent the reaction and can dissolve the starting material to some extent. Examples of suitable solvent may include, but are not limited to, preferably aromatic hydrocarbons such as benzene, toluene and xylene; halogenated hydrocarbons such as dichloromethane, chloroform, carbon tetrachloride, 1,2-dichloroethane and 1,1,2,2-tetrachloroethane; alcohols such as methanol, ethanol, propanol, isopropanol, butanol, 2-methoxyethanol and ethyleneglycol; acetonitrile; and ethyl acetate; or mixed solvent of water and the solvent described above.

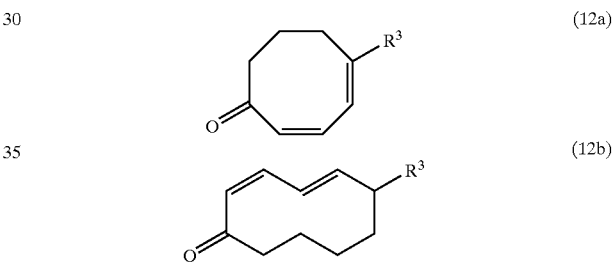

In the step of producing the compound (11), for example, both of compounds (12a) and (12b) can be produced simultaneously.

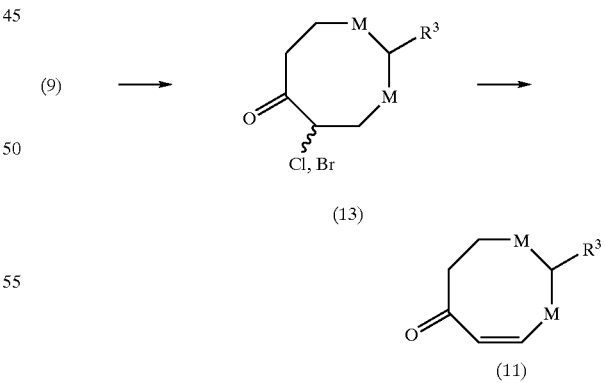

Alternatively, the compound (9) is subject to the reaction with N-chlorosuccinimide or N-bromosuccinimide in the presence of base in an appropriate solvent, to produce the intermediate (13), followed by treating with base, to produce the compound (11). Solvent used will vary depending on starting material used, reagent and others, and may be solvents which do not prevent the reaction and can dissolve the starting material to some extent. Examples of suitable solvent may include, but are not limited to, preferably aromatic hydrocarbons such as benzene; ethers such as diethylether, tetrahydrofuran, dioxane and diethoxyethane; or mixtures thereof. Bases which can be used to prepare the intermediate (13) will vary depending on starting material used, reagent, solvent and the like. Examples of suitable base may include, but are not limited to, alkali metal hydrides such as sodium hydride and potassium hydride; bases such as lithium diethylamide and lithium diisopropylamide; and the like. The amount used of the bases preferably ranges from about one to about two mole equivalent relative to the amount of the compound (9). The reaction temperature usually ranges from about −78° C. to about +100° C., particularly preferably from about −78° C. to about +40° C. The reaction time ranges from about one hour to about twenty four hours. The intermediate (13) thus obtained can be isolated and purified by a well-known isolating and purifying means such as concentration, vacuum concentration, solvent extraction, crystallization, recrystallization, and the like. However, the intermediate can be subject to next reaction just after concentration, vacuum concentration after solvent extraction.

The intermediate (13) can be treated with an appropriate base to convert into the compound (11). Suitable base will vary depending on starting material, reagent, solvent and others. Examples thereof may include, but are not limited to, alkali metal hydroxides such as sodium hydroxide and potassium hydroxide; alkali metal alkoxides such as sodium methoxide, sodium ethoxide and potassium tert-butoxide; alkali metal salts such as sodium carbonate, potassium carbonate, sodium bicarbonate, potassium bicarbonate, sodium acetate and potassium acetate; alkali metal hydrogenphosphate salts such as disodium hydrogenphosphate and dipotassium hydrogenphosphate; organic bases such as pyridine, triethylamine and diazabicycloundecene; and the like. The amount used of the bases preferably ranges from about one to about three mole equivalent relative to the amount of the intermediate (13). The solvent which can be used in the above-describe reaction will vary depending on starting material used, reagent and others, and may be solvent which does not prevent the reaction and can dissolve the starting material to some extent. Examples of suitable solvent may include, but are not limited to, aromatic hydrocarbons such as benzene, toluene and xylene; halogenated hydrocarbons such as dichloromethane, 1,2-dichloroethane and 1,1,2,2-tetrachloroethane; ethers such as diethylether, tetrahydrofuran, dioxane and dimethoxyethane; alcohols such as methanol, ethenol, propanol, isopropanol, butanol, 2-methoxyethanol, ethyleneglycol and ethyleneglycol; acetonitrile; and ethyl acetate; and mixtures thereof; the mixed solvent mixed with water and the above-described solvent.

The compound (11) thus obtained can be isolated and purified by a well-known isolating and purifying means such as concentration, vacuum concentration, solvent extraction, crystallization, recrystallization, transfer, chromatography and the like.

Moreover, a starting material, the compound (1), can be commercially available or synthesized by well-known methods described in conventional documents or the methods based thereon.

Method B

In the above-described compound represented by general formula (I), when the partial structure >X===Y— represents a group represented by >CH—O— or >CH—O—CO—, the compound can be produced by the present method.

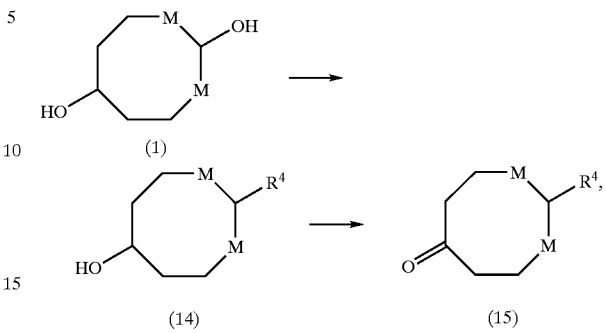

wherein R4 represents OR5 or O—C(=O)R5 wherein R5 represents an organic group.

In the present method, the compound represented by (I) can be introduced —$R^5$ group or —C(=O)$R^5$ group into only one hydroxyl group by the method well known in the art to form the compound (14) which is subject to oxidative reaction in a manner similar to the preparation method of the compound (3), to produce the compound (15). The compound (15) thus obtained can be isolated and purified by a well-known isolating and purifying means such as concentration, vacuum concentration, solvent extraction, crystallization, recrystallization, transfer, chromatography and the like.

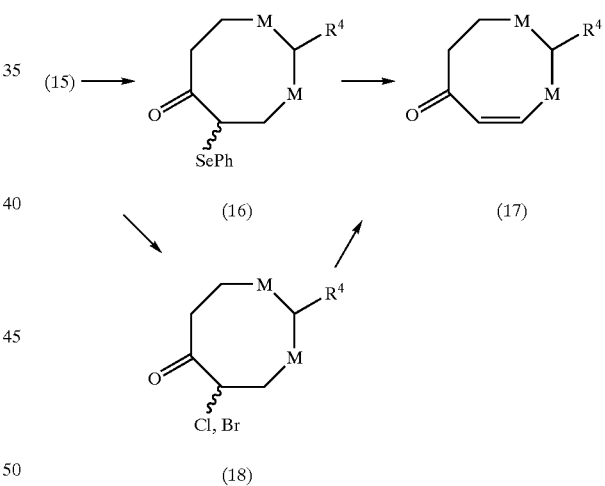

Then, the compound (15) can be treated in a manner similar to the preparation method of the compound (11), to produce the compound (17) via the intermediate (16) or the intermediate (18).

The compound (17) thus obtained can be isolated and purified by a well-known isolating and purifying means such as concentration, vacuum concentration, solvent extraction, crystallization, recrystallization, transfer, chromatography and the like.

Method C

When the partial structure >X===Y— represents a group represented by the formula >CH—CH$_2$—CH(OH)— or >CH—CH$_2$—C(=O)—, the compound can be prepared by the present method. Additionally, when the partial structure >X--Y— represents the formula >CH—(CH$_2$)$_n$— (wherein n is an integer 0 or 1), or >C=CH—, the compound can be prepared by the present method in addition to [Method A].

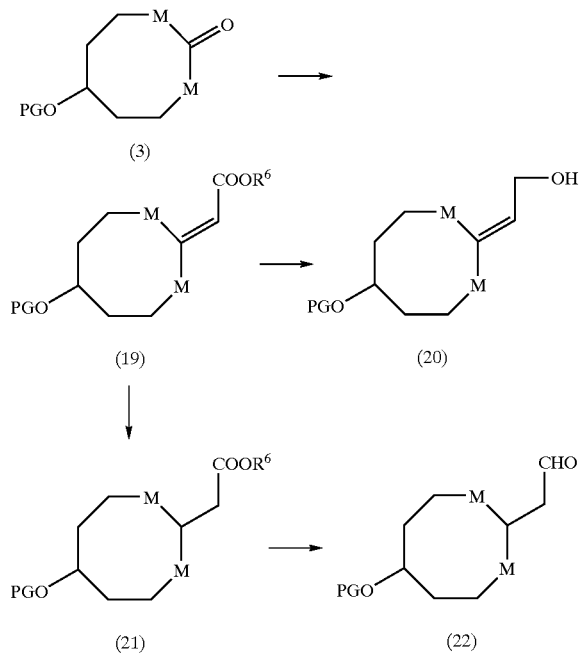

Horner-Emmons reaction or Peterson reaction known in the art can be used with the compound (3) described above, to produce the compound (19) (wherein R$^6$ varies depending on the compounds used in the reaction and represents a methyl group, an ethyl group, a benzyl group or the like). Examples of the compound used in Horner-Emmons reaction may include methyl dimethylphosphonoacetate, benzyl dibenzylphosphonoacetate and the like. Examples of the compound used in Peterson reaction may include, for example, methyl 2-trimethylsilylacetate, ethyl 2-trimethylsilylacetate, benzyl 2-trimethylsilylacetate and the like. Solvent which can be used in both reaction will vary depending on starting material used, reagent and others, and may be, but be not limited to, solvents which do not prevent the reaction and can dissolve the starting material to some extent.

Examples of suitable solvent used in Homer-Emmons reaction may include, for example, aromatic hydrocarbons such as benzene, toluene and xylene; ethers such as diethylether, tetrahydrofuran, dioxane and dimethoxyethane; N,N-dimethylformamide; and dimethylsulfoxide; and mixture thereof. Examples of suitable solvent used in Peterson reaction may include, for example, aromatic hydrocarbons such as benzene, toluene and xylene; ethers such as diethylether, tetrahydrofuran, dioxane and dimethoxyethane; and mixture thereof. The reaction temperature usually ranges from about −20° C. to about +150° C., particularly preferably from about 0° C. to about +100° C. The reaction time ranges from about one hour to about ninety six hours.

Then, the compound (19) can be treated with a reducing agent known in the art to produce the compound (20). The reducing agent used will vary depending starting material, reagent, solvent and others. Examples of suitable reducing agent may include, but are not limited to, lithium aluminium hydride and diisobutylaluminium hydride. The amount used of the reducing agent preferably ranges from about 1 to about 4 mole equivalent relative to the amount of the compound (19). The reaction temperature usually ranges from about −78° C. to about +100° C., preferably from about −78° C. to about +40° C. over the time period from about thirty minutes to about ten hours. Solvent which can be used in the above-described reaction will vary depending on starting material used, reagent and others, and may be solvents which do not prevent the reaction and can dissolve the starting material to some extent. Examples of suitable solvent may include, but are not limited to, preferably aromatic hydrocarbons such as benzene and toluene; ethers such as diethylether and tetrahydrofuran; halogenated hydrocarbons such as dichloromethane and 1,2-dichloroethane; and mixtures thereof. The compound (20) thus obtained can be isolated and purified by a well-known isolating and purifying means such as concentration, vacuum concentration, solvent extraction, crystallization, recrystallization, transfer, chromatography and the like. However, the compound can be subject to treatment with base just after concentration or vacuum concentration.

Alternatively, the compound (19) can be subject to a reductive reaction similar to the preparation method of the compound (7), to produce the compound (21). Then, the compound (21) can be reacted in a manner similar to the preparation method of the compound (20), to produce the compound (22). The compound (21) and (22) thus obtained can be isolated and purified by a well-known isolating and purifying means such as concentration, vacuum concentration, solvent extraction, crystallization, recrystallization, transfer, chromatography and the like.

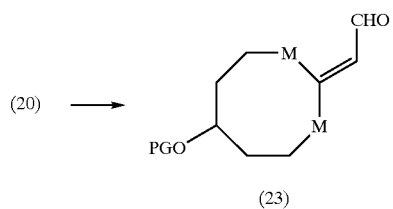

Then, the compound (20) can be treated with an oxidizing agent to produce the compound (23). The oxidizing agent will vary depending on the starting material used, reagent, solvent and others. Examples of suitable oxidizing agent may include, but are not limited to, manganese dioxide, dimethylsulfoxide-acid halide, chromate compounds, and the like. The amount used of the oxidizing agents preferably ranges from about 1 to about 10 mole equivalent relative to the amounts of the compound (20). Solvent used in this reaction will vary depending on starting material used, reagent, and others, and may be solvents which do not prevent the reaction and can dissolve the starting material to some extent. Examples of suitable solvent may include, but are not limited to, preferably aromatic hydrocarbons such as benzene, toluene and xylene; halogenated hydrocarbons such as dichloromethane, chloroform, carbon tetrachloride, 1,2-dichloroethane and 1,1,2,2-tetrachloroethane; and mixture thereof.

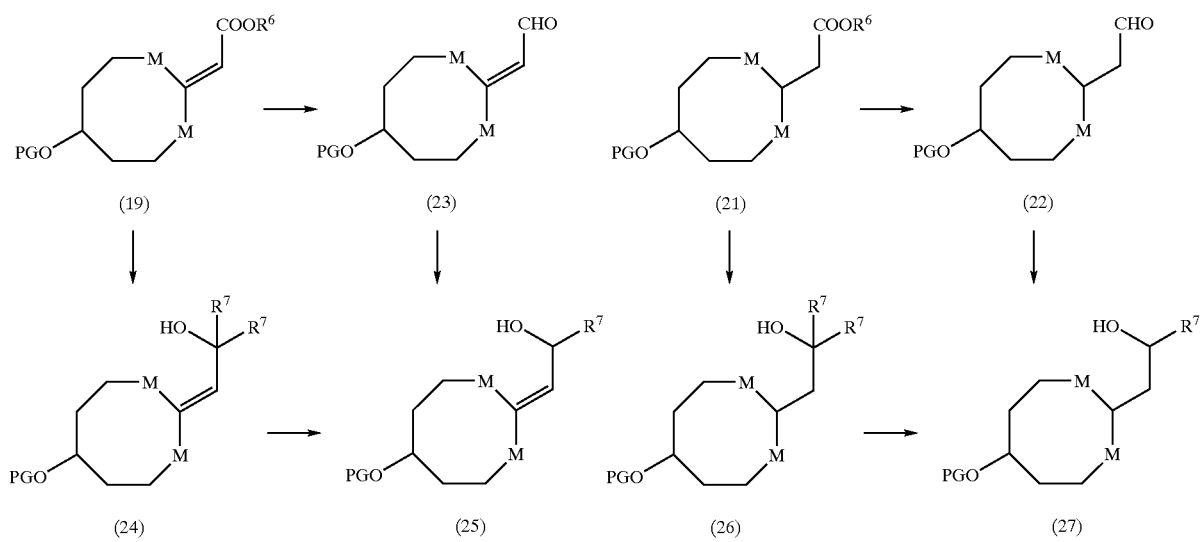

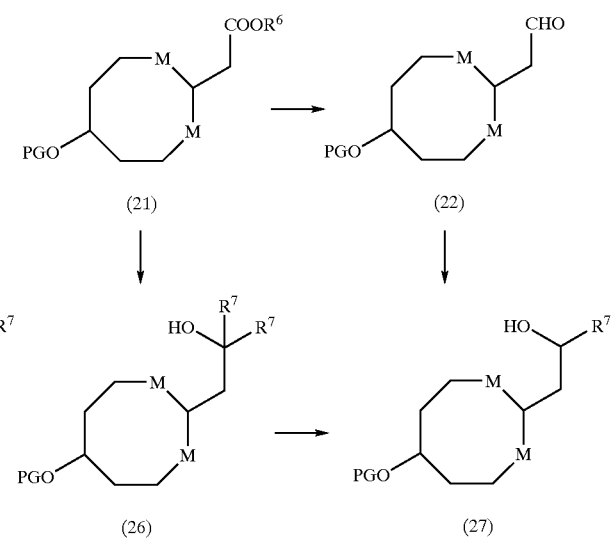

The compounds (19), (21), (22) and (23) can be treated with a well-known organometallic compound having organic compound group [R⁷ in formula] in an appropriate solvent in a manner similar to the preparation of the compound (4), to replace a variety of substituents. Solvent used in this reaction will vary depending on starting material used, reagent and others, and may be, but not limited to, solvents which do not prevent the reaction and can dissolve the starting material to some extent. As a result, the compounds (24), (26), (27) and (25) can be produced from the compounds (19), (21), (22) and (23), respectively.

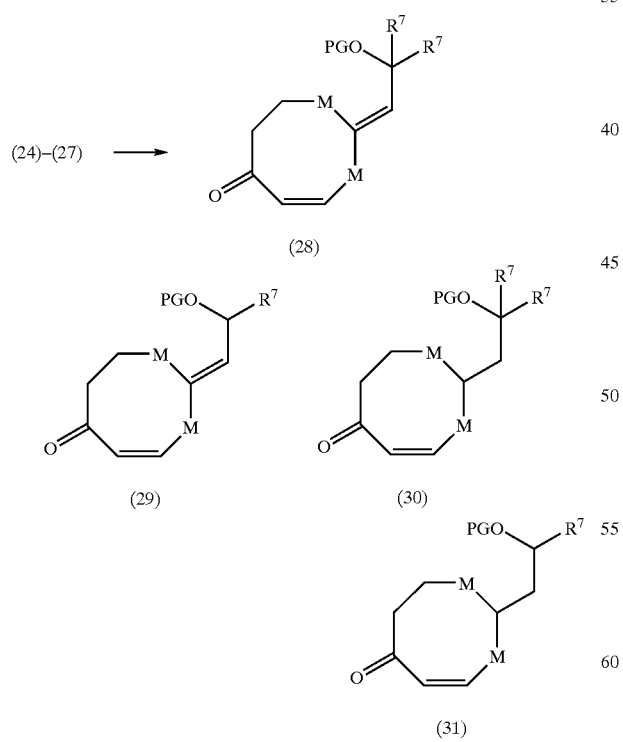

Hydroxyl groups in the compounds (24) to (27) can be protected with protective groups, followed by reacting in a manner similar to the preparation process of the compound (11) from the compound (7), to produce the compounds (28) to (31). As the protective group of the compound, a protective group which can be deprotected under different condition from the protective group which has been protecting hydroxyl group can be used as necessary.

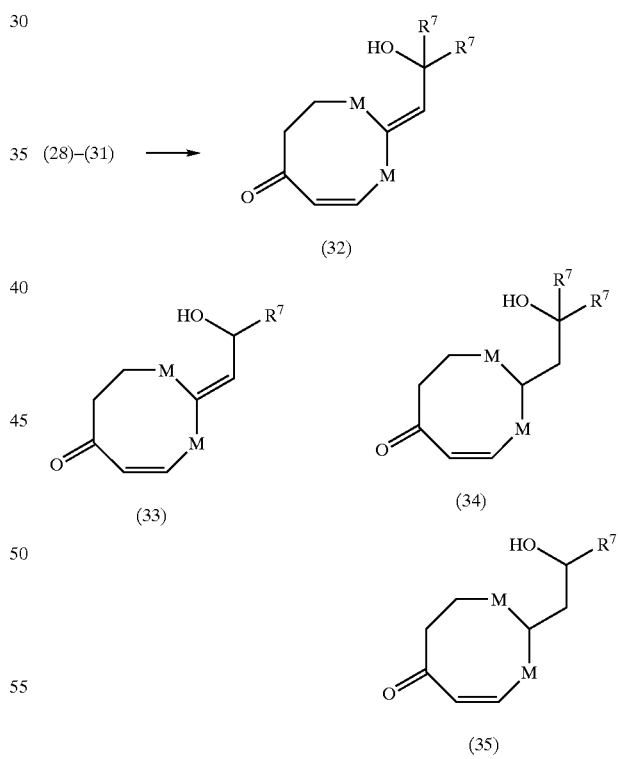

Then, the compounds (28) to (31) can be deprotected to produce the compounds (32) to (35). The compounds (32) to (35) thus obtained can be isolated and purified by a well-known isolating and purifying means such as concentration, vacuum concentration, solvent extraction, crystallization, recrystallization, transfer, chromatography and the like.

Method D

The compound, wherein $R^1$ and $R^2$ each represents a hydroxyl group, an alkoxy group having one to six carbon atoms or a $C_{1-6}$ alkoxy-$C_{1-6}$ alkoxy group, can be synthesized by the present method.

The compound (11) synthesized by Method A or the compound (17) synthesized by Method B can be used to convert into the compound (38) by using the method described below:

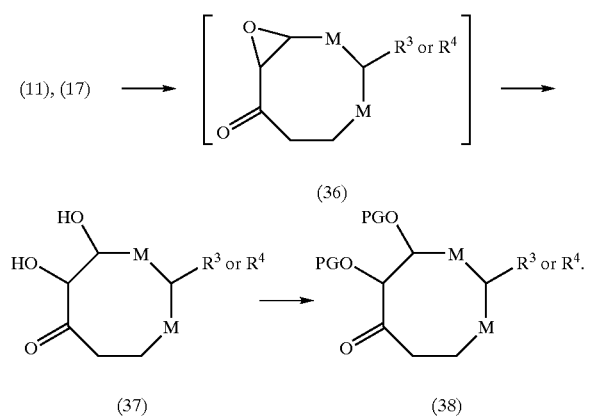

The compound (11) or (17) is subject to the reaction with an oxidizing agent in an appropriate solvent to produce the compound (37). In this reaction, the compound (37) can be produced directly from the compound (11) or (17) by using osmium tetroxide as the oxidizing agent. Osmium tetroxide can be used in an amount of not less than stoichiometrical amount, or in an amount of catalyst quantity in co-existence of another oxidizing agent. In this case, the co-existing oxidizing agent will vary depending on starting material, reagent, solvent and others. Suitable examples thereof may include, but are not limited to, chlorates, amine-N-oxides, and the like. The amount used of the bases preferably ranges from about 1 to about 5 mole equvalent relative to the amount of the compound (11) or (17). The reaction temperature suitably ranges from about −30° C. to about +80° C. The reaction time ranges from about two hours to seventy two hours. Solvent which can be used in this reaction will vary depending on starting material used, reagent and others, and may be solvents which do not prevent the reaction and can dissolve the starting material to some extent. Examples of suitable solvent may include, but are not limited to, preferably aliphatic hydrocarbons such as pentane, hexane and cyclohexane; ethers such as diethylether, tetrahydrofuran, dioxane and dimethoxyethane; and mixture thereof; or solvent mixed with water and the above-described solvent.

Alternatively, when aqueous hydrogen peroxide is used as the oxidizing agent, the compound (11) or (17) can be converted into the intermediate (36), followed by treating with an acid, to produce the compound (37). The amount used of hydrogen peroxide preferably ranges from about 1 to about 8 mole equivalent relative to the amount of the compound (11) or (17). Solvent which can be used in the acid treatment will vary depending on starting material used, reagent and others, and may be solvents which do not prevent the reaction and can dissolve the starting material to some extent. Examples of suitable solvent may include, but are not limited to, preferably aromatic hydrocarbons such as benzene, toluene and xylene; halogenated hydrocarbons such as dichloromethane, chloroform, carbon tetrachloride, 1,2-dichloroethane and 1,1,2,2-tetrachloroethane; alcohols such as methanol, ethanol, propanol, isopropanol, butanol, 2-methoxyethanol and ethyleneglycol; or solvent mixed with water and the above-described solvent.

Then, a hydroxyl group of the compound (37) can be protected according to the method known in the art in an appropriate solvent to produce the compound (38). Solvent used in the acid treatment will vary depending on starting material used, reagent and others, and may be, but not limited to, solvents which do not prevent the reaction and can dissolve the starting material to some extent. The protective group can be selected from those described in Description of Preparation.

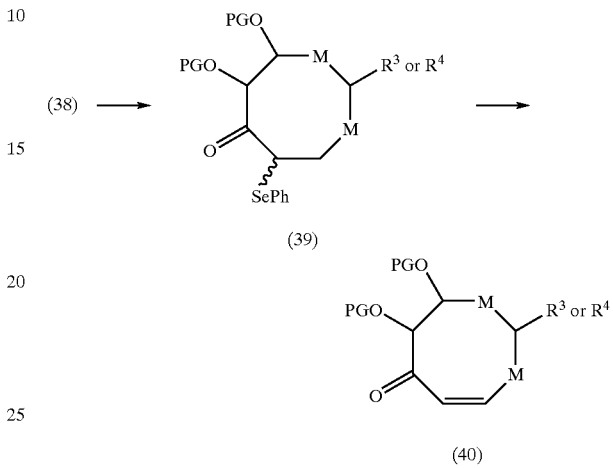

Then, the compound (40) can be produced from the compound (38) via the intermediate (39) in a manner similar to the preparation method of the compound (11). The compound (40) thus obtained can be isolated and purified by a well-known isolating and purifying means such as concentration, vacuum concentration, solvent extraction, crystallization, recrystallization, transfer, chromatography and the like.

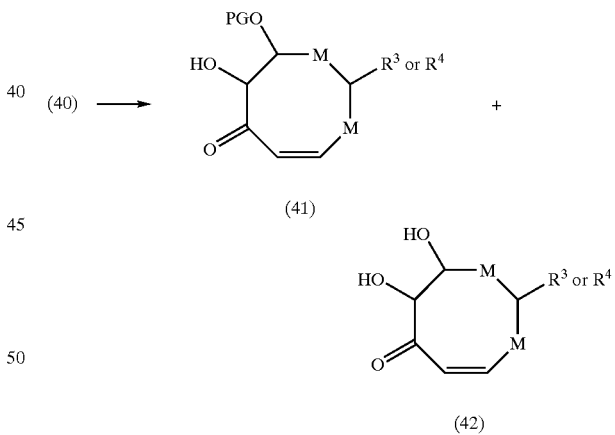

A protective group in the compound (40) can be deprotected by the well-known method to afford the compound (42). Moreover, the compound (41) can be obtained in this reaction process by adjusting the reaction time, the reaction temperature and equivalent of reagent used.

The compounds (41) and (42) thus obtained can be isolated and purified by a well-known isolating and purifying means such as concentration, vacuum concentration, solvent extraction, crystallization, recrystallization, transfer, chromatography and the like.

EXAMPLES

Although the present invention will now be described in further detail in the following reference examples, examples and test examples, these examples are intended to be by way of example only and not to limit the present invention in any way, and variations and modifications may be made without departing from the spirit and scope of the invention.

Reference Example 1

5-Benzyl-1-cyclooctanol

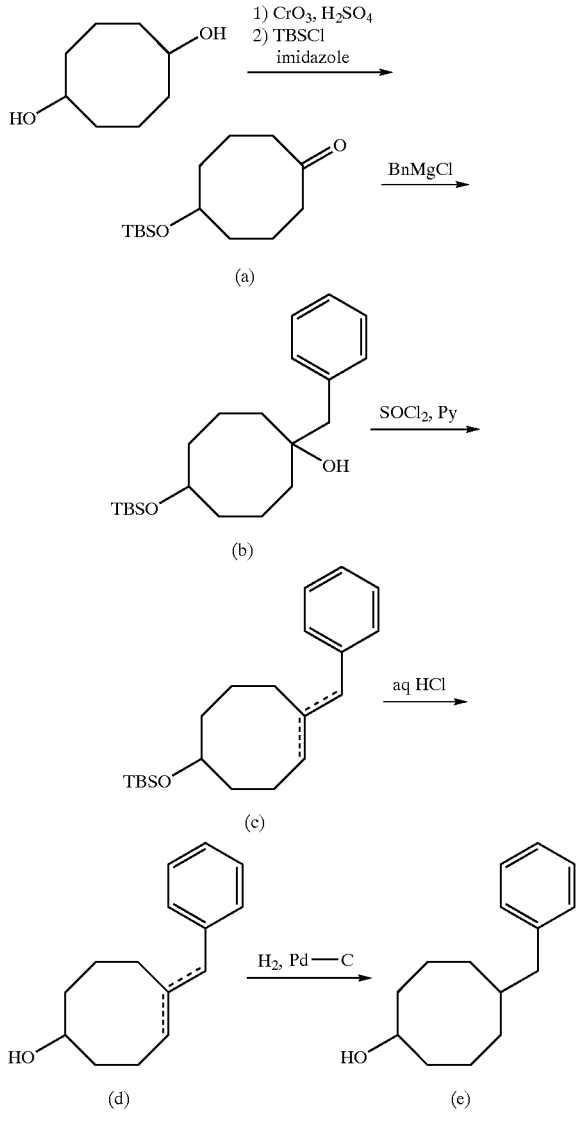

(a) 5-(Tert-butyl)dimethylsilyloxy-1-cyclooctanone 9.8 g of 1,5-cyclooctanediol was dissolved in 150 ml of acetone, and to the solution was added Jones reagent prepared with 11.5 ml of sulfuric acid, 13 g of chromic acid and 20 ml of water. The solution was stirred at room temperature for fifteen minutes. To the reaction solution was added 2 ml of 2-propanol. Then, the solution was filtered through Celite. The residue was washed with dichloromethane and the washing solution was combined with the filtrate. The filtrate was washed with water and a saturated saline solution, and dried over anhydrous sodium sulfate. The solvent was evaporated, to afford a white solid. The crude product was dissolved in 200 ml of dimethylformamide. To the solution were added 6.6 g of imidazole and 12 g of tert-butylchlorodimethysilane. The reaction solution was stirred at room temperature overnight, and then cooled in an ice bath. To the resulting solution was added a saturated sodium bicarbonate aqueous solution. The reaction solution was extracted with diethylether, washed with a saturated saline solution, and dried over anhydrous sodium sulfate. The solvent was evaporated. The residue was subject to column chromatography on silica gel, and the eluate with ethyl acetate-hexane (1:9) was collected, to afford 13.6 g of the titled compound (a) as colorless liquid.

$^1$H-NMR $\delta$(CDCl$_3$); 0.04(s,2H), 0.12(s,4H), 0.88(s,6H), 0.92(s, 3H), 1.69–1.85(m,6H), 1.94–2.12(m,2H), 2.26–2.36 (m,2H), 2.54–2.64(m,2H), 3.62–3.69(m,1H).

(b) 1-Benzyl-5-(tert-butyl)dimethylsilyloxy-1-cyclooctanol 1.2 g of magnesium was suspended in 40 ml of anhydrous ether, and the resulting suspension was warmed in the water bath at 40° C. A small piece of iodine crystal and a drop of bromoethane were added to the solution, followed by adding 5.7 ml of benzyl chloride dropwise slowly. To the resulting grayish white mixture, 4.0 g of the above product (a) was added. The resulting solution was stirred at 40° C. for three hours followed by at room temperature for further two days. The reaction solution was poured into ice water, and 2N hydrochloric acid was added to the solution until pH of the aqueous phase was reached at approximately 3. Then, the reaction solution was extracted with ether. The organic layer was washed with a saturated saline solution, and dried over anhydrous sodium sulfate. The solvent was evaporated under reduced pressure. The resulting crude product was purified by column chromatography on silica gel, and the eluate with ethyl acetate-hexane (1:15) was collected, to afford 4.5 g of the titled compound (b) (mixture of cis- and trans-isoforms) as colorless liquid.

$^1$H-NMR $\delta$(CDCl$_3$); 0.04(s,6H), 0.89(s,9H), 0.92(s,3H), 1.54–1.74(m,10H), 1.76–1.88(m,2H), 2.74(s,2H), 3.76–3.84 (m,1H), 7.19–7.32(m,5H).

(c) [(5-Benzyl-4-cyclooctenyl)oxy](tert-butyl) dimethylsilane and tert-butyl(dimethyl)[5-(phenylmethylene)-cyclooctyloxy]silane 1.7 g of the above product (b) was dissolved in 40 ml of pyridine. To the solution was added 0.43 ml of thionyl chloride while cooling with an ice bath. After stirring at 0° C. for twenty minutes, the reaction solution was poured into ice water, and extracted with ether. The organic layer was washed with a saturated saline solution, and dried over anhydrous sodium sulfate. The solvent was evaporated under reduced pressure, to afford 1.6 g of the titled compound as pale yellow liquid.

$^1$H-NMR $\delta$(CDCl$_3$); 0.01(s), 0.04(s,6H), 0.86(s), 0.89(s, 9H), 1.50–1.80(m,8H), 1.88–2.10(m,2H), 2.14–2.36(m,2H), 3.27–3.29 (m), 3.70–3.78(m,1H), 5.40–5.47(m), 6.34(s,1H), 7.19–7.32 (m,5H).

(d) 5-Benzyl-4-cyclooctene-1-ol and 5-(phenylmethylene)-1-cyclooctanol 2.3 g of the above product (c) was dissolved in 40 ml of tetrahydrofuran, and then 10 ml of 1N hydrochloric acid was added to the solution. After stirring at 40° C. for two and a half hours followed by at room temperature overnight, to the reaction solution was added 1N sodium hydroxide. The solution was extracted with ethyl acetate. The organic layer was washed with a saturated saline solution, and dried over anhydrous sodium sulfate. The solvent was evaporated under reduced pressure, to afford 2.2 g of the titled compound (d) as pale yellow liquid.

$^1$H-NMR δ(CDCl$_3$); 1.41–1.94(m,8H), 1.96–2.10(m,2H), 2.15–2.57 (m,2H), 3.68–3.76(m), 3.88–3.96(m,1H), 5.40–5.46(m), 6.32(s, 1H), 7.13–7.32(5H,m).

(e) 5-Benzyl-1-cyclooctanol 2.2 g of the above product (d) were dissolved in 50 ml of ethanol, and 0.2 g of 10% palladium-carbon was suspended in the solution with stirring under hydrogen atmosphere for two hours. The catalyst was removed by filtration and the filtrate was evaporated, to afford 2.5 g of the titled compound (e) as a colorless oily matter.

$^1$H-NMR δ(CDCl$_3$); 1.32–1.70 (m,8H), 1.72–1.90(m, 4H), 2.50(dd, J=7.2 Hz, 4.5 Hz 2H), 3.88–3.96(m,1H), 7.13–7.30(5H,m).

Reference Example 2

5-[2-(4-Methoxymethoxyphenyl)ethyl]-1-cyclooctanol

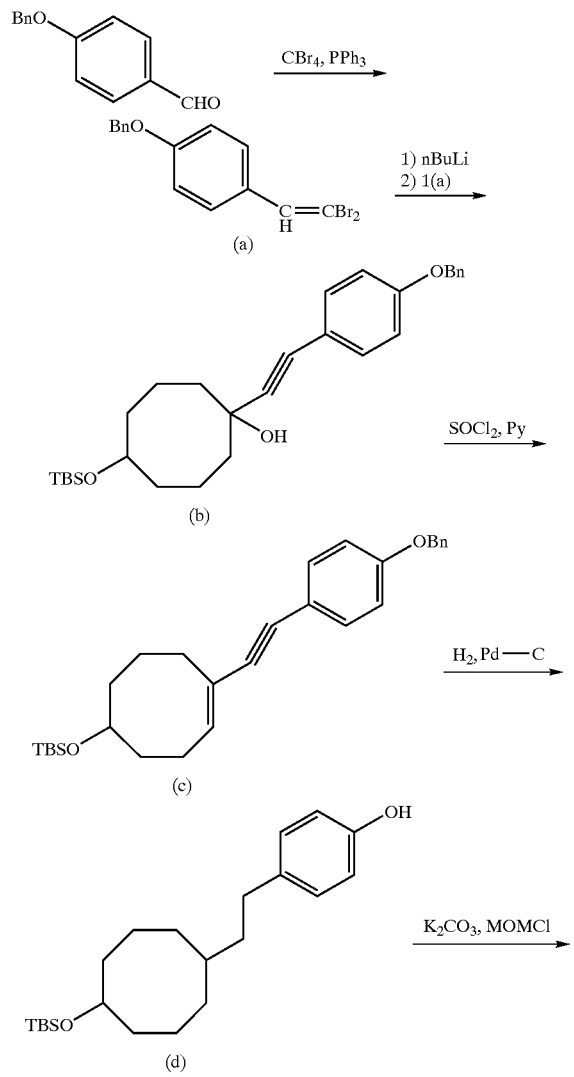

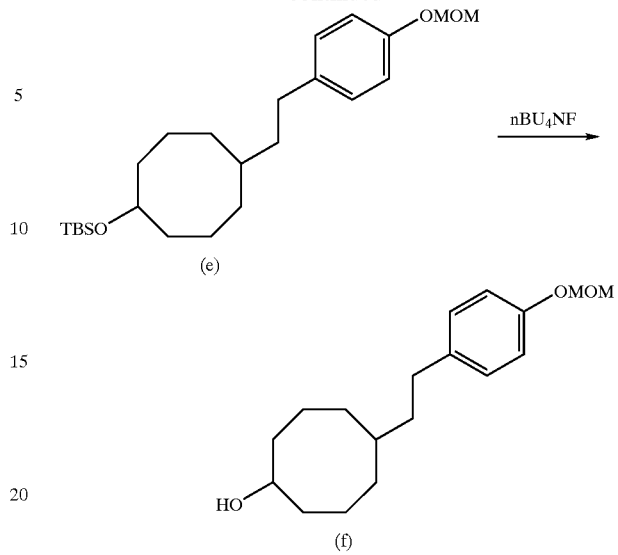

(a) 2-(4-Benzyloxyphenyl)-1,1-dibromoethylene 43 g of carbon tetrabromide was dissolved in 100 ml of dichloromethane, and then 69 g of triphenylphosphine was added to the solution while cooling in an ice bath, followed by stirring at 0° C. for ten minutes. Then, to the resulting solution, a solution of 7.0 g of 4-benzyloxybenzaldehyde dissolved in 100 ml of dichloromethane was added dropwise, followed by stirring at 0° C. for further twenty minutes. 30 ml of a saturated sodium bicarbonate aqueous solution was added slowly to the reaction solution, followed by adding 100 ml of water. The reaction solution was extracted with dichloromethane. The organic layer was washed with a saturated sodium bicarbonate aqueous solution, and dried over anhydrous sodium sulfate. The solvent was evaporated under reduced pressure. Ether was added to the residue, and insoluble substance was removed by filtration and the filtrate was evaporated. The residue was subject to column chromatography on silica gel, and the eluate with ethyl acetate-hexane (1:20) was collected, to afford 6.4 g of the titled compound(a) as a white solid.

$^1$H-NMR δ(CDCl$_3$); 5.09(s,2H), 6.94–7.00(m,2H,m), 7.25–7.60 (10H,m).

(b) 1-[2-(4-Benzyloxyphenyl)ethynyl]-5-(tert-butyl)-dimethylsilyloxy-1-cyclooctanol 6.0 g of the above product (a) was dissolved in 150 ml of anhydrous tetrahydrofuran, and then the solution was cooled to –70° C. To the reaction solution was added 20.5 ml of a solution (1.6 M) of n-butyllithium in hexane, and the reaction solution was stirred at –70° C. for twenty minutes. To the solution was added 4.0 g of anhydrous cerous chloride, followed by stirring at –70° C. for two hours. Then, 1.4 g of the product prepared in Reference Example 1 (a) was added to the reaction solution, followed by stirring for two hours while warming from –70° C. to –40° C. The reaction solution was poured into ice water, stirred for fifteen minutes, and filtered through Celite. The filtrate was extracted with ether, and organic layer was dried over anhydrous sodium sulfate. The solvent was evaporated. The residue was purified by column chromatography on silica gel, and the eluate with ethyl acetate-hexane (1:20) was collected, to afford 2.3 g of the titled compound(b) above as a pale yellow solid.

¹H-NMR δ(CDCl₃); 0.05(s,6H), 0.89(s,9H), 1.52–1.76 (m,8H), 1.78–2.10(m,2H), 2.14–2.22(m,2H), 3.86–3.93(m, 1H), 5.07(s,2H), 6.90(d,J=7.8 Hz,2H), 7.30–7.43(m,7H).

(c) 5-{2-[4-(Benzyloxy)phenyl]ethynyl-4-cyclooctenyloxy}-(tert-butyl)dimethylsilane 2.3 g of the above product (b) was dissolved in 50 ml of pyridine, and then to the solution was added 0.43 ml of thionyl chloride at −20° C. The reaction solution was stirred at −20° C. for twenty minutes and poured into ice water and extracted with ether. The organic layer was washed with a saturated saline solution and dried over anhydrous sodium sulfate. The solvent was evaporated under reduced pressure. The resulting crude product was purified by column chromatography on silica gel, and the eluate with ethyl acetate-hexane (1:30) was collected, to afford 1.1 g of the titled compound (c) as colorless liquid.

¹H-NMR δ(CDCl₃); 0.04(s), 0.05(s,6H), 0.89(s,9H), 1.54–1.84(m,6H), 2.01–2.11(m,1H), 2.24–2.50(m,3H), 3.79–3.85(m,1H), 5.06(s, 2H), 6.18(t,J=8.0 Hz,1H), 6.90(d, J=8.4 Hz,2H), 7.29–7.44(m,7H).

(d) 4-(2-{-[(Tert-butyl)dimethylsilyloxy]cyclooctyl}ethyl)-phenol 1.1 g of the above product (c) was treated in a manner similar to Reference Example 1 (e), to yield 1.0 g of the titled crude product (d) as colorless liquid.

¹H-NMR δ(CDCl3); 0.03(s), 0.04(s,6H), 0.88(s,9H), 1.30–1.86(m, 15H), 2.47–2.57(m,2H), 3.70–3.86(m,1H), 4.63(s,1H), 6.74(d, J=8.0 Hz,2H), 7.03(dd,J=2.4 Hz,8.0Hz, 2H).

(e) (Tert-butyl){5-[2-(4-methoxymethoxyphenetyl)cyclooctyl]-oxy}dimethylsilane 1.0 g of the above product (d) was dissolved in 20 ml of acetone, and then 0.60 g of potassium carbonate and 0.28 ml of chloromethylmethylether were added to the solution, followed by stirring at room temperature for two hours. Adding of reagent and stirring were continued at room temperature until TLC indicated that starting materials had been consumed. As a result, adding 1.8 g of potassium carbonate and 0.84 ml of chloromethylmethylether and stirring for three days had been required. The reaction solution was filtered, and to the filtrate was added 2 ml of triethylamine. The solvent was evaporated under reduced pressure. The resulting crude product was purified by column chromatography on silica gel, and the eluate with ethyl acetate-hexane (1:20) was collected, to afford 0.59 g of the titled compound (e) as colorless liquid.

¹H-NMR δ(CDCl₃); 0.03(s), 0.04(s,6H), 0.88(s,9H), 1.30–1.86(m,15H), 2.52–2.57(m,2H), 3.48(s,3H), 3.70–3.85 (m,1H), 5.15(s,2H), 6.95(d,J=8.4 Hz,2H), 7.08(dd,J=8.5 Hz,2H).

(f) 5-[(4-Methoxymethoxy)phenethyl]-1-cyclooctanol 0.59 g of the above product (e) was dissolved in 20 ml of anhydrous tetrahydrofuran, and then to the solution was added 3 ml of a solution (1.0M) of tetra n-butylammonium fluoride in hexane. The reaction solution was stirred at room temperature for one and a half hours. Adding of reagents and stirring was continued at 20° C. until TLC indicated that starting materials had been consumed. As a result, adding 6 ml of a solution (1.0M) of tetra n-butylammonium fluoride in hexane and stirring for one day had been required. The reaction solution was poured into ice water and extracted with ether. The organic layer was washed with a saturated saline solution, and dried over anhydrous sodium sulfated. The solvent was evaporated. The resulting crude product was purified by column chromatography on silica gel, and the eluate with ethyl acetate-hexane (1:5) was collected, to afford 0.40 g of the titled compound (f) as colorless liquid.

¹H-NMR δ(CDCl₃); 1.22–1.74(m,12H), 1.78–1.90(m, 3H), 2.52–2.57(m,2H), 3.48(s,3H), 3.72–3.94(m,1H), 5.16 (s,2H), 6.95(dd, J=2.0 Hz,8.4 Hz,2H), 7.08(d,J=8.4 Hz,2H).

Reference Example 3

6-Phenyl-1-cyclodecanol

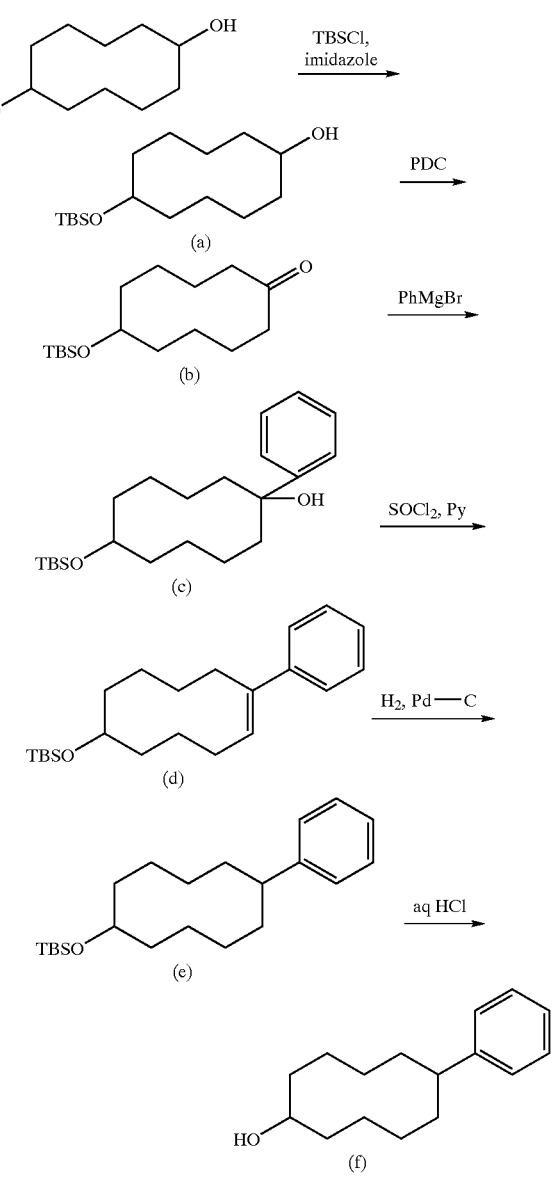

(a) 6-(Tert-butyl)dimethylsilyloxy-1-cyclodecanol 0.89 g of 1,6-cyclodacanediol was dissolved in 30 ml of dimethylformamide, and then 0.56 g of imidazole and 0.78 g of tert-butylchlorodimethylsilane were added to the solution. The reaction solution was stirred at room temperature for three days, and the solvent was evaporated. The residue was dissolved in ethyl acetate and washed with water. The aqueous layer was saturated with sodium chloride, and extracted with ethyl acetate three times. The extract was dried over anhydrous sodium sulfate and the solvent was evaporated. The residue was subject to column chromatography on silica gel, and the eluate with ethyl acetate-hexane (1:10) was collected, to afford 0.77 g of the titled compound (a) as colorless liquid.

$^1$H-NMR δ(CDCl$_3$); 0.04(s), 0.05(s,6H), 0.89(s,9H), 1.24–1.29(m, 2H), 1.36–1.84(m,14H), 3.76–4.04(m,2H).

(b) 6-(Tert-butyl)dimethylsilyloxy-1-cyclodecanone 1.5 g of pyridinium dichromate was dissolved in 30 ml of dichloromethane, to the solution was added 0.77 g of 6-tert-butyldimethylsilyloxy-1-cyclodecanol prepared in above-described (a). The mixture was stirred at room temperature for one and a half hours. Then, another 2.5 g of pyridinium dichromate was added to the reaction solution and the reaction solution was stirred at room temperature for further three hours. To the reaction solution was added 50 ml of ether, followed by purifying by column chromatography on Florisil, and the eluate with ether was collected, to afford 0.73 g of the titled compound (b) as colorless liquid.

$^1$H-NMR δ(CDCl$_3$); 0.05(s,6H), 0.88(s,9H), 1.35–1.57 (m,8H), 1.75–1.95(m,4H), 2.34–2.44(m,2H), 2.54–2.63(m, 2H), 3.73–3.80 (m,1H).

(c) 1-Phenyl-6-(tert-butyl)dimethylsilyloxy-1-cyclodecanol 21 ml of a solution (1.0 M) of phenylmagnesium bromide in tetrahydrofuran was dissolved in 50 ml of anhydrous ether, and to the solution was added 1.5 g of the above product (b). The reaction solution was stirred at 40° C. for three and a half hours. The reaction solution was poured into ice water and adjusted to pH 4 by addition of 2N HCl, and extracted with ether. The organic layer was washed with a saturated saline solution, and dried over anhydrous sodium sulfate. The solvent was evaporated. The residue was subject to column chromatography on silica gel, and the eluate with ethyl acetate-hexane (1:20) was collected, to afford 1.1 g of the titled compound (c) as a colorless oily matter.

$^1$H-NMR δ(CDCl$_3$); 0.04, 0.05(s,6H), 0.88, 0.89(s,9H), 1.24–1.35 (m,4H), 1.51–1.83(m,10H), 1.85–2.10(m,2H), 3.82–3.94(m,1H), 6.80–6.85(m,1H), 6.93(t,J=7.6 Hz,1H), 7.19–7.29(m,1H), 7.34(t, J=7.6 Hz,1H), 7.49–7.53(m,1H).

(d) (Tert-butyl)dimethyl[(6-phenyl-5-cyclodecenyl) oxy]silane 1.1 g of the above product (c) was treated in a manner similar to Reference Example 2 (c), to yield 0.78 g of the titled compound (d) as a colorless oily matter.

$^1$H-NMR δ(CDCl$_3$); 0.04, 0.05(s,6H), 0.88(s,9H), 1.24–1.98(m, 10H), 2.20–2.45(m,2H), 2.64–2.72(m,2H), 3.80–3.90(m,1H), 5.67 (t,J=8.0 Hz,1H), 7.20–7.40(m,5H).

(e) (Tert-butyl)dimethyl(6-phenyl-5-cyclodecyloxy) silane 0.78 g of the above product (d) was treated in a manner similar to Reference Example 1 (e), to yield 0.76 g of the titled compound (e) as a colorless oily matter.

$^1$H-NMR δ(CDCl$_3$); 0.04, 0.05(s,6H), 0.88(s,9H), 1.42–1.75 (m,14H), 1.76–1.92(m,2H), 2.74–2.82(m), 2.88–2.98(m,1H), 3.78–3.86(m), 4.04–4.14(m,1H), 7.12–7.30(m,5H).

(f) 6-Phenyl-1-cyclodecanol 0.76 g of the above product (e) was treated in a manner similar to Reference Example 1 (d), to yield 0.73 g of the crude, titled compound (f) as a colorless oily matter.

$^1$H-NMR δ(CDCl$_3$); 1.22–1.34(m,2H), 1.38–1.95(m, 14H), 2.76–2.86 (m), 2.90–3.00(m,1H), 3.88–3.98(m), 4.08–4.20(m,1H), 7.12–7.30 (m,5H).

Reference Example 4

5-(2-Pyridylmethyl)-1-cyclooctanol

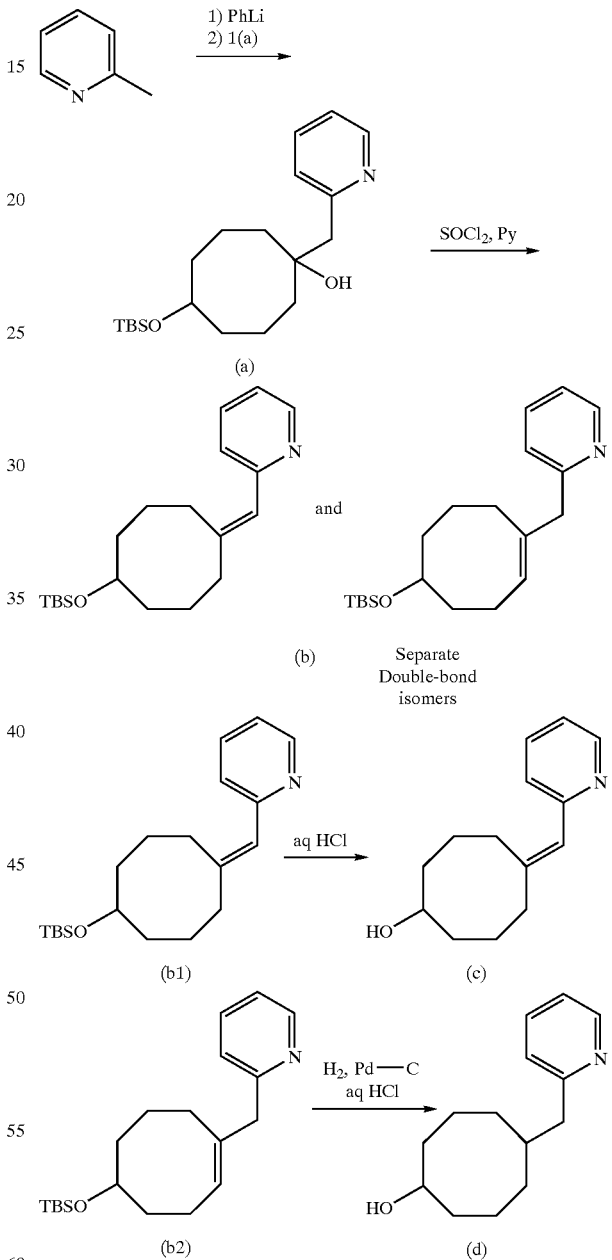

(a) 1-(2-Pyridylmethyl)-5-(tert-butyl) dimethylsilyloxy-1-cyclooctanol 14.5 ml of a phenyllithium solution (1.0 M) was added in 120 ml of anhydrous ether, and then the solution was cooled in an ice bath. To the reaction solution was added 1.4 g of 2-methylpyridine, followed by stirring at room temperature for fifty minutes and then cooling to 0° C. To the resulting solution was added 2.0 g of the product prepared in Reference Example 1 (a), and the reaction solution was stirred at room temperature for two hours. The reaction solution was poured into ice water and extracted with ether. The organic layer was washed with a saturated saline solution, and dried over anhydrous sodium sulfate, and the solvent was evaporated. The resulting crude product was purified by column chromatography on silica gel, and the eluate with ethyl acetate-hexane (1:5) was collected, to afford 1.3 g of the titled compound (a) as pale yellow liquid.

$^1$H-NMR δ(CDCl$_3$); 0.04, 0.05(s,6H), 0.88 (s,9H), 1.34–1.92(m, 12H), 2.86(s), 2.89(s,2H), 3.78–3.90(m,1H), 7.10–7.18, 7.30–7.38(m,2H), 7.62(t,J=7.6 Hz,1H), 8.47–8.51(m,1H).

(b1) (Tert-butyl)dimethyl{[5-(2-pyridylmethylene)-cyclooctyl]oxy}silane, and (b2) (tert-butyl)dimethyl{[5-(2-pyridylmethyl)-4-cyclooctenyl]oxy}silane 2.0 g of the above product (a) was treated in a manner similar to Reference Example 2 (c), to yield 0.53 g of (b1) (tert-butyl)dimethyl{[5-(2-pyridylmethylene)cyclooctyl]oxy}silane, and 1.2 g of (b2) (tert-butyl)dimethyl-{[5-(2-pyridylmethyl)-4-cyclooctenyl]oxy}silane as a colorless oily matter.

(b1) $^1$H-NMR δCDCl$_3$; −0.04(s,6H), 0.84(s,9H), 1.44–2.00(m, 8H), 2.26–2.40(m,3H), 3.06–3.16(m,1H), 3.89–3.96(m,1H), 6.36(s, 1H), 7.04(m,1H), 7.16(d,J=8.0 Hz,1H), 7.59(dt,J=2.0,8.0 Hz,1H), 8.56(dd,J=2.0,4.0 Hz,1H).

(b2) $^1$H-NMR δCDCl$_3$; 0.01(s,6H), 0.87(s,9H), 1.16–1.34 (m, 2H), 1.48–1.80(m,4H), 1.94–2.10(m,2H), 2.18–2.35(m, 2H), 3.42–3.52(m,2H), 3.69–3.76(m,1H), 6.36(t,J=8.0 Hz,1H), 7.08–7.14(m,1H), 7.18(d,J=7.6 Hz,1H), 7.59(dt,J= 2.0 Hz,7.6 Hz,1H), 8.53(d, J=4.8 Hz,1H).

(c) 5-(2-Pyridylmethylene)-1-cyclooctanol 0.53 g of (tert-butyl)dimethyl{[5-(2-pyridylmethylene) cyclooctyl]oxy}silane obtained in the above item (b1) was treated in a manner similar to Reference Example 1 (d), to yield 0.38 g of the titled compound (c) as a colorless oily matter.

$^1$H-NMR δ(CDCl$_3$); 1.44–1.78(m,6H), 1.82–2.00(m,2H), 2.30–2.52(m,3H), 2.95–3.04(m,1H), 3.89–3.96(m,1H), 6.37 (s,1H), 7.04(dt, J=5.2 Hz,7.6 Hz,1H), 7.16(d,J=8.0 Hz,1H), 7.60(dt,J=2.4,7.6 Hz, 1H), 8.57(d,J=5.2 Hz,1H).

(d) 5-(2-Pyridylmethyl)-1-cyclooctanol 1.2 g of (tert-butyl)dimethyl{[5-(2-pyridylmethyl)-4-cyclooctenyl]oxy}silane obtained in the above item (b2) was dissolved in 50 ml of ethanol. To the solution was added 2 ml of 5N HCl. 0.5 g of 10% palladium-carbon were added and suspended in the solution. The reaction solution was stirred under hydrogen atmosphere at three atmosphere pressure for four hours. The catalyst was removed by filtration, and the filtrate was neutralized with 2 ml of 5N sodium hydrochloride, and the solvent was evaporated under reduced pressure. The residue was dissolved in ethyl acetate, washed with water and a saturated saline solution, and dried over anhydrous sodium sulfate. The solvent was evaporated, to afford 0.66 g of the title compound (d) above as a colorless oily matter.

$^1$H-NMR δ(CDCl$_3$); 0.01 (s,6H), 0.87 (s,9H), 1.19–1.92 (m,10H), 1.96–2.18(m,2H), 2.18–2.35(m,2H), 2.65–2.72(m, 1H), 3.54–3.59(m,1H), 3.74–3.84(m,1H), 3.90–3.97(m,1H), 7.06–7.16(m, 2H), 7.58(t, J=7.6 Hz, 1H), 8.53(d, J=4.8 Hz, 1H).

Reference Example 5

5-[2-[(4-Methoxybenzyl)oxy]-2-(2-methoxymethoxyphenyl)ethyl]-1-cyclooctanol

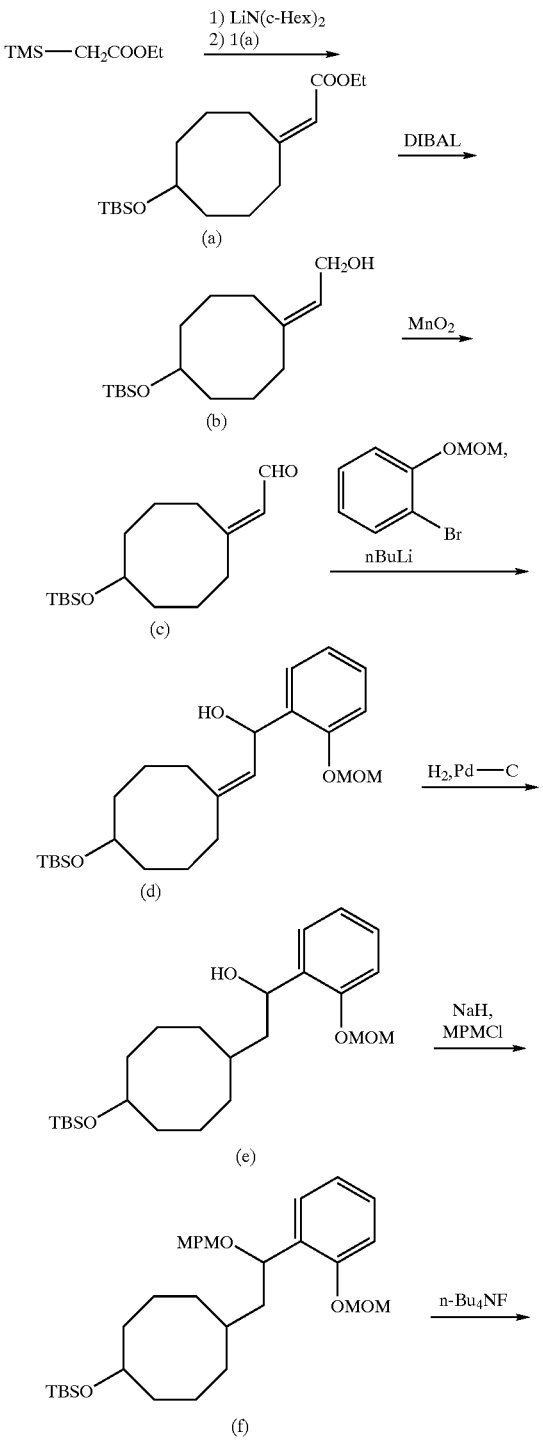

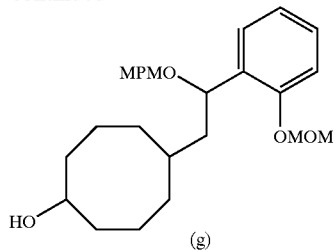

(g)

(a) Ethyl 2-[5-(tert-butyl)dimethylsilyloxy-1-cyclooctylidene]acetate 9.8 ml of dicyclohexylamine was dissolved in 150 ml of anhydrous tetrahydrofuran. The reaction solution was cooled to −70° C. To the solution was added 14 ml of a solution (1.6M) of n-butyllithium in hexane. The solution was stirred at the temperature in the range from −70° C. to −50° C. for twenty minutes. To the reaction solution was added 9.1 ml of ethyl 2-trimethylsilylacetate. The reaction solution was stirred at the temperature in the range from −70° C. to −50° C. for further one hour. Then, to the solution was added 4.9 g of the product prepared in Reference Example 1 (a). The solution was stirred at −70° C. for one hour and warmed to 0° C. and stirred at 0° C. for further thirty minutes. To the reaction solution was added 1.0 g of sodium hydrogensulfate monohydrate. The solution was stirred at room temperature for ten minutes. The reaction solution was poured into ice water, and to the solution was added 1N HCl until pH of the solution was reached at 5. The reaction solution was extracted with ether. The organic phase was washed with a saturated sodium bicarbonate aqueous solution and then a saturated saline solution, and dried over anhydrous sodium sulfate, and the solvent was evaporated. The residue was purified by column chromatography on silica gel, and the eluate with ethyl acetate-hexane (1:50) was collected, to afford 5.7 g of the titled product as a colorless oily matter.

$^1$H-NMR δ(CDCl$_3$); 0.00(s,3H), 0.12(s,3H), 0.86(s,9H), 1.29–1.30(m,3H), 1.44–1.78(m,6H), 1.88–2.00(m,2H), 2.18–2.38(m,3H), 2.65–2.72(m,1H), 3.14–3.22(m,1H), 3.76–3.85(m,1H), 4.06–4.18(m,3H), 5.73(s, 1H).

(b) 2-[5-(Tert-butyl)dimethysilyloxy-1-cyclooctylidene]ethanol 5.7 g of the above product (a) was dissolved in 150 ml of toluene, and the solution was cooled to −50° C. To the solution was added 20 ml of a solution (1.0M) of diisobutyl aluminum lithium hydride (DIBAL) in toluene. The solution was stirred at −50° C. for one hour. To the reaction solution was added 26 ml of DIBAL solution, followed by stirring for further twenty minutes. Then, to the reaction solution was added 50 ml of a saturated ammonium chloride solution, followed by stirring at room temperature for ten minutes. To the reaction solution was added 10 g of Rochelle salt, followed by stirring for further thirty minutes and filtering through Celite. The filtrate was washed with a saturated Rochelle salt solution and a saturated saline solution, and dried over anhydrous sodium sulfate, and the solvent was evaporated. The residue was purified by column chromatography on silica gel, and the eluate with ethyl acetate-hexane (1:8) was collected, to afford 3.9 g of the titled compound (b) as a colorless oily matter.

$^1$H-NMR δ(CDCl$_3$); 0.01(s,3H), 0.03(s,3H), 0.87(s,9H), 1.38–1.86(m,8H), 2.01–2.25(m,3H), 2.32–2.40(m,1H), 3.84–3.92(m,1H), 4.08–4.23(m,2H), 5.47(t,J=6.8 Hz,1H).

(c) 2-[5-(Tert-butyl)dimethylsilyloxy-1-cyclooctylidene]-acetaldehyde 3.9 g of the above product (b) was dissolved in 150 ml of dichloromethane. To the solution was added 44 g of manganese dioxide while stirring at room temperature. After completion of adding the reagent, the reaction solution was stirred at room temperature for three days. The reaction solution was filtered and the filtrate was concentrated to afford 3.0 g of the titled product (c) as a colorless oily matter.

$^1$H-NMR δ(CDCl$_3$); 0.00(s,3H), 0.04(s,3H), 0.86(s,9H), 1.54–1.78(m,6H), 1.90–2.12(m,2H), 2.28–2.47(m,3H), 2.97–3.06(m, 1H), 3.78–3.86(m,1H), 5.93(d,J=8.0 Hz,1H), 10.01(d,J=8.0 Hz,1H).

(d) 2-[5-(Tert-butyl)dimethylsilyloxy-1-cyclooctylidene]-1-[(2-methoxymethoxy)phenyl]-1-ethanol 5.0 g of 1-bromo-(2-methoxymethoxy)benzene was dissolved in 150 ml of anhydrous tetrahydrofuran. The reaction solution was cooled to −70° C. To the solution was added 7.0 ml of a solution (3.0M) of n-butyllithium in hexane. The reaction solution was stirred for fifty minutes while warming from −70° C. to −5° C. and then the reaction solution was cooled to −70° C., again. Then, to the reaction solution was added 3.0 g of the above product (c). The solution was stirred at the temperature in the range from −70° C. to −40° C. for ninety minutes. The reaction solution was poured into water and extracted with ether. The organic layer was washed with a saturated saline solution, and dried over anhydrous sodium sulfate. The solvent was evaporated. The residue was purified by column chromatography on silica gel, and the eluate with ethyl acetate-hexane (1:20) was collected, to afford 2.7 g of the titled compound (d) as a pale yellow oily matter.

$^1$H-NMR δ(CDCl$_3$); 0.04(s,6H), 0.88(s,9H), 1.49–1.92 (m,8H), 2.06–2.16(m,2H), 2.40–2.56(m,2H), 3.49(s,3H), 3.93–4.00(m,1H), 5.21–5.29(m,2H), 5.53(br.d,J=8.8 Hz,1H), 5.64–5.70(m,1H), 7.01 (t,J=7.4 Hz,1H), 7.09(d,J=8.0 Hz,1H), 7.21(t,J=8.0 Hz, 1H), 7.39 (d,J=7.4 Hz,1H).

(e) 2-[5-(Tert-butyl)dimethylsilyloxy-1-cyclooctyl]-1-[(2-methoxymethoxy)phenyl]-1-ethanol 2.7 g of the above product (d) was dissolved in 100 ml of ethyl acetate, and in the solution was suspended 0.28 g of 10% palladium-carbon. The suspension was stirred under hydrogen atmosphere for two hours. The catalyst was removed by filtration, and the filtrate was evaporated, to afford 2.5 g of the titled compound (e) as a colorless oily matter.

$^1$H-NMR δ(CDCl$_3$); 0.00(s,3H), 0.04(s,3H), 0.87(s,9H), 1.40–2.00(m,10H), 2.08–2.42(m,4H), 2.48–2.56(m,1H), 3.48(s,3H), 3.72–3.82(m,1H), 5.02–5.12(m,1H), 5.17–5.28 (m,2H), 5.52–5.60(m,1H), 7.00(t,J=7.4 Hz,1H), 7.05(d,J=8.0 Hz,1H), 7.20(t,J=8.0 Hz,1H), 7.44(d,J=7.4 Hz,1H).

(f) (Tert-butyl)[(5-{2-[(4-methoxybenzyl)oxy]-2-(2-methoxymethoxyphenyl)ethyl}cyclooctyl)oxy]dimethylsilane 2.5 g of the above product (e) was dissolved in 30 ml of dimethylformamide. To the solution was added 0.36 g of sodium hydride (60%). The reaction solution was stirred at 0° C. for thirty minutes. To the reaction solution was added 1.3 ml of 4-methoxybenzylchloride, followed by stirring for two hours and at 40° C. for further two hours. The reaction solution was poured into water, extracted with ether, washed with a saturated saline solution, and dried over anhydrous sodium sulfate. The solvent was evaporated. The residue was subject to column chromatography on silica gel, and the eluate with ethyl acetate-hexane (1:30) was collected, to afford 1.8 g of the titled product (f) as a pale yellow oily matter.

$^1$H-NMR δ(CDCl$_3$); 0.00(s,3H), 0.02(s,3H), 0.87(s,9H), 1.24–1.80(m,10H), 1.84–2.40(m,5H), 3.46(s,3H), 3.68–3.78 (m,1H), 3.80(s,3H), 4.18–4.46(m,2H), 4.86–4.98(m,1H), 5.12–5.22(m,2H), 5.44–5.50(m,1H), 6.82–6.90(d,J=7.4 Hz,2H), 7.00–7.09(m,2H), 7.15–7.30(m,3H), 7.49(d,J=7.4 Hz,1H).

(g) 5-[2-[(4-Methoxybenzyl)oxy]-2-(2-methoxymethoxyphenyl)ethyl]-1-cyclooctanol 1.8 g of the above product (f) was treated in a manner similar to Reference Example 2 (f), to yield 1.3 g of the titled compound (g) as a colorless oily matter.

$^1$H-NMR δ(CDCl$_3$); 1.42–1.90(m,10H), 1.98–2.40(m, 5H), 3.47(s,3H), 3.69–3.78(m,1H), 3.80(s,3H), 4.17–4.24 (m,1H), 4.34–4.42(m,1H), 4.92–4.99(m,1H), 5.17–5.22(m, 2H), 5.43–5.52(m,1H), 7.04–7.11(m,2H), 7.18–7.25(m,3H), 7.46–7.51(m,1H).

Reference Example 6

5-Hydroxycyclooctyl (4-methoxy-2-methoxymethoxy)benzoate

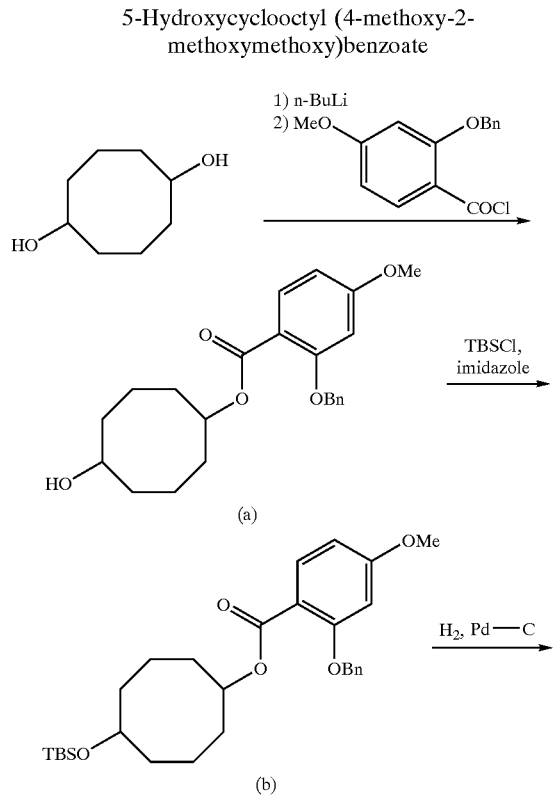

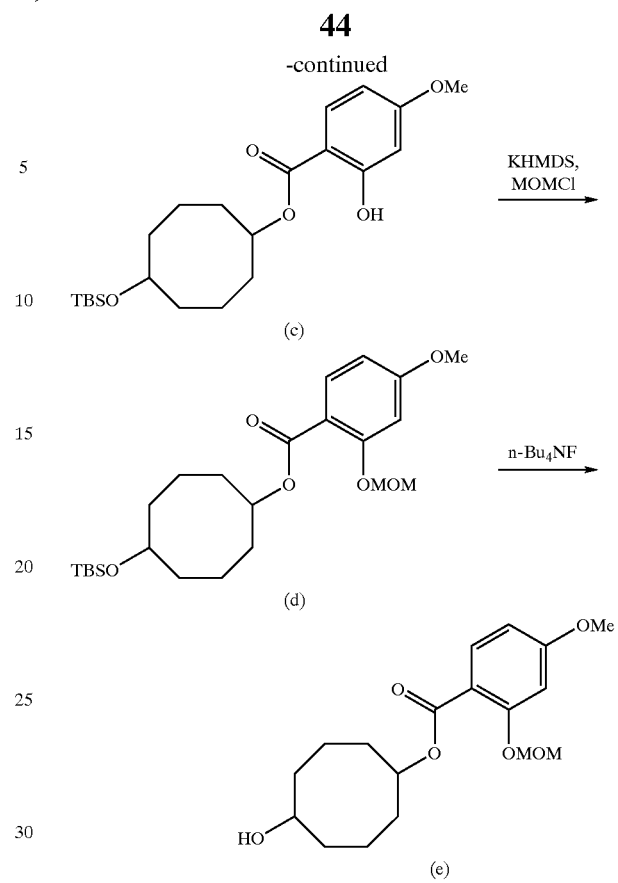

(a) 5-Hydroxycyclooctyl 2-benzyloxy-4-methoxy)benzoate 2.4 g of 1,5-cyclooctanediol was dissolved in 150 ml of tetrahydrofuran. To the solution was added 11.5 ml of a solution (1.6 M)of n-butyllithium in hexane at –50° C. The solution was stirred at –50° C. for ten minutes. To the reaction solution was added 3.0 g of (2-benzyloxy)-4-methoxybenzoylchloride synthesized from methyl (2-hydroxy-4-methoxy)benzoate according to the method well known in the art. The reaction solution was stirred for ninety minutes while warming from –50° C. to 0° C. The reaction solution was diluted with ether, washed with water and a saturated saline solution, and dried over anhydrous sodium sulfate. Then, the solvent was evaporated. The residue was subject to column chromatography on silica gel, and the eluate with ethyl acetate-hexane (1:5) was collected, to afford 2.5 g of the titled compound (a) as a colorless oily matter.

$^1$H-NMR δ(CDCl$_3$); 1.44–2.08(m,12H), 3.81(s,3H), 3.84–3.92(m,1H), 5.06–5.12(m,1H), 5.13(s,3H), 6.48–6.54 (m,2H), 7.27–7.42(m,3H), 7.49(d,J=7.2 Hz,2H), 7.83(d,J= 8.4 Hz,1H).

(b) 5-[(Tert-butyl)dimethylsilyloxy]cyclooctyl (2-benzyloxy-4-methoxy)benzoate 1.7 g of the above product (a) was dissolved in 60 ml of dimethylformamide. To the solution were added 0.6 g of imidazol and 1.0 g of tert-butylchlorodimethylsilane. The solution was stirred at room temperature overnight. The reaction solution was cooled on an ice bath, and then to the solution was added a saturated sodium bicarbonate aqueous solution. The reaction solution was extracted with diethylether, washed with a saturated saline solution, and dried over anhydrous sodium sulfate. The solvent was evaporated. The residue was purified by column chromatography on silica gel, and the eluate with ethyl acetate-hexane (1:30) was collected, to afford 2.1 g of the titled compound (b) as colorless liquid.

$^1$H-NMR δ(CDCl$_3$); 0.05(s), 0.10(s,6H), 0.89(s), 0.91(s, 9H), 1.40–1.94(m,12H), 3.80(s,3H), 3.82–3.88(m,1H), 5.05–5.12(m, 1H), 5.14(s,2H), 6.48–6.52(m,2H), 7.28–7.41 (m,3H), 7.49(d,J=7.0 Hz,2H), 7.84(d,J=8.8 Hz,1H).

(c) 5-[(Tert-butyl)dimethylsilyloxy]cyclooctyl (2-hydroxy-4-methoxy)benzoate 0.60 g of the above product (b) was treated in a manner similar to Reference Example 1, to afford 0.48 g of the titled compound (c) as colorless liquid.

$^1$H-NMR δ(CDCl$_3$); 0.05(s), 0.10(s,6H), 0.89(s), 0.91(s, 9H), 1.44–1.94(m,12H), 3.82(s,3H), 3.83–3.89(m,1H), 5.05–5.12(m,1H), 6.40–6.46(m,2H), 7.73(d,J=8.4 Hz,1H), 11.15(s,1H).

(d) 5-[(Tert-butyl)dimethylsilyloxy]cyclooctyl-(4-methoxy-2-methoxy methoxy)benzoate 2.2 g of the above product (c) was dissolved in 100 ml of tetrahydrofuran. To the solution was added 11 ml of a solution (0.5M) of potassium bis(trimethylsilyl)amide in toluene. The reaction solution was stirred –70° C. for twenty minutes. Then, to the reaction solution was added 0.45 ml of chloromethylmethylether. The solution was stirred for ninety minutes while warming from –70° C. to room temperature. The reaction solution was diluted with ether, washed with water and a saturated saline solution, and dried over anhydrous sodium sulfate. The solvent was evaporated. The residue was purified by column chromatography on silica gel, and the eluate with ethyl acetate-hexane (1:20) was collected, to afford 2.0 g of the titled compound(d) as a colorless oily matter.

$^1$H-NMR δ(CDCl$_3$); 0.05(s,6H), 0.89(s), 0.91(s,9H), 1.46–1.98(m,12H), 3.52(s,3H), 3.82(s,3H), 3.85–3.90(m, 1H), 5.04–5.12(m,1H), 5.24(s,3H), 6.56(dd,J=2.4 Hz,8.4 Hz,1H), 6.72(d, J=2.4 Hz, 1H), 7.80(d,J=8.4 Hz,1H).

(e) 5-Hydroxycyclooctyl (4-methoxy-2-methoxymethoxy)benzoate 2.2 g of the above product (d) was treated in a manner similar to Reference Example 2 (f), to yield 1.5 g of the titled compound (e) as a colorless oily matter.

$^1$H-NMR δ(CDCl$_3$); 1.52–2.00(m,12H), 3.52(s,3H), 3.83 (s,3H), 3.86–3.90(m,1H), 5.04–5.12(m,1H), 5.24(s,2H), 6.56(dd,J=2.4 Hz, 8.4 Hz,1H), 6.72(d,J=2.4 Hz,1H), 7.80(d, J=8.4 Hz,1H).

Example 1

5-Benzyl-1-cyclooctanone 1.3 g of 5-benzyl-1-cyclooctanol prepared in the aforementioned Reference Example 1 was dissolved in 40 ml of acetone. To the solution was added 2.5 ml Jones reagent which was prepared in the ratio of 11.5 ml of sulfuric acid, 13 g of chromic acid and 20 ml of water. The reaction solution was stirred at room temperature for twenty minutes. To the reaction solution was added 2 ml of 2-propanol, followed by filtration through Celite. The residue was washed with dichloromethane and the washing liquid was combined with the filtrate. The filtrate was washed with water and a saturated saline solution, and dried over anhydrous sodium sulfate. The solvent was evaporated. The crude product was subject to column chromatography on silica gel, and the eluate with ethyl acetate-hexane (1:15) was collected, to afford 1.23 g of the titled compound as colorless liquid.

$^1$H-NMR δ(CDCl$_3$); 1.30–1.70(m,4H), 1.96–2.06(m,2H), 2.20–2.28(m,2H), 2.48(d,J=7.2 Hz,2H), 2.52–2.60(m,2H), 7.10(d,J=6.4 Hz, 2H), 7.16(d,J=7.6 Hz,1H), 7.22–7.28(m, 2H).

Example 2

5-Phenethyl-1-cyclooctanone

A 5-substituted 1-cyclooctanol derivative was synthesized in a manner similar to Reference Example 1, and oxidized in a manner similar to Example 1, to yield the titled compound of the present invention.

$^1$H-NMR δ(CDCl$_3$); 1.32–1.67(m,7H), 1.68–1.80(m,2H), 2.04–2.16(m,2H), 2.24–2.32(m,2H), 2.52–2.63(m,4H), 7.11–7.18(m,3H), 7.23–7.29(m,2H).

Example 3

5-(3-Phenylpropyl)-1-cyclooctanone

A 5-substituted 1-cyclooctanol derivative was synthesized in a manner similar to Reference Example 1, and oxidized in a manner similar to Example 1, to yield the titled compound.

$^1$H-NMR δ(CDCl$_3$); 1.18–1.90(m,11H), 1.96–2.30(m, 4H), 2.52–2.63(m,4H), 7.12–7.29(m,5H).

Example 4

5-Benzyl-2-cycloocten-1-one 1.2 g of 5-benzyl-1-cyclooctanone prepared in Example 1 was dissolved in 50 ml of ethyl acetate. To the solution was added 1.25 g of phenylselenenylchloride. The reaction solution was stirred at room temperature for forty minutes. To the reaction solution was added 10 ml of water, followed by stirring for three minutes. The organic layer was separated. To the organic layer were added 20 ml of tetrahydrofliran and 1.4 ml of 30% hydrogen peroxide. The reaction solution was stirred at room temperature for two and a half hours. Then, the organic layer was washed with water and a saturated sodium bicarbonate aqueous solution, and dried over anhydrous sodium sulfate. The solvent was evaporated. The crude product was subject to column chromatography on silica gel, and the eluate with ethyl acetate-hexane (1:10) was collected, to afford 0.71 g of the titled compound as colorless liquid.

$^1$H-NMR δ(CDCl$_3$); 1.30–1.76(m,4H), 1.94–2.08(m,2H), 2.31–2.40(m,1H), 2.48–2.80(m,4H), 6.11(d,J=12 Hz,1H), 6.37(dt,J=12 Hz, 7.7 Hz,1H), 7.12–7.16(m,2H), 7.20–7.23 (m,1H), 7.26–7.31 (m,2H).

Example 5

5-Phenethyl-2-cycloocten-1-one

The 5-phenethyl-1-cyclooctanone derivative obtained in Example 2 was treated in a manner similar to Example 4, to yield the titled compound.

$^1$H-NMR δ(CDCl$_3$); 1.34–1.80(m,5H), 1.90–2.02(m,1H), 2.36–2.44 (m,1H), 2.56–2.75(m,6H), 6.10(d,J=12 Hz,1H), 6.38 (dt,J=12 Hz, 7.8 Hz,1H), 7.12–7.31(m,5H).

Example 6

5-(3-Phenylpropyl)-2-cycloocten-1-one

A 5-(3-phenylpropyl)-1-cyclooctanone derivative obtained in Example 3 was treated in a manner similar to Example 4, to yield the titled compound.

$^1$H-NMR δ(CDCl$_3$); 1.30–1.40(m,2H), 1.52–1.76(m,4H), 1.84–2.03(m,1H), 2.30–2.52(m,2H), 2.54–2.74(m,6H), 6.07 (d,J=12 Hz,1H), 6.37(dt,J=12 Hz,7.8 Hz,1H), 7.15–7.32(m, 5H).

Example 7

5-Benzyl-8-hydroxy-2-cycloocten-1-one 0.12 ml of diisopropylamine was dissolved in 10 ml of tetrahydrofuran. To the solution was added 0.52 ml of a solution (1.6 M) of n-butyllithium in hexane at −30° C. The solution was stirred at temperature in the range from −30° C. to −10° C. for twenty minutes and cooled to −50° C. To the solution was added a solution of 0.15 g of 5-benzyl-2-cyclooctene-1-one prepared in Example 4 dissolved in 3 ml of tetrahydrofuran. The reaction solution was stirred at temperature in the range of from −50° C. to −10° C. for fifteen minutes. To another reaction vessel charged with 30 ml ether was bubbled through Oxygen gas for ten minutes to saturation. To this was added dropwise the reaction solution described above. Oxygen gas was bubbled through the reaction solution during adding and for 90 minutes after adding while warming from −30° C. to 0° C. The reaction solution was poured into an aqueous saturated sodium sulfite solution. The organic layer was separated, washed with a saturated saline solution, and dried over anhydrous sodium sulfate. The solvent was evaporated. The crude product was subject to column chromatography on silica gel, and the eluate with ethyl acetate-hexane (1:10) was collected, to afford 20 mg and 25 mg of two forms of diastereomer of the titled compound as colorless liquid, respectively.

$^1$H-NMR δ(CDCl$_3$); 1.24–1.92(m,4H), 2.00–2.96(m,5H), 4.78(m,1H), 6.11(d,J=12 Hz,1H), 6.33(dt,J=12 Hz,7.7 Hz,1H), 7.01–7.32(m,5H).

Example 8

5-[2-(4-Methoxymethoxyphenyl)ethyl]-1-cyclooctanone 1.65 g of pyridinium dichromate was dissolved in 30 ml of dichloromethane. To the solution was added 0.40 g of 5-[2-(4-methoxymethoxyphenyl)ethyl]-1-cyclooctanol prepared in Reference Example 2. The reaction solution was stirred at room temperature for two hours. To the reaction solution was added another 2.5 g of pyridinium dichromate. The reaction solution was stirred at room temperature overnight. The reaction solution was diluted with 50 ml of ether and purified on Florisil column eluted with ether, to afford 0.37 g of the titled compound as colorless liquid.

$^1$H-NMR δ(CDCl$_3$); 1.32–1.64(m,7H), 1.68–1.80(m,2H), 2.04–2.15(m,2H), 2.24–2.32(m,2H), 2.47–2.63(m,4H), 3.48 (s,3H), 5.15(s,2H), 6.95(dd,J=2.4 Hz,8.4 Hz,2H), 7.05(d,J= 8.4 Hz,2H).

Example 9

5-[2-(2-Methoxymethoxyphenyl)ethyl]-1-cyclooctanone

A 5-substituted 1-cyclooctanol derivative was synthesized in a manner similar to Reference Example 2, and oxidized in a manner similar to Example 8, to yield the titled compound.

$^1$H-NMR δ(CDCl$_3$); 1.32–1.67(m,7H), 1.70–1.80(m,2H), 2.04–2.16 (m,2H), 2.24–2.32(m,2H), 2.54–2.63(m,4H), 3.48(s,3H), 5.19 (s,2H), 6.92(dt,J=1.4 Hz,7.2 Hz,1H), 7.04 (dd,J=1.4 Hz,8.0 Hz, 1H), 7.08–7.15(m,2H).

Example 10

5-[2-(3-Methoxymethoxyphenyl)ethyl]-1-cyclooctanone

A 5-substituted 1-cyclooctanol derivative was synthesized in a manner similar to Reference Example 2, and oxidized in a manner similar to Example 8, to yield the titled compound.

$^1$H-NMR δ(CDCl$_3$); 1.32–1.67(m,7H), 1.68–1.80(m,2H), 2.04–2.15(m,2H), 2.24–2.33(m,2H), 2.50–2.63(m,4H), 3.48 (s,3H), 5.17(s,2H), 6.76–6.86(m,3H), 7.18(t,J=8.0 Hz,1H).

Example 11

5-[2-(4-Methoxy-2-methoxymethoxyphenyl)ethyl]-1-cyclooctanone

A 5-substituted 1-cyclooctanol derivative was synthesized in a manner similar to Reference Example 2, and oxidized in a manner similar to Example 8, to yield the titled compound.

$^1$H-NMR δ(CDCl$_3$); 1.32–1.48(m,3H), 1.58–1.80(m,6H), 2.02–2.16 (m,2H), 2.24–2.33(m,2H), 2.46–2.64(m,4H), 3.47(s,3H), 3.77 (s,3H), 5.17(s,2H), 6.47(dt,J=2.4 Hz,7.6 Hz,1H), 6.66(d,J=2.4 Hz, 1H), 6.98(d,J=7.6 Hz,1H).

Example 12

5-[2-(4-Methoxymethoxyphenyl)ethyl]-2-cycloocten-1-one 30 ml of tetrahydrofuran was cooled at −70° C., and to this was added 2.0 ml of a solution (1.0 M) of lithium bis(trimethylsilyl)amide in tetrahydrofuran. The reaction solution was stirred at −70° C. for five minutes. Then, to the reaction solution was added 0.32 g of 5-[2-(4-methoxymethoxyphenyl)ethyl]-1-cyclooctanone prepared in Example 8, and the solution was stirred at −70° C. for one hour. Then, to the solution was added 0.40 g of phenylselenenyl bromide, the solution was stirred at temperature in the range from −70° C. to −20° C. for one and a half hours. To the reaction solution was added 50 ml of water. The resulting solution was extracted with ether. The organic layer was washed with a saturated saline solution, and dried over anhydrous sodium sulfate. The solvent was evaporated to afford 0.60 g of crude phenylselenenyl-addition product as a yellow oily matter.

The crude product was dissolved in a mixed solvent of 10 ml of dichloromethane and 4 ml of water, and to this were added 0.18 ml of pyridine and 1.0 ml of 30% hydrogen peroxide. The reaction solution was stirred at room temperature for forty minutes. The reaction solution was diluted with water, and extracted with dichloromethane. The extract was washed with a saturated sodium carbonate aqueous solution, and dried over anhydrous sodium sulfate. The solvent was evaporated. The residue was purified on silica gel, and the eluate with ethyl acetate-hexane (1:10) was collected, to afford 0.17 g of the titled compound as colorless liquid.

$^1$H-NMR δ(CDCl$_3$); 1.32–1.64(m,3H), 1.68–1.80(m,2H), 2.04–2.15 (m,2H), 1.95–2.01(m,1H), 2.38–2.44(m,1H), 2.54–2.72(m,4H), 3.48(s,3H), 5.16(s,2H), 6.09(d,J=12

Hz,1H), 6.39(dt,J=12 Hz, 8.0 Hz,1H), 6.96(d,J=8.4 Hz,2H), 7.08(d,J=8.4 Hz,2H).

Example 13

5-[2-(2-Methoxymethoxyphenyl)ethyl]-2-cycloocten-1-one

The compound of Example 9, 5-[2-(2-methoxymethoxyphenyl)-ethyl]-1-cyclooctanone was used, and treated in a manner similar to Example 12, to yield the titled compound.

$^1$H-NMR δ(CDCl$_3$); 1.37–1.80(m,6H), 1.90–2.14(m,1H), 2.38–2.50 (m,1H), 2.60–2.74(m,5H), 3.48(s,3H), 5.20(s, 2H), 6.09(d, J=12 Hz,1H), 6.41(dt,J=12 Hz,8.0 Hz, 1H), 6.93(t,J=7.2 Hz,1H), 7.06(d,J=8.0 Hz,1H), 7.10–7.18(m, 2H).

Example 14

5-[2-(3-Methoxymethoxyphenyl)ethyl]-2-cycloocten-1-one

The compound of Example 10, 5-[2-(3-methoxymethoxyphenyl)ethyl]-1-cyclooctanone was used, and treated in a manner similar to Example 12, to yield the titled compound.

$^1$H-NMR δ(CDCl$_3$); 1.34–1.48(m,1H), 1.56–1.78(m,5H), 1.90–2.02 (m,1H), 2.38–2.47(m,1H), 2.58–2.73(m,5H), 3.49(s,3H), 5.17 (s,2H), 6.10(d,J=12 Hz,1H), 6.39(dt,J=12 Hz,8.0 Hz,1H), 6.80–6.90(m,3H), 7.20(t,J=8.0 Hz,1H).

Example 15

5-[2-(4-Methoxy-2-methoxymethoxyphenyl)ethyl]-2-cycloocten-1-one

The compound of Example 11, 5-[2-(4-methoxy-2-methoxymethoxyphenyl)ethyl]-1-cyclooctanone was used, and treated in a manner similar to Example 12, to yield the titled compound.

$^1$H-NMR δ(CDCl$_3$); 1.38–1.80(m,6H), 1.88–2.10(m,1H), 2.38–2.52 (m,1H), 2.58(t,J=8.0 Hz,2H), 2.63–2.74(m,2H), 3.48(s,3H), 3.78 (s,3H), 5.19(s,2H), 6.09(d,J=12 Hz,1H), 6.40(dt,J=12 Hz,8.0 Hz, 1H), 6.48(dd,J=2.4 Hz,8.0 Hz,1H), 6.68(d,J=2.4 Hz.,1H), 7.01 (d,J=8.0 Hz,1H).

Example 16

5-[2-(4-Hydroxyphenyl)ethyl]-2-cycloocten-1-one 0.17 g of 5-[2-(4-methoxymethoxyphenyl)ethyl]-2-cyclooctene-1-one prepared in Example 12 was dissolved in 10 ml of 50% aqueous solution of trifluoroacetic acid. The resulting solution was stirred at room temperature for forty minutes. The reaction solution was cooled in an ice bath, and to the solution was added slowly 30 ml of a saturated sodium carbonate aqueous solution. Then, the reaction solution was extracted with ether. The extract was washed with a saturated sodium bicarbonate aqueous solution six times, and dried over anhydrous sodium sulfate. The solvent was evaporated. The residue was purified on silica gel column, and the eluate with ethyl acetate-hexane (1:6) was collected, to afford 0.077 g of the title compound above as colorless liquid.

$^1$H-NMR δ(CDCl$_3$); 1.35–1.78(m,6H), 1.88–2.08(m,1H), 2.36–2.74 (m,6H), 6.09(d,J=12 Hz,1H), 6.39(dt,J=12 Hz,7.6 Hz,1H), 6.76(d, J=8.4 Hz,2H), 7.03(d,J=8.4 Hz,2H).

Example 17

5-[2-(2-Hydroxyphenyl)ethyl]-2-cycloocten-1-one

The compound of Example 13, 5-[2-(2-methoxymethoxyphenyl)ethyl]-2-cycloocten-1-one was used, and treated in a manner similar to Example 16, to yield the titled compound.

$^1$H-NMR δ(CDCl$_3$); 1.37–1.80(m,6H), 1.90–2.18(m,1H), 2.30–2.90 (m,6H), 5.00–5.18(m,1H), 6.08(d,J=12 Hz,1H), 6.42(dt,J=12 Hz, 7.6 Hz,1H), 6.93(d,J=7.6 Hz,1H), 6.86(t, J=7.6 Hz,1H), 7.05–7.14 (m,2H).

Example 18

5-[2-(3-Hydroxyphenyl)ethyl]-2-cycloocten-1-one

The compound of Example 14, 5-[2-(3-methoxymethoxyphenyl)ethyl]-2-cycloocten-1-one was used, and treated in a manner similar to Example 16, to yield the titled compound.

$^1$H-NMR δ(CDCl$_3$); 1.34–1.48(m,1H), 1.56–1.80(m,4H), 1.90–2.02 (m,1H), 2.36–2.47(m,1H), 2.54–2.78(m,6H), 5.25(s,1H), 6.09(d, J=12 Hz,1H), 6.36–6.44(m,1H), 6.60–6.78(m,3H), 7.16(dt,J=7.6 Hz, 2.8 Hz, 1H).

Example 19

5-[2-(2-Hydroxy-4-methoxyphenyl)ethyl]-2-cycloocten-1-one

The compound of Example 15, 5-[2-(4-methoxy-2-methoxymethoxyphenyl)ethyl]-2-cycloocten-1-one was used, and treated in a manner similar to Example 16, to yield the titled compound.

$^1$H-NMR δ(CDCl$_3$); 1.38–1.80(m,6H), 1.82–2.10(m,1H), 2.38–2.74 (m,5H), 3.78(s,3H), 4.84–4.88(m,1H), 6.06(d,J= 12 Hz,1H), 6.30–6.48(m,2H), 6.68(d,J=2.4 Hz,1H), 7.01(d, J=8.0 Hz,1H).

Example 20

6-Benzyl-1-cyclodecanone

A 6-substituted 1-cyclodecanol derivative was synthesized in a manner similar to Reference Example 3, and oxidized in a manner similar to Example 1, to yield the titled compound.

$^1$H-NMR δ(CDCl$_3$); 1.22–1.28(m,4H), 1.38–1.60(m,5H), 1.65–1.78 (m,2H), 1.82–1.94(m,2H), 2.28–2.38(m,2H), 2.43(d,J=7.2 Hz,2H), 2.63–2.72(m,2H), 7.10–7.30(m,5H).

Example 21

6-Phenyl-1-cyclodecanone

A 6-substituted 1-cyclodecanol derivative was synthesized in a manner similar to Reference Example 3, and oxidized in a manner similar to Example 1, to yield the titled compound.

$^1$H-NMR δ(CDCl$_3$); 1.28–1.38(m,2H), 1.42–1.62(m,6H), 1.70–1.92 (m,4H), 2.28–2.34(m,2H), 2.41(quint,J=7.2 Hz,1H), 2.66–2.75(m, 2H), 7.10–7.30(m,5H).

Example 22

(a) Z-6-benzyl-2-cyclodecen-1-one, (b) E-6-benzyl-2-cyclodecen-1-one, and (c) 2Z,4E-6-benzyl-2,4-cyclodecadien-1-one 0.89 g of the compound of Example 20 was treated in a manner similar to the method in Example 12, and the resulting crude products were purified by column chromatography on silica gel, to yield (a) 0.13 g (15%) of Z-6-benzyl-2-cyclodecen-1-one, (b) 0.12 g (14%) of E-6-benzyl-2-cyclodecen-1-one, and (c) 0.03 g (3%) of 2Z,4E-6-benzyl-2,4-cyclodecadien-1-one as colorless liquid, respectively.

(a) Z-6-benzyl-2-cyclodecen-1-one $^1$H-NMR δ(CDCl$_3$); 0.88–1.14(m,2H), 1.38–1.78(m,6H), 1.96–2.08 (m,2H), 2.18–2.40(m,2H), 2.42–2.62(m,1H), 2.68–2.74(m,2H), 5.62(dt,J=4.8 Hz,12 Hz,1H), 6.23(d,J=12 Hz,1H) 7.06–7.26(m,5H).
(b) E-6-benzyl-2-cyclodecen-1-one
$^1$H-NMR δ(CDCl$_3$); 1.24–1.68(m,6H), 1.72–1.82(m,1H), 2.00–2.12 (m,1H), 2.40–2.60(m,4H), 2.62–2.74(m,1H), 6.18(t,J=7.6 Hz,1H), 6.56–6.70(m,1H), 7.08–7.32(m,5H).
(c) 2Z,4E-6-benzyl-2,4-cyclodecadien-1-one
$^1$H-NMR δ(CDCl$_3$); 1.24–1.66(m,4H), 1.70–2.26(m,4H), 2.30–2.72 (m,2H), 3.29(m,2H), 5.32(t,J=7.6 Hz,1H), 5.77 (d,J=16 Hz,1H), 6.56–6.70(m,1H), 7.08–7.32(m,5H).

Example 23

(a) Z-6-phenyl-2-cyclodecen-1-one, and (b) E-6-phenyl-2-cyclodecen-1-one 0.45 g of the compound of Example 21 was treated in a manner similar to Example 12, and then the resulting crude product was purified by column chromatography on silica gel, to yield 0.16 g of (a) Z-6-phenyl-2-cyclodecen-1-one and 0.16 g of (b) E-6-phenyl-2-cyclodecen-1-one as colorless liquid, respectively.
(a) Z-6-phenyl-2-cyclodecen-1-one
$^1$H-NMR δ(CDCl$_3$); 1.30–1.40(m,4H), 1.44–1.82(m,3H), 2.10–2.32 (m,3H), 2.52–2.68(m,2H), 2.88–3.02(m,1H), 5.87(dt,J=5.2 Hz, 12 Hz,1H), 6.41(d,J=12 Hz,1H), 7.12–7.32(m,5H).
(b) E-6-phenyl-2-cyclodecen-1-one
$^1$H-NMR δ(CDCl$_3$); 1.24–1.76(m,4H), 1.82–2.06(m,3H), 2.10–2.32 (m,2H), 2.48–2.74(m,4H), 6.42(d,J=16 Hz, 1H), 6.64–6.75(m,1H), 7.08–7.32(m,5H).

Example 24

5-[(2-Pyridyl)methylene]-1-cyclooctanone 0.38 g of 5-(2-pyridyl)methylene-1-cyclooctanol obtained in Reference Example 4 (c) was oxidized in a manner similar to Example 8, to yield 0.20 g of the titled compound as colorless liquid.
$^1$H-NMR δ(CDCl$_3$); 1.94–2.02(m,2H), 2.12–2.20(m,2H), 2.37–2.46 (m,5H), 2.83(d,J=6.0 Hz,2H), 6.29(s,1H), 7.03–7.11(m,2H), 7.58(dt,J=2.0 Hz,7.6 Hz,1H), 8.54(d,J= 4.8 Hz,1H).

Example 25

5-(2-Pyridyl)methylene-2-cycloocten-1-one 0.18 g of the compound obtained in Example 24 was treated in a manner similar to Example 12, to yield 0.016 g of the titled compound as colorless liquid.
$^1$H-NMR δ(CDCl$_3$); 1.54–2.10(m,2H), 2.30–2.88(m,2H), 2.92–3.02 (m,3H), 3.24(d,J=4.8 Hz,1H), 5.90(d,J=12 Hz,1H), 6.33(dt,J=12 Hz, 5.6 Hz,1H), 6.45(s,1H), 7.05–7.20 (m,2H), 7.58–7.68(m,1H), 8.57(d,J=5.2 Hz,1H).

Example 26

5-(2-Pyridylmethyl)-1-cyclooctanone 0.66 g of 5-(2-pyridyl)methyl-1-cyclooctanol obtained in Reference Example 4 (d) was oxidized in a manner similar to Example 8, to yield 0.41 g of the titled compound as colorless liquid.
$^1$H-NMR δ(CDCl$_3$); 1.37–1.46(m,2H), 1.58–1.72(m,5H), 1.97–2.08 (m,2H), 2.24–2.32(m,2H), 2.52–2.61 (m,2H), 2.68(d,J=7.2 Hz,2H), 7.07–7.13(m,2H), 7.58(t,J=7.6 Hz,1H), 8.50(d,J=5.2 Hz,1H).

Example 27

5-(2-Pyridyl)methyl-2-cycloocten-1-one 0.40 g of the compound obtained in Example 26 was treated in a manner similar to Example 12, to yield 4.0 mg of the titled compound as colorless liquid.
$^1$H-NMR δ(CDCl$_3$); 1.30–1.76(m,4H), 1.94–2.08(m,2H), 2.31–2.40 (m,1H), 2.48–2.80(m,4H), 6.09(d,J=12 Hz,1H), 6.37(dt,J=12 Hz, 7.7 Hz,1H), 7.07–7.13(m,2H), 7.58(t,J=7.6 Hz,1H), 8.52(d, J=5.2 Hz,1H).

Example 28

5-[2-[(4-Methoxybenzyl)oxy]-2-(2-methoxymethoxy-phenyl)ethyl]-1-cyclooctanone 1.3 g of the product of Reference Example 5 was oxidized in a manner similar to Example 8, to yield 1.1 g of the titled compound as colorless liquid.
$^1$H-NMR δ(CDCl$_3$); 1.58–1.64(m,2H), 2.18–2.48(m, 12H), 3.46(s, 3H), 3.80(s,3H), 4.20(d,J=11 Hz,1H), 4.39(d, J=11 Hz,1H), 5.10(q, J=4.0 Hz,1H), 5.17–5.22(m,2H), 6.86 (d,J=8.4 Hz,2H), 7.02–7.11(m, 2H), 7.18–7.25(m,3H), 7.47 (dd,J=1.6 Hz,7.6 Hz,1H).

Example 29

5-[2-[(4-Methoxybenzyl)oxy]-2-(2-methoxymethoxy-phenyl)ethyl]-2-cycloocten-1-one 1.1 g of the compound obtained in Example 28 was treated in a manner similar to Example 12, to yield 0.79 g of the titled compound as colorless liquid.
$^1$H-NMR δ(CDCl$_3$); 1.28–1.38(m,2H), 2.00–2.38(m,5H), 2.50–2.64 (m,4H), 3.47(s,3H), 3.80(s,3H), 4.18(d,J=11 Hz,1H), 4.42(d, J=11 Hz,1H), 5.04(q,J=4.0 Hz,1H), 5.20(s, 2H), 5.86(d,J=12 Hz,1H), 6.43(dd,J=5.6 Hz,12 Hz,1H), 6.84 (d,J=8.0 Hz,2H), 7.05–7.14(m,2H), 7.18(d,J=8.0 Hz,2H), 7.22–7.28(m,1H), 7.50(dd,J=6.0 Hz,1H).

Example 30

5-[2-Hydroxy-2-(2-methoxymethoxyphenyl)ethyl]-2-cycloocten-1-one 84 mg of the compound obtained in Example 29 was dissolved in a mixed solvent of 5 ml of dichloromethane and 5 ml of phosphate buffer (pH 6.8). To the resulting solution was added 0.10 g of 2,3-dichloro-5,6-dicyano-1,4-benzoquinone (DDQ). The solution was stirred at room temperature for three and a half hours. The reaction solution was diluted with dichloromethane, washed with a saturated sodium bicarbonate aqueous solution, and dried over anhydrous sodium sulfate. Then, the solvent was evaporated. The residue was purified on silica gel column, and the eluate with ethyl acetate-hexane (1:4) was collected, to afford 49 mg of the titled compound as colorless liquid.
$^1$H-NMR δ(CDCl$_3$); 1.28–1.38(m,2H), 2.00–2.38(m,5H), 2.50–2.76 (m,4H), 3.50(s,3H), 5.19(q,J=4.0 Hz,1H), 5.24(s, 2H), 5.89(d, J=12 Hz,1H), 6.14(d,J=4.8 Hz, 1H), 6.45(dd, J=6.0 Hz,12 Hz, 1H), 7.04(t,J=7.6 Hz, 1H), 7.10(d,J=8.0 Hz,1H), 7.22–7.28(m,1H), 7.41 (d,J=7.2 Hz, 1H).

Example 31

5-[2-(2-Methoxymethoxyphenyl)-2-oxoethyl]-2-cycloocten-1-one 25 mg of the compound obtained in Example 30 was treated in a manner similar to Reference Example 5 (c), to yield 20 mg of the titled compound as colorless liquid.
$^1$H-NMR δ(CDCl$_3$); 1.28–1.38(m,2H), 2.00–2.40(m,5H), 2.48–2.76 (m,4H), 3.50(s,3H), 5.24(s,2H), 5.89(d,J=12 Hz,1H), 6.14(d, J=4.8 Hz,1H), 6.45(dd,J=6.0 Hz,12 Hz,1H), 7.02–7.18(m,2H), 7.60 (t,J=6.0 Hz,1H), 8.03(dd,J=1.6 Hz,8.0 Hz,1H).

Example 32

5-[2-[4-Methoxy-2-methoxymethoxyphenyl]]2-oxoethyl]-2-cycloocten-1-one

The compound obtained in Example 11 was treated in a manner similar to the method for producing phenylselenenyl-addition described in the former section of Example 12, to generate 0.15 g of phenylselenenyl compound. Then, 0.15 g of the phenylselenenyl compound was treated in a manner similar to Example 30 and further treated in a manner similar to the latter section of Example 12, to afford 21 mg of the titled compound as colorless liquid.

$^1$H-NMR δ(CDCl$_3$); 1.38–1.54(m,3H), 1.62–2.02(m,4H), 2.40–2.52(m,2H), 2.64–2.98(m,4H), 3.51(s,3H), 3.85(s,3H), 5.26 (s,2H), 6.14(d,J=12 Hz,1H), 6.40(dt,J=12 Hz,12 Hz,1H), 6.59(dd, J=2.0 Hz,8.4 Hz,1H), 6.70(d,J=2.0 Hz., 1H), 7.75(d,J=7.2 Hz,1H).

Example 33

5-Oxocyclooctyl (4-methoxy-2-methoxymethoxy)benzoate 1.5 g of the compound obtained in Reference Example 6 was oxidized in a manner similar to Example 8, to yield 1.29 g of the titled compound as colorless liquid.

$^1$H-NMR δ(CDCl$_3$); 1.83–2.10(m,8H), 2.38–2.47(m,2H), 2.52–2.62 (m,2H), 3.52(s,3H), 3.83(s,3H), 4.85–4.94(m,1H), 5.24(s,2H), 6.56(dd,J=2.4 Hz,8.4 Hz,1H), 6.72(d,J=2.4 Hz,1H), 7.79(d,J=8.4 Hz, 1H).

Examples 34–39

A benzoate derivative was synthesized in a manner similar to Reference Example 6, and oxidized in a manner similar to Example 8, to yield the following compounds (Examples 34–39).

Example 34

5-Oxocyclooctyl (2-methoxymethoxy)benzoate $^1$H-NMR δ(CDCl$_3$); 1.87–2.12(m,8H), 2.40–2.48(m,2H), 2.54–2.62 (m,2H), 3.51(s,3H), 4.87–4.94(m,1H), 5.24(s, 2H), 7.04(t, J=7.6 Hz,1H), 7.18(d,J=7.6 Hz,1H), 7.46(dt,J= 1.8 Hz,7.6 Hz,1H), 7.74(dd,J=1.8 Hz,7.6 Hz,1H).

Example 35

6-Oxocyclodecyl benzoate $^1$H-NMR δ(CDCl$_3$); 1.52–1.76(m,8H), 1.82–2.04(m,4H), 2.33–2.41 (m,2H), 2.83–2.91(m,2H), 4.28–4.35(m,1H), 5.42(q,J=6.0 Hz,1H), 7.44(t,J=7.6 Hz,2H), 7.56(t,J=7.6 Hz,1H), 8.02(d,J=7.2 Hz,2H).

Example 36

6-Oxocyclodecyl (2-methoxymethoxy)benzoate $^1$H-NMR δ(CDCl$_3$); 1.54–1.76(m,8H), 1.83–2.10(m,4H), 2.31–2.40 (m,2H), 2.83–2.91(m,2H), 3.51(s,3H), 5.25(s, 2H), 5.42(q, J=6.0 Hz,1H), 7.03(t,J=7.2 Hz,1H), 7.19(d,J= 7.6 Hz,1H), 7.43(dt, J=2.0 Hz,7.2 Hz,1H), 7.73(dd,J=2.0 Hz,7.6 Hz,1H).

Example 37

6-Oxocyclodecyl (4-methoxy-2-methoxymethoxy)benzoate $^1$H-NMR δ(CDCl$_3$); 1.52–1.76(m,8H), 1.82–2.04(m,4H), 2.28–2.38 (m,2H), 2.83–2.91(m,2H), 3.52(s,3H), 3.83(s,3H), 5.24(s,2H), 5.37(q,J=6.0 Hz,1H), 6.55(dd,J=2.44 Hz,8.8 Hz,1H), 6.73(d,J=2.4 Hz, 1H), 7.79(d,J=8.8 Hz,1H).

Example 38

6-Oxocyclodecyl 2-nitrobenzoate $^1$H-NMR δ(CDCl$_3$); 1.54–1.76(m,8H), 1.83–2.10(m,4H), 2.32–2.40(m,2H), 2.83–2.91(m,2H), 5.42(q,J=6.0 Hz,1H), 7.60–7.78(m,3H), 7.87(d,J=7.6 Hz,1H).

Example 39

6-Oxocyclodecyl 4-methoxybenzoate $^1$H-NMR δ(CDCl$_3$); 1.52–1.76(m,8H), 1.82–2.04(m,4H), 2.33–2.41 (m,2H), 2.83–2.91(m,2H), 3.86(s,3H), 5.38(q,J= 6.0 Hz,2H), 7.42(d,J=7.6 Hz,2H), 7.97(d,J=7.6 Hz,2H).

Example 40

5-Oxo-3-cyclooctenyl (4-methoxy-2-methoxymethoxy)-benzoate

The compound obtained in Example 33 was treated in a manner similar to Example 12, to yield the titled compound.

$^1$H-NMR δ(CDCl$_3$); 1.72–2.10(m,4H), 2.82(t,J=6.8 Hz,2H), 2.90–3.03(m,2H), 3.52(s,3H), 3.84(s,3H), 4.85–4.94(m,1H), 5.24 (s,2H), 5.25–5.33(m,1H), 6.28(d,J= 12 Hz,1H), 6.47(dt,J=12 Hz, 8.4 Hz,1H), 6.56(dd,J=2.4 Hz,8.4 Hz,1H), 6.73(d,J=2.4 Hz,1H), 7.79(d,J=8.8 Hz,1H).

Example 41

5-Oxo-3-cyclooctenyl (2-methoxymethoxy)benzoate

The compound obtained in Example 34 was treated in a manner similar to Example 12, to yield the titled compound.

$^1$H-NMR δ(CDCl$_3$); 1.72–2.10(m,4H), 2.82(t,J=6.8 Hz,2H), 2.93–3.08(m,2H), 3.52(s,3H), 5.24(s,2H), 5.27–5.36(m,1H), 6.29(d, J=12 Hz,1H), 6.48(dt,J=12 Hz,8.4 Hz,1H), 7.05(dt,J=1.2,8.0 Hz,1H), 7.19(d,J=8.0 Hz,1H) 7.46 (dt,J=2.0,8.0 Hz,1H), 7.74(dd,J=2.0, 8.0 Hz,1H).

Example 42

6-oxo-4-cyclodecenyl benzoate

The compound obtained in Example 35 was treated in a manner similar to Example 12, to yield the titled compound.

$^1$H-NMR δ(CDCl$_3$); 1.44–1.95(m,6H), 2.06–2.40(m,4H), 2.62–2.71 (m,1H), 2.75–2.88(m,1H), 5.16–5.24(m,1H), 5.99(dt,J=4.8 Hz, 12 Hz,1H), 6.40(d,J=12 Hz,1H), 7.43(t, J=7.6 Hz,2H), 7.55(t, J=7.2 Hz,1H), 8.02(d,J=7.2 Hz,2H).

Example 43

Z-6-oxo-4-cyclodecenyl (2-methoxymethoxy)benzoate

The compound obtained in Example 36 was treated in a manner similar to Example 12, to yield the titled compound.

$^1$H-NMR δ(CDCl$_3$); 1.44–1.95(m,6H), 2.08–2.34(m,4H), 2.62–2.70 (m,1H), 2.74–2.86(m,1H), 3.51(s,3H), 5.16–5.23 (m,1H), 5.24(s, 2H), 5.99(dt,J=5.2 Hz,12 Hz,1H), 6.38(d,J= 12 Hz,1H), 7.03(t, J=7.6 Hz,1H), 7.19(d,J=8.0 Hz,1H), 7.42(dt,J=1.6 Hz,7.6 Hz,1H), 7.72(dd,J=1.6 Hz,7.6 Hz,1H).

Example 44

Z-6-oxo-4-cyclodecenyl (4-methoxy-2-methoxymethoxy)benzoate

The compound obtained in Example 37 was treated in a manner similar to Example 12, to yield the titled compound.

$^1$H-NMR δ(CDCl$_3$); 1.42–1.95(m,6H), 2.12–2.37(m,4H), 2.62–2.68(m,1H), 2.72–2.92(m,1H), 3.50(s,3H), 3.82(s,3H), 5.10–5.21 (m,1H), 5.23(s,2H), 5.97(dt,J=5.4 Hz,12 Hz,1H), 6.36(d,J=12 Hz, 1H), 6.54(br.d,J=8.0 Hz,1H), 6.72(br.s,1H), 7.77(br.d,J=7.2 Hz, 1H).

Example 45

Z-6-oxo-4-cyclodecenyl 2-nitrobenzoate

The compound obtained in Example 38 was treated in a manner similar to Example 12, to yield the titled compound.

¹H-NMR δ(CDCl₃); 1.42–1.90(m,4H), 1.92–2.00(m,2H), 2.05–2.37 (m,4H), 2.62–2.69(m,1H), 2.72–2.87(m,1H), 5.15–5.23(m,1H), 5.99(dt,J=5.2 Hz,12 Hz,1H), 6.40(br. d,J=12.0 Hz,1H), 7.60–7.72 (m,3H), 7.90(d,J=7.6 Hz,1H).

Example 46

Z-6-oxo-4-cyclodecenyl 4-methoxybenzoate

The compound obtained in Example 39 was treated in a manner similar to Example 12, to yield the titled compound.
¹H-NMR δ(CDCl₃); 1.42–1.92(m,6H), 2.07–2.34(m,4H), 2.62–2.68 (m,1H), 2.74–2.86(m,1H), 3.85(s,3H), 5.13–5.21 (m,1H), 5.98(dt, J=5.2 Hz,12 Hz,1H), 6.38(d,J=12 Hz,1H), 6.91(br. d,J=8.4 Hz,2H), 7.96(br. d,J=8.4 Hz,2H).

Example 47

5-Oxo-3-cyclooctenyl (2-hydroxy-4-methoxy)benzoate

The compound obtained in Example 40 was treated in a manner similar to Example 16, to yield the titled compound as colorless liquid.
¹H-NMR δ(CDCl₃); 1.68–2.10(m,4H), 2.78–2.84(m,2H), 2.90–3.06 (m,2H), 3.83(s,3H), 5.30–5.37(m,1H), 6.30(d,J=12 Hz,1H), 6.38–6.52(m,3H), 7.69(d,J=8.8 Hz,1H), 10.96 (s,1H).

Example 48

5-Oxo-3-cyclooctenyl 2-hydroxybenzoate

The compound obtained in Example 41 was treated in a manner similar to Example 16, to yield the titled compound as colorless liquid.
¹H-NMR δ(CDCl₃); 1.73–2.11(m,4H), 2.78–2.86(m,2H), 2.92–3.08 (m,2H), 5.33–5.40(m,1H), 6.31(d,J=12 Hz,1H), 6.43–6.51(m,1H), 6.89(dt,J=1.2 Hz,7.6 Hz,1H), 6.99(d,J=8.0 Hz,1H), 7.47(dt, J=1.6 Hz,7.6 Hz,1H), 7.80(dd,J=1.6 Hz,8.0 Hz,1H), 10.74(s,1H).

Example 49

Z-6-oxo-4-cyclodecenyl 2-hydroxybenzoate

The compound obtained in Example 43 was treated in a manner similar to Example 16, to yield the titled compound as colorless liquid.
¹H-NMR δ(CDCl₃); 1.46–1.92(m,6H), 2.02–2.28(m,4H), 2.65–2.75 (m,1H), 2.80–2.90(m,1H), 5.06–5.15(m,1H), 5.94(dt,J=5.2 Hz, 12 Hz,1H), 6.36(t,J=12 Hz,1H), 6.87(t,J=7.2 Hz,1H), 6.97(d, J=7.6 Hz,1H), 7.45(dt,J=2.0 Hz,7.2 Hz,1H), 7.78(d,J=8.4 Hz,2H), 10.78(s,1H).

Example 50

Z-6-oxo-4-cyclodecenyl (2-hydroxy-4-methoxy)benzoate

The compound obtained in Example 44 was treated in a manner similar to Example 16, to yield the titled compound as colorless liquid.
¹H-NMR δ(CDCl₃); 1.42–1.92(m,6H), 2.07–2.34(m,4H), 2.62–2.70 (m,1H), 2.72–2.86(m,1H), 3.82(s,3H), 5.13–5.23 (m,1H), 5.98(dt, J=5.2 Hz,12 Hz,1H), 6.38–6.45(m,3H), 6.87(t,J=8.4 Hz,1H), 6.95(d, J=8.4 Hz,1H), 7.44(t,J=8.4 Hz,1H), 7.80(d,J=8.4 Hz,2H), 11.78(s, 1H).

Example 51

(2RS,3RS)-2,3-dihydroxy-5-phenethyl-1-cyclooctanone 1.2 g of the product obtained in Example 5 was dissolved in 50 ml of tetrahydrofuran, and to the resulting solution was added a solution of 0.91 g of sodium chlorate in 50 ml of water and then 3 ml of 3% solution of osmium tetroxide in tert-butanol. The resulting solution was stirred under nitrogen atmosphere at room temperature overnight. The reaction solution was cooled in an ice bath, and to the solution was added 30 ml of dilute aqueous solution of sodium sulfite. The reaction solution was stirred for twenty minutes, and then extracted with ethyl acetate. The organic phase was washed with a saturated saline solution, and dried over anhydrous sodium sulfate. The solvent was evaporate under reduced pressure. The resulting crude product was purified by column chromatography on silica gel, and elution with ethyl acetate-hexane (1:3) was collected, to afford 0.19 g and 0.41 g of two forms (a) and (b) of diastereomer of the titled compound as colorless liquid, respectively.
(a) Less Polar Isomer 51
¹H-NMR δ(CDCl₃); 1.38–1.90(m,8H), 2.00–2.22(m,1H), 2.38–2.72 (m,4H), 3.61(t,J=4.4 Hz,1H), 4.02–4.14(m,1H), 4.20–4.38(m,1H), 4.55–4.59(m,1H), 7.11–7.20(m,3H), 7.27–7.31 (m,2H).
(b) More Polar Isomer 51
¹H-NMR δ(CDCl₃); 1.42–1.65 (m,5H), 1.70–2.06(m, 3H), 2.29(br.d, J=9.6 Hz,1H), 2.38–2.70(m,4H), 3.70–3.73 (m,1H), 4.37–4.40(m, 1H), 4.46–4.56(m,1H), 7.11–7.20(m, 3H), 7.26–7.32(m,2H).

Example 52

(2RS,3RS)-2,3-dihydroxy-5-[2-(2-methoxymethoxyphenyl)ethyl]-1-cyclooctanone

The compound obtained in Example 13 was treated in a manner similar to Example 51, to yield the titled compound as colorless liquid.
(a) Less Polar Isomer 52
¹H-NMR δ(CDCl₃); 1.38–1.90(m,8H), 2.00–2.22(m,1H), 2.38–2.72 (m,4H), 3.48(s,3H), 3.61(t,J=4.4 Hz,1H), 4.02–4.14(m,1H), 4.20–4.38(m,1H), 4.55–4.59(m,1H), 5.19 (s,2H), 6.92(dt,J=1.4 Hz, 7.2 Hz,1H), 7.04(dd,J=1.4 Hz,8.0 Hz,1H), 7.08–7.15(m,2H).
(b) More Polar Isomer 52
¹H-NMR δ(CDCl₃); 1.42–1.65(m,5H), 1.70–2.06(m,3H), 2.29(br.d, J=9.6 Hz,1H), 2.38–2.70(m,4H), 3.46(s,3H), 3.70–3.73(m,1H), 4.37–4.40(m,1H), 4.46–4.56(m,1H), 5.19 (s,2H), 6.92(dt,J=1.4 Hz, 7.2 Hz,1H), 7.04(dd,J=1.4 Hz,8.0 Hz,1H), 7.08–7.15(m,2H).

Example 53

(2RS,3RS)-2,3-dihydroxy-5-[2-(3-methoxymethoxyphenyl)ethyl]-1-cyclooctanone

The compound obtained in Example 14 was treated in a manner similar to Example 51, to yield the titled compound as colorless liquid.
¹H-NMR δ(CDCl₃); 1.42–1.65(m,5H), 1.70–2.06(m,3H), 2.38–2.63 (m,4H), 3.49(s,3H), 3.70–3.73(m,1H), 4.02–4.18 (m,1H), 4.40–4.56(m,1H), 5.17(s,2H), 6.72–6.84(m,3H), 7.10–7.23(m,2H).

Example 54

(2RS,3RS)-6-benzyl-2,3-dihydroxy-1-cyclodecanone

The compound obtained in Example 22 (a) was treated in a manner similar to Example 51, to yield the titled compound as colorless liquid.
¹H-NMR δ(CDCl₃); 1.08–1.18(m,2H), 1.22–1.44(m,2H), 1.46–1.83 (m,6H), 2.06–2.20(m,1H), 2.22–2.42(m,2H), 2.66–2.74(m,1H), 2.90–3.02(m,1H), 3.79–3.82(m,1H), 4.30–4.44(m,2H), 7.08–7.30 (m,5H).

Example 55

(2RS,3RS)-2,3-dihydroxy-6-phenyl-1-cyclodecanone

The compound obtained in Example 23 (a) was treated in a manner similar to Example 51, to yield the titled compound as colorless liquid.

$^1$H-NMR δ(CDCl$_3$); 1.32–1.92(m,8H), 2.14–2.30(m,2H), 2.44–2.54 (m,1H), 2.65–2.76(m,1H), 3.12–3.22(m,1H), 3.86(d, J=4.4 Hz,1H), 4.45(br.s,1H), 4.48–4.56(m,1H), 7.10–7.33(m,5H).

Example 56

(3RS,4RS)-3,4-dihydroxy-5-oxocyclooctyl (2-methoxy-methoxy)benzoate

The compound obtained in Example 34 was treated in a manner similar to Example 51, to yield the titled compound as colorless liquid.

$^1$H-NMR δ(CDCl$_3$); 1.42–1.80(m,2H), 1.82–2.32(m,4H), 2.44–2.78 (m,2H), 3.52(s,3H), 4.38–4.56(m,1H), 4.76–4.84 (m,1H), 5.05–5.22(m,1H), 5.24(s,2H), 7.02–7.10(m,1H), 7.15–7.24(m,1H), 7.42–7.48(m,1H), 7.75(dd,J=1.6 Hz,8.0 Hz,1H).

Example 57

(4RS,5RS)-4,5-dihydroxy-6-oxocyclodecyl benzoate

The compound obtained in Example 35 was treated in a manner similar to Example 51, to yield the titled compound as colorless liquid.

$^1$H-NMR δ(CDCl$_3$); 1.42–1.76(m,8H), 1.92–2.32(m,4H), 2.44–2.58 (m,1H), 3.02–3.18(m,1H), 4.42(br.s,1H), 4.50–4.60(m,1H), 5.30–5.40(m,1H), 7.44(br.t,J=8.0 Hz,2H), 7.56(t,J=8.0 Hz,1H), 8.02 (br.d,J=8.0 Hz,2H).

Example 58

(4RS,5RS)-4,5-dihydroxy-6-oxocyclodecyl (2-methoxy-methoxy)benzoate

The compound obtained in Example 36 was treated in a manner similar to Example 51, to yield the titled compound as colorless liquid.

$^1$H-NMR δ(CDCl$_3$); 1.38–1.88(m,8H), 1.92–2.32(m,3H), 2.44–2.58 (m,1H), 3.02–3.18(m,1H), 3.52(s,3H), 4.44(br.s, 1H), 4.50–4.60 (m,1H), 5.25(s,2H), 5.30–5.40(m,1H), 7.03 (t,J=7.6 Hz,1H), 7.20 (d,J=8.4 Hz,1H), 7.44(br.d,J=8.4 Hz,1H), 7.73(d,J=8.0 Hz,1H).

Example 59

(4RS,5RS)-4,5-dihydroxy-6-oxocyclodecyl (4-methoxy-2-methoxymethoxy)benzoate

The compound obtained in Example 37 was treated in a manner similar to Example 51, to yield the titled compound as colorless liquid.

$^1$H-NMR δ(CDCl$_3$); 1.40–1.88(m,8H), 1.92–2.32(m,3H), 2.40–2.54 (m,1H), 3.02–3.18(m,1H), 3.52(s,3H), 3.84(s, 3H), 4.44(br.s,1H), 4.52–4.60(m,1H), 5.25(s,2H), 5.26–5.40 (m,1H), 6.55(dd,J=2.4 Hz, 8.4 Hz,1H), 6.74(d,J=2.4 Hz,1H), 7.78(d,J=8.4 Hz,1H).

Example 60

(4RS,5RS)-4,5-dihydroxy-6-oxocyclodecyl 2-nitrobenzoate

The compound obtained in Example 38 was treated in a manner similar to Example 51, to yield the titled compound as colorless liquid.

$^1$H-NMR δ(CDCl$_3$); 1.40–2.04(m,10H), 2.40–2.54(m, 1H), 3.02–3.18 (m,1H), 3.41(s,3H), 3.43(s,3H), 4.30–4.44 (m,2H), 5.00–5.10(m, 1H), 7.58–7.72(m,3H), 7.96(d,J=8.0 Hz,1H).

Example 61

(4RS,5RS)-4,5-dihydroxy-6-oxocyclodecyl 4-methoxybenzoate

The compound obtained in Example 39 was treated in a manner similar to Example 51, to yield the titled compound as colorless liquid.

$^1$H-NMR δ(CDCl$_3$); 1.40–1.88(m,8H), 2.15–2.30(m,2H), 2.46–2.56 (m,1H), 2.46–2.54(m,1H), 3.02–3.14(m,1H), 3.82(d,J=3.6 Hz,1H), 3.86(s,3H), 4.42–4.45(br.s,1H), 4.52–4.60(m,2H), 5.23–5.34(m, 1H), 6.91(d,J=8.4 Hz,2H), 7.80(d,J=8.4 Hz,2H).

Example 62

(a) and (c) (2RS,3RS)-2,3-di(methoxymethoxy)-5-phenethyl-1-cyclooctanone, and (b) (2RS,3RS)-2-hydroxy-3-methoxymethoxy-5-phenethyl-1-cyclooctanone 0.19 g of the diastereomer (a) isolated in Example 51 was dissolved in 30 ml of dichloromethane, and to the resulting solution were added 0.20 ml of diisopropylamine and 0.70 ml of chloromethylmethylether. The resulting solution was stirred at 40° C. for one and a half hours. Adding of reagent and stirring were continued at 40° C. until TLC indicated that starting materials had been consumed. As a result, adding 0.70 ml of diisopropylethylamine and 2.4 ml of chloromethylmethylether and stirring for seven hours had been required. The reaction solution was poured into ice water and the organic phase was separated. The aqueous phase was extracted with dichloromethane. The organic phase was washed water and a saturated saline solution, and dried over anhydrous sodium sulfate. The solvent was evaporated under reduced pressure. The resulting crude product was purified by column chromatography on silica gel, and the eluate with ethyl acetate-hexane (1:6) was collected, to afford 0.17 g of the titled compound (a) and 10 mg of the titled compound (b) as colorless liquid.

0.32 g of the other diastereomer (b) was treated in a manner similar to the above method, to afford 0.32 g of diastereomer (c) of the titled compound as pale yellow liquid.

(a) Less Polar Isomer 62 (a)

$^1$H-NMR δ(CDCl$_3$); 1.38–1.90(m,8H), 2.00–2.30(m,2H), 2.50–2.74 (m,2H), 2.80–2.90(m,1H), 3.38(s,3H), 3.40(s, 3H), 3.70–3.78(m, 1H), 4.20–4.32(m,1H), 4.62–4.78(m, 4H), 7.11–7.20(m,3H), 7.27–7.31(m,2H).

(b)

$^1$H-NMR δ(CDCl$_3$); 1.38–1.82(m,9H), 2.00–2.12(m,1H), 2.38–2.66 (m,3H), 3.45(s,3H), 3.78–3.81(m,1H), 4.40–4.50 (m,2H), 4.75–4.82(m,2H), 7.11–7.20(m,3H), 7.27–7.31(m, 2H).

(c) More Polar Isomer 62 (c)

$^1$H-NMR δ(CDCl$_3$); 1.20–1.84(m,8H), 1.92–2.14(m,1H), 2.30–2.42 (m,1H), 2.44–2.68(m,3H), 3.41(s,3H), 3.43(s, 3H), 4.37–4.44(m, 1H), 4.48–4.58(m,1H), 4.62–4.82(m, 4H), 7.10–7.20(m,3H), 7.26–7.32(m,2H).

Example 63

(2RS,3RS)-2,3-di(methoxymethoxy)-5-[2-(2-methoxymethoxyphenyl)ethyl]-1-cyclooctanone The compound obtained in Example 52 was treated in a manner similar to Example 62, to yield the titled compound as colorless liquid.

Less Polar Isomer 63 (a)
$^1$H-NMR δ(CDCl$_3$); 1.34–1.76(m,7H), 2.00–2.10(m,1H), 2.20–2.30 (m,1H), 2.50–2.74(m,3H), 2.83–2.92(m,1H), 3.40(s,3H), 3.41(s, 3H), 3.47(s,3H), 3.75–3.83(m,1H), 4.32–4.34(m,1H), 4.67(d, J=6.4 Hz,1H), 4.70–4.78(m,2H), 5.14–5.20(m,2H), 6.92(d,J=7.6 Hz, 1H), 7.04(d,J=1.4 Hz,8.0 Hz,1H), 7.07–7.16(m,2H).
More Polar Isomer 63 (b)
$^1$H-NMR δ(CDCl$_3$); 1.40–1.84(m,7H), 1.92–2.14(m,2H), 2.30–2.40 (m,1H), 2.48–2.68(m,3H), 3.43(s,3H), 3.44(s, 3H), 3.47(s,3H), 4.43–4.46(m,1H), 4.53–4.58(m,1H), 4.71 (d,J=7.2 Hz, 1H), 4.75–4.84(m,3H), 5.18(s,2H), 6.91(d,J=7.2 Hz,1H), 7.04(d,J=8.0 Hz, 1H), 7.06–6.16(m,2H).

Example 64

(2RS,3RS)-2,3-di(methoxymethoxy)-5-[2-(3-methoxymethoxyphenyl)ethyl]-1-cyclooctanone The compound obtained in Example 53 was treated in a manner similar to Example 62, to yield the titled compound as colorless liquid.
$^1$H-NMR δ(CDCl$_3$); 1.42–1.65(m,6H), 1.70–2.06(m,3H), 2.38–2.68 (m,4H), 3.49(s,3H), 4.02–4.15(m,1H), 4.37–4.40 (m,1H), 4.47–4.56(m,2H), 5.17(s,2H), 6.72–6.84(m,3H), 7.10–7.23(m,2H).

Example 65

(2RS,3RS)-6-benzyl-2,3-di(methoxymethoxy)-1-cyclodecanone

The compound obtained in Example 54 was treated in a manner similar to Example 62, to yield the titled compound as colorless liquid.
$^1$H-NMR δ(CDCl$_3$); 1.08–1.18(m,2H), 1.22–1.44(m,2H), 1.46–1.83 (m,6H), 2.06–2.20(m,1H), 2.22–2.42(m,2H), 2.66–2.74(m,1H), 2.90–3.02(m,1H), 3.42(s,3H), 3.45(s,3H), 4.32–4.40(m,1H), 4.50–4.84(m,5H), 7.08–7.30(m,5H).

Example 66

(2RS,3RS)-2,3-di(methoxymethoxy)-6-phenyl-1-cyclodecanone

The compound obtained in Example 55 was treated in a manner similar to Example 62, to yield the titled compound as colorless liquid.
$^1$H-NMR δ(CDCl$_3$); 1.12–1.88(m,8H), 1.92–2.04(m,1H), 2.26–2.40 (m,2H), 2.50–2.60(m,1H), 3.02–3.12(m,1H), 3.34(s,3H), 3.43(s, 3H), 4.04–4.11(m,1H), 4.35(br.s,1H), 4.58(d,J=6.4 Hz,1H), 4.66–4.76(m,2H), 4.83(d,J=6.4 Hz,1H), 7.08–7.31(m,5H).

Example 67

(3RS,4RS)-3,4-di(methoxymethoxy)-5-oxocyclooctyl (2-methoxymethoxy)benzoate

The compound obtained in Example 56 was treated in a manner similar to Example 62, to yield the titled compound as colorless liquid.
Less Polar Isomer 67 (a)
$^1$H-NMR δ(CDCl$_3$); 1.76–2.16(m,4H), 2.20–2.36(m,1H), 2.44–2.63 (m,2H), 2.98–3.06(m,1H), 3.39(s,3H), 3.42(s, 3H), 3.51(s,3H), 4.08–4.15(m,1H), 4.35(br.s,1H), 4.62–4.82 (m,4H), 4.86–4.95(m, 1H), 5.20–5.28(m,2H), 7.03(t,J=8.0 Hz,1H), 7.18(d,J=8.0 Hz,1H), 7.43(t,J=7.4 Hz,1H), 7.72(d, J=7.6 Hz,1H).
More Polar Isomer 67 (b)
$^1$H-NMR δ(CDCl$_3$); 1.70–2.02(m,4H), 2.05–2.14(m,1H), 2.36–2.45 (m,1H), 2.54–2.63(m,1H), 2.82–2.90(m,1H), 3.34(s,3H), 3.41(s, 3H), 3.51(s,3H), 4.28–4.40(m,1H), 4.64–4.80(m,4H), 5.05–5.16(m, 1H), 5.25(s,2H), 7.04(t,J=8.0 Hz,1H), 7.20(d,J=8.0 Hz,1H), 7.44 (t,J=6.8 Hz,1H), 7.76(d,J=7.6 Hz,1H).

Example 68

(4RS,5RS)-4,5-di(methoxymethoxy)-6-oxocyclodecyl benzoate

The compound obtained in Example 57 was treated in a manner similar to Example 62, to yield the titled compound as colorless liquid.
$^1$H-NMR δ(CDCl$_3$); 1.42–1.76(m,8H), 1.92–2.32(m,4H), 2.44–2.62 (m,1H), 3.02–3.12(m,1H), 3.38(s,3H), 3.45(s, 3H), 4.30–4.36(m, 1H), 4.43(br.s,1H), 4.68(d,J=6.8 Hz,1H), 4.72(d,J=6.8 Hz,1H), 4.76(d,J=6.8 Hz,1H), 4.86(d,J=6.8 Hz,1H), 5.02–5.10(m,1H), 7.42(br.t,J=8.0 Hz,2H), 7.55(t,J=8.0 Hz,1H), 8.01(br.d,J=8.0 Hz,2H).

Example 69

(1RS,4RS)-4,5-di(methoxymethoxy)-6-oxocyclodecyl (2-methoxymethoxy)benzoate

The compound obtained in Example 58 was treated in a manner similar to Example 62, to yield the titled compound as colorless liquid.
$^1$H-NMR δ(CDCl$_3$); 1.38–1.88(m,8H), 1.92–2.32(m,3H), 2.44–2.58 (m,1H), 3.02–3.14(m,1H), 3.39(s,3H), 3.44(s, 3H), 3.51(s,3H), 4.34–4.40(m,1H), 4.43(br.s,1H), 4.69(d,J=6.8 Hz,1H), 4.73(d, J=6.8 Hz,1H), 4.75(d,J=6.8 Hz,1H), 4.86(d,J=6.8 Hz,1H), 5.04–5.12(m,1H), 5.23(s,2H), 7.03(t, J=8.0 Hz,1H), 7.19(d,J=8.0 Hz, 1H), 7.42(dt,J=1.6 Hz,7.8 Hz,1H), 7.71(dd,J=1.6 Hz,7.8 Hz,1H).

Example 70

(4RS,5RS)-4,5-di(methoxymethoxy)-6-oxocyclodecyl (4-methoxy-2-methoxymethoxy)benzoate The compound obtained in Example 59 was treated in a manner similar to Example 62, to yield the titled compound as colorless liquid.
$^1$H-NMR δ(CDCl$_3$); 1.40–1.82(m,8H), 1.82–2.20(m,3H), 2.40–2.54 (m,1H), 3.02–3.18(m,1H), 3.39(s,3H), 3.44(s, 3H), 3.51(s,3H), 3.83(s,3H), 4.30–4.38(m,1H), 4.42(br.s, 1H), 4.69(d,J=6.8 Hz, 1H), 4.73(d,J=6.8 Hz,1H), 4.75(d,J=6.8 Hz,1H), 4.85(d,J=6.4 Hz, 1H), 4.98–5.06(m,1H), 5.23 (s,2H), 6.55(dd,J=2.0 Hz,8.4 Hz,1H), 6.71(d,J=2.0 Hz,1H), 7.77(d,J=8.4 Hz,1H).

Example 71

(4RS,5RS)-4,5-di(methoxymethoxy)-6-oxocyclodecyl 2-nitrobenzoate

The compound obtained in Example 60 was treated in a manner similar to Example 62, to yield the titled compound as colorless liquid.
$^1$H-NMR δ(CDCl$_3$); 1.40–2.04(m,10H), 2.40–2.54(m, 1H), 3.02–3.18 (m,1H), 3.42(s,3H), 3.44(s,3H), 4.32–4.41 (m,1H), 4.42(br.s,1H), 4.70–4.80(m,3H), 4.86(d,J=6.4 Hz,1H), 5.00–5.10(m,1H), 7.58–7.72(m,3H), 7.89(d,J=8.0 Hz,1H).

Example 72

(4RS,5RS)-4,5-di(methoxymethoxy)-6-oxocyclodecyl 4-methoxybenzoate

The compound obtained in Example 61 was treated in a manner similar to Example 62, to yield the titled compound as colorless liquid.

¹H-NMR δ(CDCl₃); 1.40–1.88(m,8H), 2.15–2.30(m,2H), 2.46–2.56 (m,1H), 2.46–2.54(m,1H), 3.02–3.14(m,1H), 3.38(s,3H), 3.44(s, 3H), 3.82(d,J=3.6 Hz,1H), 3.85(s,3H), 4.32–4.37(m,1H), 4.42 (br.s,1H), 4.68(d,J=7.0 Hz,1H), 4.72 (d,J=7.0 Hz,1H), 4.76(d, J=6.4 Hz,1H), 4.86(d,J=6.4 Hz,1H), 4.98–5.08(m,1H), 7.40(d, J=8.4 Hz,2H), 7.96(d,J=8.4 Hz,2H).

Example 73

(7RS,8RS)-7,8-di(methoxymethoxy)-5-phenethyl-2-cycloocten-1-one

The compounds obtained in Examples 62 (a) and (c) were treated in a manner similar to Example 12, to yield less polar isomer 73 (a) and more polar isomer 73 (b), respectively, as colorless liquid.
(a) Less Polar Isomer 73
¹H-NMR δ(CDCl₃); 1.48–2.12(m,5H), 2.46–2.75(m,3H), 3.02–3.12 (m,1H), 3.35(s), 3.37(s), 3.38(s), 3.39(s,total 6H), 3.85–4.00 (m,1H), 4.56–4.90(m,5H), 6.31(d,J=12 Hz,1H), 6.45(dt,J=12 Hz, 8.0 Hz,1H), 7.12–7.22(m,3H), 7.26–7.32 (m,2H).
(b) More Polar Isomer 73
¹H-NMR δ(CDCl₃); 1.40–1.90(m,4H), 2.00–2.30(m,2H), 2.48–2.72 (m,3H), 3.39(s,3H), 3.44(s,3H), 4.30–4.40(br.m, 1H), 4.64–4.83 (br.m,5H), 6.04–6.13(br.m,1H), 6.32–6.42 (br.m,1H), 7.12–7.22 (m,3H), 7.26–7.32(m,2H).

Example 74

(7RS,8RS)-7,8-di(methoxymethoxy)-5-[2-(2-methoxymethoxyphenyl)ethyl]-2-cycloocten-1-one The compounds obtained in Examples 63 (a) and 63 (b) were treated in a manner similar to Example 73, to yield 74 (a) and 74 (b), respectively, as colorless liquid.
(a) Less Polar Isomer 74
¹H-NMR δ(CDCl₃); 1.46–1.74(m,3H), 1.85–2.30(m,2H), 2.50–2.78 (m,4H), 3.39(s,6H), 3.49(s,3H), 3.97–4.03(m,1H), 4.61(d, J=7.2 Hz,1H), 4.67–4.64(m,2H), 4.86(d,J=7.2 Hz,1H), 4.91(d, J=3.6 Hz,1H), 5.21(s,2H), 6.32(d,J=12 Hz,1H), 6.47(dt,J=8.4 Hz, 12 Hz,1H), 6.94(dt,J=1.6 Hz,7.2 Hz,1H), 7.07(d,J=8.4 Hz,1H), 7.10–7.20(m,2H).
(b) More Polar Isomer 74
¹H-NMR δ(CDCl₃); 1.46–1.80(m,3H), 1.94–2.30(m,3H), 2.50–2.78 (m,3H), 3.39(s,3H), 3.43(s,3H), 3.49(s,3H), 4.28–4.30(m,1H), 4.60–4.82(m,5H), 5.16–5.22(m,2H), 6.04–6.14(m,1H), 6.32–6.44 (m,1H), 6.93(dt,J=1.6 Hz,7.2 Hz,1H), 7.06(d,J=8.4 Hz,1H), 7.10–7.20(m,2H).

Example 75

(7RS,8RS)-7,8-di(methoxymethoxy)-5-[2-(3-methoxymethoxyphenyl)ethyl]-2-cycloocten-1-one The compounds obtained in Examples 64 (a) and 64 (b) were treated in a manner similar to Example 73, to yield the titled compounds 75(a) and 75 (b), respectively, as colorless liquid.
(a) Less Polar Isomer 75
¹H-NMR δ(CDCl₃); 1.46–1.78(m,3H), 1.84–2.04(m,2H), 2.44–2.78 (m,4H), 3.38(s,3H), 3.39(s,3H), 3.49(s,3H), 3.94–4.00(m,1H), 4.60(d,J=7.0 Hz,1H), 4.70(t,J=7.0 Hz,2H), 4.86(d,J=7.0 Hz,1H), 4.89(br.d,J=3.6 Hz,1H), 5.18 (s,2H), 6.31(d,J=12 Hz,1H), 6.46(dt,J=8.4 Hz,12 Hz,1H), 6.78–6.94(m,3H), 7.21(t,J=8.0 Hz,1H).
(b) More Polar Isomer 75
¹H-NMR δ(CDCl₃); 1.46–1.82(m,3H), 1.92–2.30(m,2H), 2.44–2.70 (m,4H), 3.39(3H), 3.44(s,3H), 3.49(s,3H), 4.30–4.42(m,1H), 4.80–4.90(m,5H), 5.18(s,2H), 6.06–6.15 (m,1H), 6.31–6.41(m,1H), 6.78–6.91(m,3H), 7.21(t,J=8.0 Hz, 1H).

Example 76

Z-(9RS,10RS)-6-benzyl-9,10-di(methoxymethoxy)-2-cyclodecen-1-one

The compound obtained in Example 65 was treated in a manner similar to Example 73, to yield the titled compound as colorless liquid.
¹H-NMR δ(CDCl₃); 1.02–1.63(m,6H), 1.98–2.10(m,2H), 2.28–2.36 (m,1H), 2.70–2.90(m,2H), 3.42(s,3H), 3.44(s, 3H), 4.32–4.40(m, 1H), 4.50–4.58(m,2H), 4.69(d,J=7.2 Hz,1H), 4.78(d,J=6.8 Hz,1H), 4.83(d,J=6.8 Hz,1H), 5.80(dt, J=5.2 Hz,12 Hz,1H), 6.33(d,J=12 Hz, 1H), 7.08–7.30(m, 5H).

Example 77

Z-(9RS,10RS)-9,10-di(methoxymethoxy)-6-phenyl-2-cyclodecen-1-one

The compound obtained in Example 66 was treated in a manner similar to Example 73, to yield the titled compound as colorless liquid.
¹H-NMR δ(CDCl₃); 1.24–1.80(m,5H), 1.92–2.04(m,1H), 2.18–2.28 (m,1H), 2.40–2.50(m,1H), 2.98–3.06(m,1H), 3.42(s,3H), 3.45(s, 3H), 4.53–4.60(m,2H), 4.64(d,J=7.2 Hz,1H), 4.76(d,J=7.2 Hz,1H), 4.83(q,J=6.8 Hz,2H), 6.02(dt, J=5.2 Hz,12 Hz,1H), 6.48(d,J=12 Hz, 1H), 7.14–7.23(m, 3H), 7.27–7.31(m,2H).

Example 78

Z-(6RS,7RS)-6,7-di(methoxymethoxy)-5-oxo-3-cyclooctenyl (2-methoxymethoxy)benzoate The compound obtained in Example 67 was treated in a manner similar to Example 73, to yield the titled compound as colorless liquid.
Less Polar Isomer 78 (a)
¹H-NMR δ(CDCl₃); 2.10–2.38(m,2H), 2.84–3.00(m,2H), 3.38(s, 3H), 3.41(s,3H), 3.52(s,3H), 4.10–4.20(m,2H), 4.60–4.78(m, 5H), 5.25(s,2H), 5.36–5.48(m,1H), 6.38–6.54 (m,2H), 7.05(dt,J=1.2, 8.0 Hz,1H), 7.19(d,J=8.0 Hz,1H), 7.46(dt,J=8.0 Hz,1H), 7.73(d, J=8.0 Hz,1H).
More Polar Isomer 78 (b)
¹H-NMR δ(CDCl₃); 2.19–2.40(m,2H), 2.72–2.83(m,1H), 2.99–3.12 (m,1H), 3.36(s,3H), 3.39(s,3H), 3.52(s,3H), 4.30–4.40(m,1H), 4.62–5.00(m,5H), 5.24–5.30(m,2H), 5.32–5.44(m,1H), 6.31(d, J=12 Hz,1H), 6.42–6.52(m,1H), 7.06(t,J=7.6 Hz,1H), 7.20–7.25(m, 1H), 7.48(t,J=7.2 Hz,1H), 7.78(d,J=7.2 Hz,1H).

Example 79

Z-(7RS,8RS)-7,8-di(methoxymethoxy)-6-oxo-4-cyclodecenyl benzoate

The compound obtained in Example 68 was treated in a manner similar to Example 73, to yield the titled compound as colorless liquid.
¹H-NMR δ(CDCl₃); 1.52–1.70(m,4H), 1.82–1.94(m,1H), 2.02–2.10 (m,1H), 2.20–2.28(m,1H), 2.80–2.93(m,1H), 3.43(s,3H), 3.46(s, 3H), 4.46–4.53(m,1H), 4.62(br.s,1H), 4.72(d,J=8.0 Hz,1H), 4.78 (d,J=8.0 Hz,1H), 4.81(d,J=6.4 Hz,1H), 4.85(d,J=6.4 Hz,1H), 5.06–5.15(m,1H), 6.10(dt,J= 12 Hz,5.6 Hz,1H), 6.49(d,J=12 Hz,1H), 7.44 (br.t,J=7.6 Hz,2H), 7.56(t,J=8.4 Hz,1H), 8.02(d,J=8.4 Hz,2H).

Example 80

Z-(7RS,8RS)-7,8-di(methoxymethoxy)-6-oxo-4-cyclodecenyl (2-methoxymethoxy)benzoate The compound obtained in Example 69 was treated in a manner similar to Example 73, to yield the titled compound as colorless liquid.

Example 81

Z-(7RS,8RS)-7,8-di(methoxymethoxy)-6-oxo-4-cyclodecenyl (4-methoxy 2-methoxymethoxy) benzoate The compound obtained in Example 70 was treated in a manner similar to Example 73, to yield the titled compound as colorless liquid.

$^1$H-NMR δ(CDCl$_3$); 1.40–1.76(m,2H), 1.82–2.10(m,2H), 2.22–2.30 (m,1H), 2.77–2.92(m,1H), 3.42(s,3H), 3.46(s,3H), 3.50(s,3H), 3.83(s,3H), 4.44–4.51(m,1H), 4.62(br.s,1H), 4.71(d,J=6.8 Hz, 1H), 4.76(d,J=6.8 Hz,1H), 4.80(d,J=6.8 Hz,1H), 4.86(d,J=6.8 Hz, 1H), 5.01–5.10(m,1H), 5.22 (s,2H), 6.10(dt,J=12 Hz,5.2 Hz,1H), 6.47(d,J=12 Hz,1H), 6.55(dd,J=2.4 Hz,8.8 Hz,1H), 6.71(d,J=2.4 Hz, 1H), 7.76(d, J=8.8 Hz,1H).

Example 82

Z-(7RS,8RS)-7,8-di(methoxymethoxy)-6-oxo-4-cyclodecenyl 2-nitrobenzoate

The compound obtained in Example 71 was treated in a manner similar to Example 73, to yield the titled compound as colorless liquid.

$^1$H-NMR δ(CDCl$_3$); 1.44–1.81(m,4H), 1.87–2.12(m,2H), 2.20–2.30 (m,1H), 2.77–2.90(m,1H), 3.46(s,6H), 4.46–4.51 (m,1H), 4.62 (br.s,1H), 4.75(d,J=6.8 Hz,1H), 4.77–4.82(m, 2H), 4.85(d,J=6.8 Hz,1H), 5.06–5.14(m,1H), 6.10(dt,J=12 Hz,5.6 Hz,1H), 6.49 (d,J=12 Hz,1H), 7.60–7.70(m,3H), 7.93(d,J=8.0 Hz,1H).

Example 83

Z-(7RS,8RS)-7,8-di(methoxymethoxy)-6-oxo-4-cyclodecenyl 4-methoxybenzoate

The compound obtained in Example 72 was treated in a manner similar to Example 73, to yield the titled compound as colorless liquid.

$^1$H-NMR δ(CDCl$_3$); 1.44–1.83(m,4H), 1.93–2.10(m,2H), 2.17–2.28 (m,1H), 2.77–2.90(m,1H), 3.41(s,6H), 3.46(s,6H), 3.85(s,3H), 4.46–4.51(m,1H), 4.61(br.s,1H), 4.70(d,J=6.8 Hz,1H), 4.76(d, J=6.8 Hz,1H), 4.79(d,J=6.8 Hz,1H), 4.85(d,J=6.8 Hz,1H), 5.01–5.10(m,1H), 6.09(dt,J=12 Hz,5.2 Hz,1H), 6.47(d,J=12 Hz,1H), 6.90(d,J=7.6 Hz,2H), 7.96(d, J=7.6 Hz,2H).

Example 84

(7RS,8RS)-7,8-dihydroxy-5-phenethyl-2-cycloocten-1-one

The compounds obtained in Examples 73 (a) and 73 (b) were treated in a manner similar to Example 16, to yield the following compounds 84 (a) and 84 (b), respectively, as colorless liquid.

(a) Less Polar Isomer 84

$^1$H-NMR δ(CDCl$_3$); 1.45–2.14(m,6H), 2.48–2.75(m,3H), 3.98–4.04 (m,1H), 4.38(d,J=4.8 Hz,1H), 4.77(t,J=4.8 Hz,1H), 6.48(d,J=12 Hz, 1H), 6.62(dt,J=12 Hz,8.0 Hz,1H), 7.12–7.22(m,3H), 7.26–7.32(m, 2H).

(b) More Polar Isomer 84

$^1$H-NMR δ(CDCl$_3$); 1.50–1.90(m,3H), 2.03–2.32(m,2H), 2.54–2.88 (m,4H), 4.15–4.24(br.m,1H), 4.37(br.d,J=4.0 Hz,1H), 4.68–4.73 (br.m,1H), 6.40(d,J=12 Hz,1H), 6.64(dt, J=12 Hz,8.4 Hz,1H), 7.12–7.24(m,3H), 7.26–7.36(m,2H).

Example 85

(7RS,8RS)-7,8-dihydroxy-5-[2-(2-hydroxyphenyl) ethyl]-2-cycloocten-1-one

The compounds obtained in Examples 74 (a) and 74 (b) were treated in a manner similar to Example 16, to yield the following compounds 85 (a) and 85 (b), respectively.

(a) Less Polar Isomer 85

$^1$H-NMR δ(CDCl$_3$); 1.46–1.78(m,3H), 1.90–2.30(m,2H), 2.54–2.78 (m,4H), 4.18–4.38(m,1H), 4.69–4.88(m,2H), 6.41 (dd,J=2.0 Hz, 12 Hz,1H), 6.66(dt,J=12 Hz,7.6 Hz,1H), 6.74(d,J=8.0 Hz,1H), 6.88 (d,J=7.2 Hz,1H), 6.98(s,1H), 7.05–7.14(m,2H).

(b) More Polar Isomer 85

$^1$H-NMR δ(CDCl$_3$); 1.46–1.80(m,3H), 1.94–2.30(m,3H), 2.50–2.78 (m,3H), 3.96–4.20(m,1H), 4.64–4.84(m,1H), 5.02–5.18(m,1H), 6.41(dd,J=2.0 Hz,12 Hz,1H), 6.66(dt,J=12 Hz,8.0 Hz,1H), 6.73(d, J=8.0 Hz,1H), 6.87(t,J=7.6 Hz,1H), 7.05–7.15(m,2H).

Example 86

(7RS,8RS)-7,8-dihydroxy-5-[2-(3-hydroxyphenyl) ethyl]-2-cycloocten-1-one

The compounds obtained in Examples 75 (a) and 75 (b) were treated in a manner similar to Example 16, to yield the following compounds 86 (a) and 86 (b), respectively.

(a) Less Polar Isomer 86

$^1$H-NMR δ(CDCl$_3$); 1.46–1.73(m,3H), 1.84–2.04(m,2H), 2.44–2.78 (m,3H), 3.37–3.44(m,1H), 3.94–4.10(m,1H), 4.74–4.84(m,2H), 5.18(s,2H), 6.40–6.49(m,1H), 6.54–6.70 (m,3H), 7.13(t,J=8.0 Hz, 1H).

(b) More Polar Isomer 86

$^1$H-NMR δ(CDCl$_3$); 1.46–1.86(m,3H), 1.92–2.33(m,2H), 2.44–2.70 (m,2H), 2.78–3.02(m,1H), 3.39–3.52(m,1H), 4.10–4.24(m,1H), 4.70–4.86(m,2H), 6.30–6.38(m,1H), 6.58–6.72(m,3H), 7.08–7.17(m,2H).

Example 87

Z-(9RS,10RS)-6-benzyl-9,10-dihydroxy-2-cyclodecen-1-one

The compound obtained in Example 76 was treated in a manner similar to Example 16, to yield the titled compound.

$^1$H-NMR δ(CDCl$_3$); 1.02–1.63(m,6H), 1.84–1.98(m,1H), 2.02–2.30 (m,2H), 2.77–2.90(m,2H), 3.72(br.d,J=4.0 Hz,1H), 4.24–4.33(m, 1H), 4.49–4.54(m,1H), 5.86(dt,J=5.2 Hz,12 Hz,1H), 6.37(d, J=12 Hz, 1H), 7.10(d,J=7.2 Hz,2H), 7.17–7.30(m,3H).

Example 88

Z-(9RS,10RS)-9,10-dihydroxy-6-phenyl-2-cyclodecen-1-one

The compound obtained in Example 77 was treated in a manner similar to Example 16, to yield the titled compound.

$^1$H-NMR δ(CDCl$_3$); 1.24–1.50(m,3H), 1.58–1.82(m,3H), 2.08–2.15 (m,2H), 2.20–2.29(m,1H), 2.37–2.45(m,1H), 2.92–3.05(m,1H), 3.75(d,J=4.0 Hz,1H), 4.38–4.47(m,1H), 4.53–4.59(m,1H), 6.08(dt, J=5.2 Hz,12 Hz,1H), 6.52(d,J=12 Hz,1H), 7.14(d,J=7.2 Hz,2H), 7.17–7.31(m,3H).

Example 89

Z-(9RS,10RS)-10-hydroxy-9-methoxymethoxy-6-phenyl-2-cyclodecen-1-one

The compound obtained in Example 77 was treated in a manner similar to Example 16, to yield the titled compound.

¹H-NMR δ(CDCl₃); 1.24–1.80(m,5H), 1.85–1.97(m,1H), 2.20–2.28 (m,1H), 2.38–2.48(m,1H), 2.94–3.02(m,1H), 3.43(s,3H), 3.78(d, J=3.2 Hz,3H), 4.42–4.47(m,1H) 4.57–4.60(m,1H), 4.70(d,J=7.2 Hz, 1H), 4.76(d,J=7.2 Hz,1H), 6.08(dt,J=5.2 Hz,12 Hz,1H), 6.53 (d, J=12 Hz,1H), 7.15(d,J=7.2 Hz,2H), 7.17–7.31(m,3H).

Example 90

(6RS,7RS)-6,7-dihydroxy-5-oxo-3-cyclooctenyl 2-hydroxybenzoate

The compounds obtained in Examples 78 (a) and 78 (b) were treated in a manner similar to Example 16, to yield the following compounds 90 (a) and 90 (b), respectively.

Less Polar Isomer 90 (a)

¹H-NMR δ(CDCl₃); 2.03–2.16(m,1H), 2.44–2.52(m,1H), 2.84–3.06 (m,2H), 4.14–4.22(m,1H), 4.68(d,J=4.4 Hz,1H), 5.51–5.59(m,1H), 6.62–6.74(m,2H), 6.89(t,J=8.0 Hz,1H), 7.00(d,J=8.0 Hz,1H), 7.49 (t,J=7.2 Hz,1H), 7.75(dd,J=1.6 Hz,8.0 Hz,1H), 10.64(s,1H).

More Polar Isomer 90 (b)

¹H-NMR δ(CDCl₃); 2.03–2.12(m,1H), 2.46–2.56(m,1H), 2.70–2.80 (m,1H), 2.90–3.12(m,1H), 3.07–3.17(m,1H), 4.38–4.46(m,2H), 4.98(d,J=4.0 Hz,1H), 5.44–5.52(m,1H), 6.53(dd,J=1.6 Hz,12 Hz, 1H), 6.71(dt,J=12 Hz,8.0 Hz,1H), 6.92(t,J=8.0 Hz,1H), 7.01(d, J=8.0 Hz,1H), 7.50(t,J=7.2 Hz,1H), 7.82(dd,J=1.6 Hz,8.0 Hz,1H), 10.63(s,1H).

Example 91

Z-(7RS,8RS)-7,8-dihydroxy-6-oxo-4-cyclodecenyl benzoate

The compound obtained in Example 79 was treated in a manner similar to Example 16, to yield the titled compound.

¹H-NMR δ(CDCl₃); 1.42–1.76(m,4H), 1.82–1.97(m, 1H), 2.02–2.10 (m,1H), 2.20–2.30(m,1H), 2.78–2.93(m, 1H), 4.37–4.44(m,1H), 4.56(br.s,1H), 4.98–5.07(m,1H), 6.21(dt,J=12 Hz,5.2 Hz,1H), 6.50(d,J=12 Hz,1H), 7.44(br.t, J=7.6 Hz,2H), 7.56(t,J=8.0 Hz,1H), 8.01(d,J=8.0 Hz,2H).

Example 92

Z-(7RS,8RS)-7,8-dihydroxy-6-oxo-4-cyclodecenyl (2-hydroxy)benzoate

The compound obtained in Example 80 was treated in a manner similar to Example 16, to yield the titled compound.

¹H-NMR δ(CDCl₃); 1.44–1.77(m,4H), 1.84–2.00(m,2H), 2.24–2.34 (m,1H), 2.78–2.93(m,1H), 3.68–3.74(m,1H), 4.44–4.53(m,1H), 4.58(br.s,1H), 5.04–5.11(m,1H), 6.20(dt, J=12 Hz,5.2 Hz,1H), 6.53(d,J=12 Hz,1H), 6.87(t,J=8.0 Hz,2H), 6.96(d,J=8.4 Hz,1H), 7.46(dt,J=1.6 Hz,8.0 Hz,1H), 7.80(dd,J=1.6 Hz,8.0 Hz,2H), 10.76(s, 1H).

Example 93

Z-(7RS,8RS)-7,8-dihydroxy-6-oxo-4-cyclodecenyl (2-hydroxy-4-methoxy)benzoate The compound obtained in Example 81 was treated in a manner similar to Example 16, to yield the titled compound.

¹H-NMR δ(CDCl₃); 1.30–1.96(m,4H), 2.22–2.30(m,1H), 2:77–2.92(m,1H), 3.83(s,3H), 4.36–4.43(m,1H), 4.53–4.57 (m,1H), 4.98–5.07(m,1H), 6.19(dt,J=12 Hz,5.6 Hz,1H), 6.38–6.46(m,2H), 6.52(d,J=12 Hz,1H), 7.69(d,J=8.8 Hz,1H), 10.98(s,1H).

Example 94

Z-(7RS,8RS)-7,8-dihydroxy-6-oxo-4-cyclodecenyl 2-nitrobenzoate

The compound obtained in Example 82 was treated in a manner similar to Example 16, to yield the titled compound.

¹H-NMR δ(CDCl₃); 1.27–1.60(m,4H), 1.64–2.06(m,2H), 2.24–2.32 (m,1H), 2.76–2.90(m,1H), 3.65–3.78(m,1H), 4.39–4.45(m,1H), 4.57(br.s,1H), 4.98–5.08(m,1H), 6.21(dt, J=12 Hz,5.6 Hz,1H), 6.51(d,J=12 Hz,1H), 7.60–7.74(m,3H), 7.91(d,J=8.0 Hz,1H).

Example 95

Z-(7RS,8RS)-7,8-dihydroxy-6-oxo-4-cyclodecenyl 4-methoxybenzoate

The compound obtained in Example 83 was treated in a manner similar to Example 16, to yield the titled compound.

¹H-NMR δ(CDCl₃); 1.32–1.72(m,2H), 1.78–1.96(m,2H), 2.00–2.30 (m,2H), 2.77–2.86(m,1H), 3.72(d,J=4.0 Hz,1H), 3.86(s,3H), 4.36–4.46(m,1H), 4.53–4.57(m,1H), 4.95–5.05 (m,1H), 6.19(dt,J=12 Hz, 5.6 Hz,1H), 6.49(d,J=12 Hz,1H), 6.91(d,J=8.0 Hz,2H), 7.95(d, J=8.0 Hz,2H).

The compounds obtained in Examples were shown in Table 1. Furthermore, abbreviations of substituents shown in Table 1 represent the following groups:

Ph: phenyl group, Bz: benzyl group, 2-Pyr: 2-pyridyl group, MeO: methoxy group, MOMO: methoxymethoxy group, and OBzM: 4-methoxybenzyloxy group.

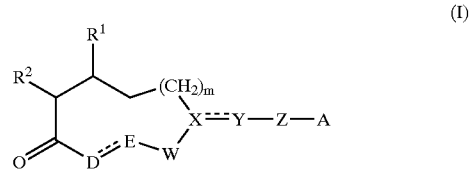

(I)

TABLE 1

| Example No. | m | D=E | W | X=Y | Z | A | Substituent of A | R¹ | R² |
|---|---|---|---|---|---|---|---|---|---|
| 1 | 0 | —CH₂CH₂— | —CH₂— | >CH— | —CH₂— | Ph | | | |
| 2 | 0 | —CH₂CH₂— | —CH₂— | >CH— | —(CH₂)₂— | Ph | | | |
| 3 | 0 | —CH₂CH₂— | —CH₂— | >CH— | —(CH₂)₃— | Ph | | | |
| 4 | 0 | —CH=CH— | —CH₂— | >CH— | —CH₂— | Ph | | | |
| 5 | 0 | —CH=CH— | —CH₂— | >CH— | —(CH₂)₂— | Ph | | | |
| 6 | 0 | —CH=CH— | —CH₂— | >CH— | —(CH₂)₃— | Ph | | | |
| 7 | 0 | —CH=CH— | —CH₂— | >CH— | —CH₂— | Ph | | | OH |
| 8 | 0 | —CH₂CH₂— | —CH₂— | >CH— | —(CH₂)₂— | Ph | 4-MOMO | | |
| 9 | 0 | —CH₂CH₂— | —CH₂— | >CH— | —(CH₂)₂— | Ph | 2-MOMO | | |
| 10 | 0 | —CH₂CH₂— | —CH₂— | >CH— | —(CH₂)₂— | Ph | 3-MOMO | | |
| 11 | 0 | —CH₂CH₂— | —CH₂— | >CH— | —(CH₂)₂— | Ph | 2-MOMO, 4-MeO | | |

TABLE 1-continued

| Example No. | m | D=E | W | X=Y | Z | A | Substituent of A | R¹ | R² |
|---|---|---|---|---|---|---|---|---|---|
| 12 | 0 | —CH=CH— | —CH₂— | >CH— | —(CH₂)₂— | Ph | 4-MOMO | | |
| 13 | 0 | —CH=CH— | —CH₂— | >CH— | —(CH₂)₂— | Ph | 2-MOMO | | |
| 14 | 0 | —CH=CH— | —CH₂— | >CH— | —(CH₂)₂— | Ph | 3-MOMO | | |
| 15 | 0 | —CH=CH— | —CH₂— | >CH— | —(CH₂)₂— | Ph | 2-MOMO, 4-MeO | | |
| 16 | 0 | —CH=CH— | —CH₂— | >CH— | —(CH₂)₂— | Ph | 4-OH | | |
| 17 | 0 | —CH=CH— | —CH₂— | >CH— | —(CH₂)₂— | Ph | 2-OH | | |
| 18 | 0 | —CH=CH— | —CH₂— | >CH— | —(CH₂)₂— | Ph | 3-OH | | |
| 19 | 0 | —CH=CH— | —CH₂— | >CH— | —(CH₂)₂— | Ph | 2-OH, 4-MeO | | |
| 20 | 1 | —CH₂CH₂— | —CH₂CH₂— | >CH— | —CH₂— | Ph | | | |
| 21 | 1 | —CH₂CH₂— | —CH₂CH₂— | >CH— | | Ph | | | |
| 22-a | 1 | —CH=CH— | —CH₂CH₂— | >CH— | —CH₂— | Ph | | | |
| 22-b | 1 | —CH=CH— | —CH₂CH₂— | >CH— | —CH₂— | Ph | | | |
| 22-c | 1 | —CH=CH— | —CH=CH— | >CH— | —CH₂— | Ph | | | |
| 23-a | 1 | —CH=CH— | —CH₂CH₂— | >CH— | | Ph | | | |
| 23-b | 1 | —CH=CH— | —CH₂CH₂— | >CH— | | Ph | | | |
| 24 | 0 | —CH₂CH₂— | —CH₂— | >C=CH— | | 2-Pyr | | | |
| 25 | 0 | —CH=CH— | —CH₂— | >C=CH— | | 2-Pyr | | | |
| 26 | 0 | —CH₂CH₂— | —CH₂— | >CH— | —CH₂— | 2-Pyr | | | |
| 27 | 0 | —CH=CH— | —CH₂— | >CH— | —CH₂— | 2-Pyr | | | |
| 28 | 0 | —CH₂CH₂— | —CH₂— | >CH— | CH₂—CH(OBzM)— | Ph | 2-MOMO | | |
| 29 | 0 | —CH=CH— | —CH₂— | >CH— | CH₂—CH(OBzM)— | Ph | 2-MOMO | | |
| 30 | 0 | —CH=CH— | —CH₂— | >CH—CH₂—CH(OH)— | | Ph | 2-MOMO | | |
| 31 | 0 | —CH=CH— | —CH₂— | >CH—CH₂—C(=O)— | | Ph | 2-MOMO | | |
| 32 | 0 | —CH=CH— | —CH₂— | >CH—CH₂—C(=O)— | | Ph | 2-MOMO, 4-MeO | | |
| 33 | 0 | —CH₂CH₂— | —CH₂— | >CH—O—C(=O)— | | Ph | 2-MOMO, 4-MeO | | |
| 34 | 0 | —CH₂CH₂— | —CH₂— | >CH—O—C(=O)— | | Ph | 2-MOMO | | |
| 35 | 1 | —CH₂CH₂— | —CH₂CH₂— | >CH—O—C(=O)— | | Ph | | | |
| 36 | 1 | —CH₂CH₂— | —CH₂CH₂— | >CH—O—C(=O)— | | Ph | 2-MOMO | | |
| 37 | 1 | —CH₂CH₂— | —CH₂CH₂— | >CH—O—C(=O)— | | Ph | 2-MOMO, 4-MeO | | |
| 38 | 1 | —CH₂CH₂— | —CH₂CH₂— | >CH—O—C(=O)— | | Ph | 2-NO₂ | | |
| 39 | 1 | —CH₂CH₂— | —CH₂CH₂— | >CH—O—C(=O)— | | Ph | 4-MeO | | |
| 40 | 0 | —CH=CH— | —CH₂— | >CH—O—C(=O)— | | Ph | 2-MOMO, 4-MeO | | |
| 41 | 0 | —CH=CH— | —CH₂— | >CH—O—C(=O)— | | Ph | 2-MOMO | | |
| 42 | 1 | —CH=CH— | —CH₂CH₂— | >CH—O—C(=O)— | | Ph | | | |
| 43 | 1 | —CH=CH— | —CH₂CH₂— | >CH—O—C(=O)— | | Ph | 2-MOMO | | |
| 44 | 1 | —CH=CH— | —CH₂CH₂— | >CH—O—C(=O)— | | Ph | 2-MOMO, 4-MeO | | |
| 45 | 1 | —CH=CH— | —CH₂CH₂— | >CH—O—C(=O)— | | Ph | 2-NO₂ | | |
| 46 | 1 | —CH=CH— | —CH₂CH₂— | >CH—O—C(=O)— | | Ph | 4-MeO | | |
| 47 | 0 | —CH=CH— | —CH₂— | >CH—O—C(=O)— | | Ph | 2-OH, 4-MeO | | |
| 48 | 0 | —CH=CH— | —CH₂— | >CH—O—C(=O)— | | Ph | 2-OH | | |
| 49 | 1 | —CH=CH— | —CH₂CH₂— | >CH—O—C(=O)— | | Ph | 2-OH | | |
| 50 | 1 | —CH=CH— | —CH₂CH₂— | >CH—O—C(=O)— | | Ph | 2-OH, 4-MeO | | |
| 51 | 0 | —CH₂CH₂— | —CH₂— | >CH— | —(CH₂)₂— | Ph | | OH | OH |
| 52 | 0 | —CH₂CH₂— | —CH₂— | >CH— | —(CH₂)₂— | Ph | 2-MOMO | OH | OH |
| 53 | 0 | —CH₂CH₂— | —CH₂— | >CH— | —(CH₂)₂— | Ph | 3-MOMO | OH | OH |
| 54 | 1 | —CH₂CH₂— | —CH₂CH₂— | >CH— | —CH₂— | Ph | | OH | OH |
| 55 | 1 | —CH₂CH₂— | —CH₂CH₂— | >CH— | | Ph | | OH | OH |
| 56 | 0 | —CH₂CH₂— | —CH₂— | >CH—O—C(=O)— | | Ph | 2-MOMO | OH | OH |
| 57 | 1 | —CH₂CH₂— | —CH₂CH₂— | >CH—O—C(=O)— | | Ph | | OH | OH |
| 58 | 1 | —CH₂CH₂— | —CH₂CH₂— | >CH—O—C(=O)— | | Ph | 2-MOMO | OH | OH |
| 59 | 1 | —CH₂CH₂— | —CH₂CH₂— | >CH—O—C(=O)— | | Ph | 2-MOMO, 4-MeO | OH | OH |
| 60 | 1 | —CH₂CH₂— | —CH₂CH₂— | >CH—O—C(=O)— | | Ph | 2-NO₂ | OH | OH |
| 61 | 1 | —CH₂CH₂— | —CH₂CH₂— | >CH—O—C(=O)— | | Ph | 4-MeO | OH | OH |
| 62-a | 0 | —CH₂CH₂— | —CH₂— | >CH— | —(CH₂)₂— | Ph | | MOMO | MOMO |
| 62-b | 0 | —CH₂CH₂— | —CH₂— | >CH— | —(CH₂)₂— | Ph | | MOMO | OH |
| 63 | 0 | —CH₂CH₂— | —CH₂— | >CH— | —(CH₂)₂— | Ph | 2-MOMO | MOMO | MOMO |
| 64 | 0 | —CH₂CH₂— | —CH₂— | >CH— | —(CH₂)₂— | Ph | 3-MOMO | MOMO | MOMO |
| 65 | 1 | —CH₂CH₂— | —CH₂CH₂— | >CH— | —CH₂— | Ph | | MOMO | MOMO |
| 66 | 1 | —CH₂CH₂— | —CH₂CH₂— | >CH— | | Ph | | MOMO | MOMO |
| 67 | 0 | —CH₂CH₂— | —CH₂— | >CH—O—C(=O)— | | Ph | | MOMO | MOMO |
| 68 | 1 | —CH₂CH₂— | —CH₂CH₂— | >CH—O—C(=O)— | | Ph | | MOMO | MOMO |
| 69 | 1 | —CH₂CH₂— | —CH₂CH₂— | >CH—O—C(=O)— | | Ph | 2-MOMO | MOMO | MOMO |
| 70 | 1 | —CH₂CH₂— | —CH₂CH₂— | >CH—O—C(=O)— | | Ph | 2-MOMO, 4-MeO | MOMO | MOMO |
| 71 | 1 | —CH₂CH₂— | —CH₂CH₂— | >CH—O—C(=O)— | | Ph | 2-NO₂ | MOMO | MOMO |
| 72 | 1 | —CH₂CH₂— | —CH₂CH₂— | >CH—O—C(=O)— | | Ph | 4-MeO | MOMO | MOMO |
| 73 | 0 | —CH=CH— | —CH₂— | >CH— | —(CH₂)₂— | Ph | | MOMO | MOMO |
| 74 | 0 | —CH=CH— | —CH₂— | >CH— | —(CH₂)₂— | Ph | 2-MOMO | MOMO | MOMO |
| 75 | 0 | —CH=CH— | —CH₂— | >CH— | —(CH₂)₂— | Ph | 3-MOMO | MOMO | MOMO |
| 76 | 1 | —CH=CH— | —CH₂CH₂— | >CH— | —CH₂— | Ph | | MOMO | MOMO |
| 77 | 1 | —CH=CH— | —CH₂CH₂— | >CH— | | Ph | | MOMO | MOMO |
| 78 | 0 | —CH=CH— | —CH₂— | >CH—O—C(=O)— | | Ph | 2-MOMO | MOMO | MOMO |
| 79 | 1 | —CH=CH— | —CH₂CH₂— | >CH—O—C(=O)— | | Ph | | MOMO | MOMO |
| 80 | 1 | —CH=CH— | —CH₂CH₂— | >CH—O—C(=O)— | | Ph | 2-MOMO | MOMO | MOMO |
| 81 | 1 | —CH=CH— | —CH₂CH₂— | >CH—O—C(=O)— | | Ph | 2-MOMO, 4-MeO | MOMO | MOMO |
| 82 | 1 | —CH=CH— | —CH₂CH₂— | >CH—O—C(=O)— | | Ph | 2-NO₂ | MOMO | MOMO |
| 83 | 1 | —CH=CH— | —CH₂CH₂— | >CH—O—C(=O)— | | Ph | 4-MeO | MOMO | MOMO |
| 84 | 0 | —CH=CH— | —CH₂— | >CH— | —(CH₂)₂— | Ph | | OH | OH |

TABLE 1-continued

| Example No. | m | D=E | W | X=Y | Z | A | Substituent of A | $R^1$ | $R^2$ |
|---|---|---|---|---|---|---|---|---|---|
| 85 | 0 | —CH=CH— | —CH$_2$— | >CH— | —(CH$_2$)$_2$— | Ph | 2-OH | OH | OH |
| 86 | 0 | —CH=CH— | —CH$_2$— | >CH— | —(CH$_2$)$_2$— | Ph | 3-OH | OH | OH |
| 87 | 1 | —CH=CH— | —CH$_2$CH$_2$— | >CH— | —CH$_2$— | Ph |  | OH | OH |
| 88 | 1 | —CH=CH— | —CH$_2$CH$_2$— | >CH— |  | Ph |  | OH | OH |
| 89 | 1 | —CH=CH— | —CH$_2$CH$_2$— | >CH— |  | Ph |  | MOMO | OH |
| 90 | 0 | —CH=CH— | —CH$_2$— | >CH—O—C(=O)— |  | Ph | 2-OH | OH | OH |
| 91 | 1 | —CH=CH— | —CH$_2$CH$_2$— | >CH—O—C(=O)— |  | Ph |  | OH | OH |
| 92 | 1 | —CH=CH— | —CH$_2$CH$_2$— | >CH—O—C(=O)— |  | Ph | 2-OH | OH | OH |
| 93 | 1 | —CH=CH— | —CH$_2$CH$_2$— | >CH—O—C(=O)— |  | Ph | 2-OH, 4-MeO | OH | OH |
| 94 | 1 | —CH=CH— | —CH$_2$CH$_2$— | >CH—O—C(=O)— |  | Ph | 2-NO$_2$ | OH | OH |
| 95 | 1 | —CH=CH— | —CH$_2$CH$_2$— | >CH—O—C(=O)— |  | Ph | 4-MeO | OH | OH |

Test Example 1

Inhibitory Activity of Human Peripheral Blood Monocyte to Produce TNF-α and IL-6 Production TNF-α and IL-6 production inhibitory activity of the compound of the present invention was evaluated by determining the amounts of TNF-α and IL-6 produced by the human peripheral blood monocyte stimulated with lipopolysaccharide(LPS). Briefly, human peripheral blood monocyte fraction was isolated from the peripheral venous blood from healthy male volunteers by density gradient centrifugation with Ficoll-Paque (Pharmacia). The monocytes were suspended in RPMI 1640 medium (Gibco BRL) containing 10% FCS and seeded at 5×10$^5$ cell/160 µl in a 96-well plate.

The present compound was added to the monocytes cultured and the mixture was left at 37° C. for thirty minutes. Then the monocytes were stimulated by adding LPS (Sigma) at a final concentration of 10 ng/ml and left 37° C. for eighteen hours. For control, the cells were used wherein LPS was added to the cell at a final concentration of 10 ng/ml without the present compound.

The amount of each of TNF-α and IL-6, which were released in the culture supernatant, was measured using an ELISA kit (R & D). The inhibitory rate (%) of TNF-α and IL-6 production as compared to control was calculated using the following formula from the amounts of TNF-α and IL-2 thus measured:

$$\text{Inhibitory rate} = \frac{(\text{Amount produced with compound})}{(\text{Amount produced without compound})} \times 100$$

In addition, the concentration of the present compound to inhibit 50% (IC$_{50}$) was calculated by plotting the inhibitory rate (%) of IL-6 and TNF-α production obtained by varying a final concentration of the present compound of from 0.1 µM to 100 µM. Results are shown in Table 2.

TABLE 2

| Compound | TNF-α Production IC$_{50}$ µM | IL-6 Production IC$_{50}$ µM |
|---|---|---|
| Example 4 | 13.6 | 23.3 |
| Example 5 | 13.7 | 21.6 |
| Example 18 | 5.9 | 6.8 |
| Example 22 (a) | 28.1 |  |
| Example 47 | 0.50 |  |
| Example 84 (b) | 8.8 |  |
| Example 85 (a) | 2.2 |  |
| Example 87 | 12.4 |  |
| Example 90 (a) | 3.4 |  |

TABLE 2-continued

| Compound | TNF-α Production IC$_{50}$ µM | IL-6 Production IC$_{50}$ µM |
|---|---|---|
| Example 92 | 1.7 |  |
| Example 93 | 1.8 |  |

As can be seen from Table 2, the present compound inhibited TNF-α and IL-2 production.

Test Example 2

Inhibitory Activity of Human Peripheral Lymphocyte to Produce IL-2 Production

Human peripheral lymphocytes were stimulated with mitogen (PHA) to induce IL-2 production. The amount of IL-2 produced was measured to evaluate the inhibitory effect of the present compound. Briefly, human peripheral blood monocyte fraction was isolated in a manner similar to Test Example 1.

The monocytes were suspended in RPM 1640 medium (Gibco BRL) containing 10% FCS and seeded in a petri dish and left at 37° C. for an hour. Then, the cells (lymphocytes) which were not attached to the wall of the petri desh were isolated by centrifugation. The lymphocytes collected were suspended in the medium and seeded at 5×10$^5$ cell/160 µl in a 96-well plate.

The present compound was added to the lymphocytes cultured and the mixture was left at 37° C. for thirty minutes. Then, the cells were stimulated by adding PHA (Difco) at a final concentration of 10 µl/ml and left at 37° C. for forty eight hours. For control, the cells were used wherein PHA was added to the cell at a final concentration of 10 µl/ml without the present compound.

The amount of IL-2 which was released in the culture supernatant was measured using an ELISA kit (BioSource International). The inhibitory rate (%) of IL-2 production as compared to control was calculated using the following formula from IL-2 amounts thus measured:

$$\text{Inhibitory rate} = \frac{(\text{Amount produced with compound})}{(\text{Amount produced without compound})} \times 100$$

In addition, the concentration of the present compound to inhibit 50% (IC$_{50}$) was calculated by plotting the inhibitory rate (%) of IL-2 production obtained by varying a final concentration of the present compound of from 0.1 µM to 100 µM. Results are shown in Table 3.

TABLE 3

| Compound | IL-2 Production IC$_{50}$ $\mu$M |
|---|---|
| Example 5 | 1.7 |
| Example 18 | 2.1 |
| Example 22 (a) | 2.6 |
| Example 47 | 0.14 |
| Example 84 (b) | 3.6 |
| Example 85 (a) | 64.9 |
| Example 87 | 3.0 |
| Example 92 | 1.2 |
| Example 93 | 2.0 |

Table 3 shows that the present compound inhibited IL-2 production.

What is claimed is:

1. A compound represented by the following general formula (I) wherein A represents a five- to fourteen-membered aromatic group, which may be substituted, or a cycloaliphatic hydrocarbon group, which may be substituted, having from three to ten carbon atoms;

the partial structure -D---E- represents a group represented by —CH$_2$CH$_2$— or —CH=CH—;

W represents a group represented by —CH$_2$—, —CH$_2$CH$_2$—, —CH=CH— or —CH≡; the partial structure >X---Y— represents a group represented by the formula >CH—(CH$_2$)$_n$—, wherein n is an integer of 0 or 1; >C=CH—; >CH—CH$_2$—CH(OH)—; >CH—CH$_2$—C(=O)—; >CH—O—; or >CH—O—CO—, provided that when W is —CH=CH—, then X---Y— represents the formula C—(CH$_2$)$_p$—, wherein p is an integer of 0 or 1;

Z represents a divalent aliphatic hydrocarbon group having from zero to eight carbon atoms;

R$^1$ and R$^2$, which may be the same or different, each represents a hydrogen atom, a hydroxyl group, a C$_{1-6}$ alkoxy group or a C$_{1-6}$ alkoxy-C$_{1-6}$ alkoxy group, provided that when R$^2$ represents a hydrogen atom, R$^1$ also represents a hydrogen atom;

m is an integer of 0 or 1, and when W represents —CH$_2$— or —CH=, then m is 0, and when W represents —(CH$_2$)$_2$— or —CH=CH—, then m is 1;

with exception of the compound represented by the following formulae X or Y; or salts thereof or hydrates thereof:

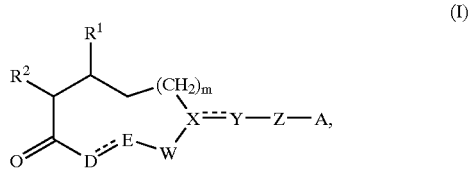
(I)

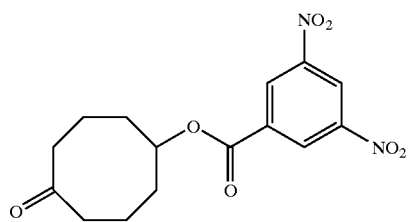
Formula (X)

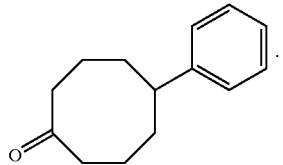
Formula (Y)

2. The compound according to claim 1, wherein A is a five- to fourteen-membered aromatic heterocyclic group, which may be substituted; or salts thereof or hydrates thereof.

3. The compound according to claim 1, wherein A is a phenyl, naphthyl, pyridyl, pyridazinyl, pyrimidinyl, pyrazinyl, thienyl, furyl, oxazolyl or thiazolyl group, each of which may be substituted; or salts thereof or hydrates thereof.

4. The compound according to claim 1, wherein A is a phenyl or pyridyl group, each of which may be substituted; or salts thereof or hydrates thereof.

5. The compound according to claim 1, wherein R$^2$ and/or R$^1$ are a hydroxyl group; or salts thereof or hydrates thereof.

6. The compound according to claim 1, wherein R$^1$ and/or R$^2$ are a C$_{1-6}$ alkoxy-C$_{1-6}$ alkoxy group; or salts thereof or hydrates thereof.

7. The compound according to claim 1, wherein the partial structure -D---E- represents —CH=CH—; or salts thereof or hydrates thereof.

8. The compound according to claim 1, wherein W represents —CH$_2$— or —CH=, and wherein m is 0; or salts thereof or hydrates thereof.

9. The compound according to claim 1, wherein W represents —(CH$_2$)$_2$— or —CH=CH—, and wherein m is 1; or salts thereof or hydrates thereof.

10. The compound according to claim 1, wherein the partial structure >X---Y— represents the formula >CH—(CH$_2$)$_n$— (wherein n is an integer of 0 or 1), the formula >C=CH—, the formula >CH—CH$_2$—CH(OH)—, the formula >CH—CH$_2$—C(=O)— or the formula >CH—O—; or salts thereof or hydrates thereof.

11. The compound according to claim 1, wherein the partial structure >X---Y— represents >CH—(CH$_2$)$_n$— (wherein n is an integer of 0 or 1); or salts thereof or hydrates thereof.

12. The compound according to claim 1, wherein A is an aromatic or cycloaliphatic group which may have one to three groups selected from a hydroxyl group or an alkoxy group which may be substituted; or salts thereof or hydrates thereof.

13. The compound according to claim 1, wherein the compound is selected from the group consisting of 5-benzyl-1-cyclooctanone, 5-phenethyl-1-cyclooctanone, 5-(2-pyridylmethyl)-1-cyclooctanone, 5-[2-(2-hydroxyphenyl)ethyl]-1-cyclooctanone, 5-[2-(2-hydroxy-4-methoxyphenyl)ethyl]-1-cyclooctanone, 5-benzyl-2-cycloocten-1-one, 5-phenethyl-2-cycloocten-1-one, 5-(2-pyridylmethyl)-2-cycloocten-1-one, 5-[2-(2-hydroxy-4-methoxyphenyl)ethyl]-2-cycloocten-1-one, 5-benzyl-8-hydroxy-2-cycloocten-1-one, 5-benzyl-7,8-dihydroxy-2-cycloocten-1-one, 2,3-dihydroxy-5-[2-(2-hydroxyphenyl)ethyl]-1-cyclooctanone, 5-oxocyclooctyl benzoate, 5-oxo-3-cyclooctenyl benzoate, 5-oxocyclooctyl 2-hydroxybenzoate, 5-oxo-3-cyclooctenyl 2-hydroxybenzoate, 5-oxo-3-cyclooctenyl (2-methoxymethoxy)benzoate, 5-oxocyclooctyl (2-hydroxy-4-methoxy)benzoate, 5-oxo-3-cyclooctenyl (2-hydroxy-4-methoxy)benzoate, 5-oxo-3-cyclooctenyl 2-nitrobenzoate, 3,4-dihydroxy-5-oxocyclooctyl benzoate, 6,7-dihydroxy-5-oxo-3-cyclooctenyl benzoate, 6,7-dihydroxy-5-oxo-3-cyclooctenyl 2-hydroxybenzoate, 3,4-dihydroxy-5-oxocyclooctyl (2-methoxymethoxy)benzoate, 3,4-dihydroxy-5-oxocyclooctyl (2-hydroxy-4-methoxy)benzoate, 6,7-dihydroxy-5-oxo-3-cyclooctenyl (2-hydroxy-4-methoxy)-benzoate, 6,7-dihydroxy-5-oxo-3-cyclooctenyl 2-nitrobenzoate, 6-benzyl-1-cyclodecanone, 6-phenethyl-1-cyclodecanone, 6-(2-pyridylmethyl)-1-cyclodecanone, 6-[2-(2-hydroxyphenyl)ethyl]-1-cyclodecanone, 6-[2-(2-hydroxy-4-methoxyphenyl)ethyl]1-cyclodecanone, 6-benzyl-2-cyclodecen-1-one, 6-phenethyl-2-cyclodecen-1-one, 6-(2-pyridylmethyl)-2-cyclodecen-1-one, 6-[2-(2-hydroxy-4-methoxyphenyl)ethyl]-2-cyclodecen-1-one, 6-benzyl-10-hydroxy-2-cyclodecen-1-one, 6-benzyl-9,10-dihydroxy-2-cyclodecen-1-one, 9,10-dihydroxy-6-phenethyl-cyclodecen-1-one, 9,10-dihydroxy-6-[2-(2-hydroxyphenyl)ethyl]cyclodecen-1-one, 6-oxocyclodecyl benzoate, 6-oxo-4-cyclodecenyl benzoate, 6-oxocyclodecyl 2-hydroxybenzoate, 6-oxo-4-cyclodecenyl 2-hydroxybenzoate, 6-oxo-4-cyclodecenyl 4-methoxybenzoate, 6-oxocyclodecyl (2-hydroxy-4-methoxy)benzoate, 6-oxo-4-cyclodecenyl (2-hydroxy-4-methoxy)benzoate, 6-oxocyclodecyl 2-nitrobenzoate, 6-oxo-4-cyclodecenyl 2-nitrobenzoate, 4,5-dihydroxy-6-oxocyclodecyl benzoate, 7,8-dihydroxy-6-oxo-4-cyclodecenyl benzoate, 7,8-dihydroxy-6-oxo-4-cyclodecenyl (2-methoxymethoxy)-benzoate, 7,8-dihydroxy-6-oxo-4-cyclodecenyl 4-methoxybenzoate, 7,8-dihydroxy-6-oxo-4-cyclodecenyl (2-hydroxy-4-methoxy)-benzoate, 4,5-dihydroxy-6-oxocyclodecyl 2-nitrobenzoate, and 7,8-dihydroxy-6-oxo-4-cyclodecenyl 2-nitrobenzoate; and salts thereof or hydrates thereof.

14. A pharmaceutical composition comprising the compound according to claim 1 or salts thereof or hydrates thereof and a pharmaceutically acceptable carrier.

* * * * *